(12) United States Patent
D'Andrea et al.

(10) Patent No.: US 9,725,425 B1
(45) Date of Patent: Aug. 8, 2017

(54) COMPOUNDS AND METHODS FOR TREATING CANCER

(71) Applicant: Dana-Farber Cancer Institute, Inc., Boston, MA (US)

(72) Inventors: Alan D. D'Andrea, Winchester, MA (US); Nathanael Gray, Boston, MA (US); Sara Jean Buhrlage, Somerville, MA (US); Kalindi Parmar, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/631,632

(22) Filed: Feb. 25, 2015

Related U.S. Application Data

(60) Provisional application No. 61/944,301, filed on Feb. 25, 2014.

(51) Int. Cl.
  *C07D 263/60* (2006.01)
  *C07D 413/04* (2006.01)

(52) U.S. Cl.
  CPC ......... *C07D 263/60* (2013.01); *C07D 413/04* (2013.01)

(58) Field of Classification Search
  None
  See application file for complete search history.

(56) References Cited

U.S. PATENT DOCUMENTS

| | | | |
|---|---|---|---|
| 3,039,925 | A | 6/1962 | Gerhard et al. |
| 5,217,964 | A | 6/1993 | Edwards et al. |
| 5,354,782 | A | 10/1994 | Edwards et al. |
| 5,434,145 | A | 7/1995 | Edwards et al. |
| 5,789,431 | A * | 8/1998 | Lee ............ C07C 233/32 514/393 |
| 6,114,394 | A | 9/2000 | Edwards et al. |
| 6,174,918 | B1 * | 1/2001 | Lee ............ C07C 233/32 514/510 |
| 6,262,095 | B1 | 7/2001 | Boutherin-Falson et al. |
| 6,287,858 | B1 | 9/2001 | D'Andrea et al. |
| 7,041,994 | B2 | 5/2006 | Hayashi et al. |
| 7,459,287 | B2 | 12/2008 | D'Andrea |
| 7,754,463 | B2 | 7/2010 | D'Andrea |
| 7,858,331 | B2 | 12/2010 | D'Andrea et al. |
| 8,518,660 | B2 | 8/2013 | Chelur et al. |
| 8,541,192 | B2 | 9/2013 | D'Andrea |
| 2004/0053324 | A1 | 3/2004 | Wong et al. |
| 2008/0167229 | A1 | 7/2008 | D'Andrea |
| 2009/0062196 | A1 | 3/2009 | D'Andrea et al. |
| 2009/0081237 | A1 | 3/2009 | D'Andrea et al. |
| 2010/0330599 | A1 | 12/2010 | D'Andrea |
| 2013/0253005 | A1 | 9/2013 | D'Andrea et al. |

FOREIGN PATENT DOCUMENTS

| | | |
|---|---|---|
| DE | 1111190 B | 7/1961 |
| DE | 2156317 A1 | 5/1973 |
| EP | 2 580 344 B1 | 11/2014 |
| GB | 2 146 653 A | 4/1985 |
| JP | 2011-042606 A | 3/2011 |
| WO | WO 95/11680 A1 | 5/1995 |
| WO | WO 97/21684 A1 | 6/1997 |
| WO | WO 97/21710 A1 | 6/1997 |
| WO | WO 97/30022 A1 | 8/1997 |
| WO | WO 98/37076 A1 | 8/1998 |
| WO | WO 2005/053609 A2 | 6/2005 |
| WO | WO 2007/120574 A2 | 10/2007 |
| WO | WO 2007/149484 A2 | 12/2007 |
| WO | WO 2008/030369 A1 | 3/2008 |
| WO | WO 2011/113060 A2 | 9/2011 |
| WO | WO 2011/137320 A2 | 11/2011 |

OTHER PUBLICATIONS

Invitation to Pay Additional Fees for PCT/US2011/034514 mailed Aug. 15, 2011.
International Search Report and Written Opinion for PCT/US2011/034514 mailed Nov. 4, 2011.
International Preliminary Report on Patentability for PCT/US2011/034514 mailed Nov. 15, 2012.
International Search Report and Written Opinion for PCT/US2007/014378 mailed May 27, 2008.
International Preliminary Report on Patentability for PCT/US2007/014378 mailed Jan. 8, 2009.
[No Author Listed], beta-Lapachone, ARQ-501, CO-501, 4707-32-8, C15-H14-03,2,2-Dim. Oct. 25, 2004; http://www.chemdrug.com/databases/8_0_vgbapjppdvcqsfww.html [last accessed Jan. 15, 2013]. 7 pages.
[No Author Listed], Cisplatin. Wikipedia. http://en.wikipedia.org/wiki/Cisplatin [last accessed Mar. 2, 2010]. 5 pages.
[No Author Listed], Definition of imides. Chemistry Dictionary. 1 page. http://www.chemicool.com/definition/imides.html [last accessed Mar. 31, 2010].
Aleksandrov et al., Oxidation products of fused 2-hetarylimidazole derivatives. Russian Journal of General Chemistry. Aug. 2011;81(8):1716-19.
Aly et al., Facile synthesis of new imidazoles from direct reaction of 2,3-diamino-1,4-naphthoquinone with aldehydes. J Heterocyclic Chem. 2011;48(4):787-91.

(Continued)

*Primary Examiner* — Kamal Saeed
(74) *Attorney, Agent, or Firm* — Wolf, Greenfield & Sacks, P.C.

(57) ABSTRACT

Provided are small molecule inhibitors of ubiquitin specific protease 2, 8 and 12 (USP2 and USP8 and USP12) activity and methods for their use in treating cancers. The small molecule inhibitors of the invention are particularly useful in the treatment of non-small cell lung cancers that are resistant to tyrosine kinase inhibitors and in the treatment of prostate cancer that is resistant to AR inhibitor therapy.

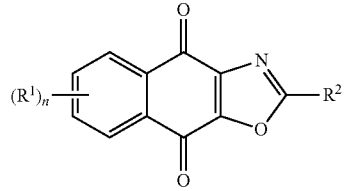

Formula A

16 Claims, 9 Drawing Sheets

(56) References Cited

OTHER PUBLICATIONS

Avvakumov et al., Amino-terminal dimerization, NRDP1-rhodanese interaction, and inhibited catalytic domain conformation of the ubiquitin-specific protease 8 (USP8). J Biol Chem. Dec. 8, 2006;281(49):38061-70. Epub Oct 11, 2006.
Babu et al., Synthesis of some substituted naphtho[2,3-d]thiazole-4,9-diones as potential fungicides. Current Science. 1967;36(7):176.
Benedetti-Doctorovich et al., Synthesis of 2-methyl-(Z)-4-(phenylimino)naphth[2,3-d]oxazol-9-one, a monoimine quinone with selective cytotoxicity toward cancer cells. J Med Chem. Mar. 4, 1994;37(5):710-2.
Berghot, New unexpected products during heteroannulation of 1,4-naphthoquinone derivatives. Chemical Papers. 2002;56(3):202-7.
Berlin et al., Regulation of epidermal growth factor receptor ubiquitination and trafficking by the USP8•STAM complex. J Biol Chem. Nov. 5, 2010;285(45):34909-21. doi:10.1074/jbc.M109.016287. Epub Aug. 24, 2010.
Boothman et al., Inhibition of radiation-induced neoplastic transformation by beta-lapachone. Proc Natl Acad Sci U S A. Jul. 1989;86(13):4963-7.
Brandy et al., Synthesis and cytotoxic activities of some 2-Arylnaphtho[2,3-d]oxazole-4,9-dione derivatives on androgen-dependent (LNCaP) and androgen-independent (PC3) human prostate cancer cell lines. Investigational New Drugs—Short Report. Online. Abstract Only. Jan. 18, 2011. 2 pages. http://www.springerlink.com/content/t8213654w5332083/ [last accessed Oct. 8, 2011].
Brandy et al., Synthesis and cytotoxic activities of some 2-Arylnaphtho[2,3-d]oxazole-4,9-dione derivatives on androgen-dependent (LNCaP) and androgen-independent (PC3) human prostate cancer cell lines. Investigational New Drugs. 2012;30(4):1709-14.
Bryant et al., Specific killing of BRCA2-deficient tumours with inhibitors of poly(ADP-ribose) polymerase. Nature. Apr. 14, 2005;434(7035):913-7. Erratum in: Nature. May 17, 2007;447(7142):346.
Burska et al., Deubiquitinating enzyme Usp12 is a novel co-activator of the androgen receptor. J Biol Chem. Nov. 8, 2013;288(45):32641-50. doi:10.1074/jbc.M113.485912. Epub Sep. 21, 2013.
Byun et al., USP8 is a novel target for overcoming gefitinib resistance in lung cancer. Clin Cancer Res. Jul. 15, 2013;19(14):3894-904. doi: 10.1158/1078-0432.CCR-12-3696. Epub Jun. 7, 2013.
Chen et al., Sequence and expression in *Escherichia coli* of the 40-kDa subunit of activator 1 (replication factor C) of HeLa cells. Proc Natl Acad Sci U S A. Apr. 1, 1992;89(7):2516-20.
Chirnomas et al., Chemosensitization to cisplatin by inhibitors of the Fanconi anemia/BRCA pathway. Mol Cancer Ther. Apr. 2006;5(4):952-61.
Clark, the fungicidal activity of substituted 1,4-naphthoquinones. Part III: amino, anilino and acylamino derivatives. Pesticide Science. 1985;16(1):23-32.
Cohen et al., CD4+ T-cells from mice immunized to syngeneic sarcomas recognize distinct, non-shared tumor antigens. Cancer Res. Feb. 15, 1994;54(4):1055-8.
Cohn et al., A UAF1-containing multisubunit protein complex regulates the Fanconi anemia pathway. Mol Cell. Dec. 14, 2007;28(5):786-97.
Cohn et al., UAF1 is a subunit of multiple deubiquitinating enzyme complexes. J Biol Chem. Feb. 20, 2009;284(8):5343-51. Epub Dec. 15, 2008.
Colland et al., Small-molecule inhibitor of USP7/HAUSP ubiquitin protease stabilizes and activates p53 in cells. Mol Cancer Ther. Aug. 2009;8(8):2286-95. Epub Aug. 11, 2009.
Colland, The therapeutic potential of deubiquitinating enzyme inhibitors. Biochem Soc Trans. Feb. 2010;38(Pt 1):137-43.

D'Andrea et al., The Fanconi Anemia and Breast Cancer Susceptibility Pathways. N Engl J Med. May 20, 2010;362(20):1909-19.
Dang et al., Kinetic and mechanistic studies on the hydrolysis of ubiquitin C-terminal 7-amido-4-methylcoumarin by deubiquitinating enzymes. Biochemistry. Feb. 17, 1998;37(7):1868-79.
De Oliveira et al., Synthesis and antimicrobial evaluation of oxazole-1,4-naphthquinones. Heterocyclic communications. 2002;8(2):199-204.
Efimova et al., Heterocyclic derivatives of substituted 1,4-naphthoquinones. IV Condensation of 2,3-diamino-1,4-naphthoquinone and its monomethyl derivative with 1,3-diketones. Zhurnal Organicheskoi Khimii. 1967;3(1):162-8.
Eiden et al., 4-Pyrones. 39. 2-Amino-4-hydroxychromones. Archiv der Pharmazie. 1972;305(9):698-701.
Farmer et al., Targeting the DNA repair defect in BRCA mutant cells as a therapeutic strategy. Nature. Apr. 14, 2005;434(7035):917-21.
Fields et al., A novel genetic system to detect protein-protein interactions. Nature. Jul. 20, 1989;340(6230):245-6.
Fong et al., Inhibition of poly(ADP-ribose) polymerase in tumors from BRCA mutation carriers. N Engl J Med. Jul. 9, 2009;361(2):123-34. Epub Jun. 24, 2009.
Fong et al., Poly(ADP)-ribose polymerase inhibition: frequent durable responses in BRCA carrier ovarian cancer correlating with platinum-free interval. J Clin Oncol. May 20, 2010;28(15):2512-9. Epub Apr. 20, 2010.
Fujiwara et al., Identification and chromosomal assignment of USP1, a novel gene encoding a human ubiquitin-specific protease. Genomics. Nov. 15, 1998;54(1):155-8.
Gao et al., Study on preparation of polyheterocyclic quinoid compounds and their third-order nonlinear optical properties. Gaojishu Tongxun. 1999;9(2):45-9.
Gao et al., Third-order nonlinear optical properties of polyheterocyclic quinoid compounds. Gongneng Cailiao. 1998;29(3):314-6.
Gavin et al., Functional organization of the yeast proteome by systematic analysis of protein complexes. Nature. Jan. 10, 2002;415(6868):141-7.
Gavin et al., Proteome survey reveals modularity of the yeast cell machinery. Nature. Mar. 30, 2006;440(7084):631-6. Epub Jan. 22, 2006.
Gayle et al., Identification of regions in interleukin-1 alpha important for activity. J Biol Chem. Oct. 15, 1993;268(29):22105-11.
Genbank Submission; NIH/NCBI, Accession No. AAH26072. Strausberg et al., Jul. 17, 2006. 2 pages.
Genbank Submission; NIH/NCBI, Accession No. EAW81771. Venter et al., Dec. 18, 2006. 2 pages.
Genbank Submission; NIH/NCBI, Accession No. NM_182649; Masuo et al.; Nov. 1, 2009. 4 pages.
Genbank Submission; NIH/NCBI, Accession No. NP_065890. Cohn et al., Mar. 12, 2010. 2 pages.
Genbank Submission; NIH/NCBI, Accession No. NP_073743. Cohn et al., Mar. 5, 2010. 2 pages.
Green-Buckley et al., Naphthoquinone colouring matters. Part 4. Amino-substituted 1,2-dimethylnaphth[2,3-d]imidazole-4,9-diones. J Chem Soc, Perkin Trans 1:702-7.
Hamaguchi et al., RK-682, a potent inhibitor of tyrosine phosphatase, arrested the mammalian cell cycle progression at G1phase. FEBS Lett. Sep. 18, 1995;372(1):54-8.
Hammam et al., Heterocyclic quinones. XVI. The reaction of acid amides with 2,3-dichloro-1,4-naphthoquinone, a novel route to naphth[2,3-d]oxazole-4,9-diones. Journal fuer Praktische Chemie. 1977;319(2):254-8.
Hay et al., Poly(ADP-ribose) polymerase-1 inhibitor treatment regresses autochthonous Brca2/p53-mutant mammary tumors in vivo and delays tumor relapse in combination with carboplatin. Cancer Res. May 1, 2009;69(9):3850-5. Epub Apr. 21, 2009.
Hershko et al., Ubiquitin-aldehyde: a general inhibitor of ubiquitin-recycling processes. Proc Natl Acad Sci U S A. Apr. 1987;84(7):1829-33.
Hirsch et al., Epidermal growth factor receptor in non-small-cell lung carcinomas: correlation between gene copy number and protein expression and impact on prognosis. J Clin Oncol. Oct. 15, 2003;21(20):3798-807. Epub Sep 2, 2003.

(56) References Cited

OTHER PUBLICATIONS

Hirsch et al., Increased EGFR gene copy number detected by fluorescent in situ hybridization predicts outcome in non-small-cell lung cancer patients treated with cetuximab and chemotherapy. J Clin Oncol. Jul. 10, 2008;26(20):3351-7. doi: 10.1200/JCO.2007.14.0111.

Ho et al., Systematic identification of protein complexes in *Saccharomyces cerevisiae* by mass spectrometry. Nature. Jan. 10, 2002;415(6868):180-3.

Hoege et al., RAD6-dependent DNA repair is linked to modification of PCNA by ubiquitin and SUMO. Nature. Sep. 12, 2002;419(6903):135-41.

Hu et al., Crystal structure of a UBP-family deubiquitinating enzyme in isolation and in complex with ubiquitin aldehyde. Cell. Dec. 27, 2002;111(7):1041-54.

Huang et al., HAUSP hunting the FOX(O). Nat Cell Biol. Oct. 2006;8(10):1043-5.

Huang et al., Regulation of DNA repair by ubiquitylation. Nat Rev Mol Cell Biol. May 2006;7(5):323-34.

Huang et al., Regulation of monoubiquitinated PCNA by DUB autocleavage. Nat Cell Biol. Apr. 2006;8(4):339-47. Epub Mar. 12, 2006.

Ingvarsdottir et al., H2B ubiquitin protease Ubp8 and Sgf11 constitute a discrete functional module within the *Saccharomyces cerevisiae* SAGA complex. Mol Cell Biol. Feb. 2005;25(3):1162-72.

Katz et al., Effect of the structure of exogenous quinone on its ability to function as the primary quinone in the reaction centers from Rhodobacter sphaeroides R-26. Biologicheskie Membrany. 1991;8(5):468-75.

Kee et al., Expanded roles of the Fanconi anemia pathway in preserving genomic stability. Genes Dev. Aug. 15, 2010;24(16):1680-94.

Kee et al., WDR20 regulates activity of the USP12 × UAF1 deubiquitinating enzyme complex. J Biol Chem. Apr. 9, 2010;285(15):11252-7. Epub Feb. 10, 2010.

Kennedy et al., The Fanconi Anemia/BRCA pathway: new faces in the crowd. Genes Dev. Dec. 15, 2005;19(24):2925-40.

Kim et al., Inactivation of murine Usp1 results in genomic instability and a Fanconi anemia phenotype. Dev Cell. Feb. 2009;16(2):314-20.

Kita et al., An Intramolecular Cyclization of Phenol Derivatives Bearing Aminoquinones Using a Hypervalent Iodine Reagent. 1996;61(1):223-7.

Kohli et al., Biomarker-based targeting of the androgen-androgen receptor axis in advanced prostate cancer. Adv Urol. 2012;2012:781459. doi: 10.1155/2012/781459. Epub Aug. 22, 2012.

Korkhova et al., Derivatives of 2-benzazepine from 3-substituted 2-methylamino-1,4-naphthoquinones. Zhurnal Organicheskoi Khimii. 1975;11(10):2140-4.

Krieg et al., Synthesis of 1,4-diazepines. Liebigs Annalen der Chemie. 1988;8:799-801.

Krogan et al., Global landscape of protein complexes in the yeast *Saccharomyces cerevisiae*. Nature. Mar. 30, 2006;440(7084):637-43. Epub Mar. 22, 2006.

Kuznetsov et al., Heterocyclic derivatives based on substituted 1,4-naphthoquinones. I. Naphth[2,3-d]imidazole-4,9-diones. Zhurnal Organicheskoi Khimii. 1965;1(8):1458-65.

Kuznetsov et al., Polarographic study of ring-substituted naphtho[2,3-d]imidazole-4,9-diones and their quaternary salts. Zhurnal Obshchei Khimii. 1967;37(8):1802-9.

Le Texier et al., A biosynthetic microbial ability applied for the oxidative ring cleavage of non-natural heterocyclic quinones. Tetrahedron Letters. 2001;42(25):4135-7.

Lee et al., The deubiquitylation activity of Ubp8 is dependent upon Sgf11 and its association with the SAGA complex. Mol Cell Biol. Feb. 2005;25(3):1173-82.

Lien et al., Synthesis and antiplatelet, antiinflammatory, and antialergic activities of 2-substituted 3-chloro-1,4-naphthoquinone derivatives. Bioorg Med Chem. Dec. 1997;5(12):2111-20. Erratum in: Bioorg Med Chem Feb. 1998;6(2):251.

Liu et al., Discovery of inhibitors that elucidate the role of UCH-L1 activity in the H1299 lung cancer cell line. Chem Biol. Sep. 2003;10(9):837-46.

Luchansky et al., Substrate recognition and catalysis by UCH-L1. Biochemistry. Dec. 12, 2006;45(49):14717-25.

Lynch et al., Activating mutations in the epidermal growth factor receptor underlying responsiveness of non-small-cell lung cancer to gefitinib. N Engl J Med. May 20, 2004;350(21):2129-39. Epub Apr. 29, 2004.

Mermerian et al., Structure-activity relationship, kinetic mechanism, and selectivity for a new class of ubiquitin C-terminal hydrolase-L1 (UCH-L1) inhibitors. Bioorg Med Chem Lett. Jul. 1, 2007;17(13):3729-32. Epub Apr. 10, 2007.

Mikhnov'ka et al., Antimicrobial properties of some imidazole derivatives. Mikrobiologichnii Zhurnal. 1967;29(3):242-6.

Mistry et al., Small-molecule inhibitors of USP1 target ID1 degradation in leukemic cells. Mol Cancer Ther. Dec. 2013;12(12):2651-62. doi:10.1158/1535-7163.MCT-13/0103-T. Epub Oct. 15, 2013.

Mizuno et al., Regulation of epidermal growth factor receptor down-regulation by UBPY-mediated deubiquitination at endosomes. Mol Biol Cell. Nov. 2005;16(11):5163-74. Epub Aug. 24, 2005.

Moldovan et al., How the fanconi anemia pathway guards the genome. Annu Rev Genet. 2009;43:223-49.

Mulloy et al., Epidermal growth factor receptor mutants from human lung cancers exhibit enhanced catalytic activity and increased sensitivity to gefitinib. Cancer Res. Mar. 1, 2007;67(5):2325-30.

Nakanishi et al., Human Fanconi anemia monoubiquitination pathway promotes homologous DNA repair. Proc Natl Acad Sci U S A. Jan. 25, 2005;102(4):1110-5. Epub Jan. 13, 2005.

Nakatani et al., Immunoaffinity purification of mammalian protein complexes. Methods Enzymol. 2003;370:430-44.

Nicholson et al., EGFR and cancer prognosis. Eur J Cancer. Sep. 2001;37 Suppl 4:S9-15.

Niendorf et al., Essential role of ubiquitin-specific protease 8 for receptor tyrosine kinase stability and endocytic trafficking in vivo. Mol Cell Biol. Jul. 2007;27(13):5029-39. Epub Apr. 23, 2007.

Nijman et al., A genomic and functional inventory of deubiquitinating enzymes. Cell. Dec. 2, 2005;123(5):773-86.

Nijman et al., The deubiquitinating enzyme USP1 regulates the Fanconi anemia pathway. Mol Cell. Feb. 4, 2005;17(3):331-9.

Oestergaard et al., Deubiquitination of FANCD2 is required for DNA crosslink repair. Mol Cell. Dec. 14, 2007;28(5):798-809.

Park et al., Herpesviral protein targets a cellular WD repeat endosomal protein to downregulate T lymphocyte receptor expression. Immunity. Aug. 2002;17(2):221-33.

Pickart et al., Ubiquitin: structures, functions, mechanisms. Biochim Biophys Acta. Nov. 29, 2004;1695(1-3):55-72.

Prescott, Potential antimalarial agents. Derivatives of 2-chloro-1,4-naphthoquinone. J Med Chem. Jan. 1969;12(1):181-2.

Priolo et al., The isopeptidase USP2a protects human prostate cancer from apoptosis. Cancer Res. Sep. 1, 2006;66(17):8625-32.

Qui et al., hRpn13/ADRM1/GP110 is a novel proteasome subunit that binds the deubiquitinating enzyme, UCH37. EMBO J. Dec. 13, 2006;25(24):5742-53. Epub Nov. 30, 2006.

Renatus et al., Structural basis of ubiquitin recognition by the deubiquitinating protease USP2. Structure. Aug. 2006;14(8):1293-302.

Rumpf et al., Functional division of substrate processing cofactors of the ubiquitin-selective Cdc48 chaperone. Mol Cell. Jan. 20, 2006;21(2):261-9.

Shan et al., Suppression of cancer cell growth by promoting cyclin Dl degradation. Mol Cell. Nov. 13, 2009;36(3):469-76. doi:10.1016/j.molcel.2009.10.018.

Sharma et al., Epidermal growth factor receptor mutations in lung cancer. Nat Rev Cancer. Mar. 2007;7(3):169-81.

Simonetti et al., Detection of EGFR mutations with mutation-specific antibodies in stage IV non-small-cell lung cancer. J Transl Med. Dec. 18, 2010;8:135. doi:10.1186/1479-5876-8-135.

(56) References Cited

OTHER PUBLICATIONS

Sondhi et al., A Convenient, Solvent Free and High Yielding Synthesis of Bicyclo-Heterocyclic Compounds. Lett. Org. Chem. Jan. 2008;5(1):51-54.

Sordella et al., Gefitinib-sensitizing EGFR mutations in lung cancer activate anti-apoptotic pathways. Science. Aug. 20, 2004;305(5687):1163-7. Epub Jul. 29, 2004.

Sowa et al., Defining the human deubiquitinating enzyme interaction landscape. Cell. Jul. 23, 2009;138(2):389-403. Epub Jul. 16, 2009.

Stetsenko et al., Algicidal action of condensed imidazole derivatives. Tsvetenie Vody;2:186-97.

Tomida et al., Usp46 is a quantitative trait gene regulating mouse immobile behavior in the tail suspension and forced swimming tests. Nat Genet. Jun. 2009;41(6):688-95. Epub May 24, 2009.

Truitt et al., 1,2-Disubstituted naphth[2,3-d]imidazole-4,9-diones and corresponding quaternary salts. J Med Chem. 1964;7(3):362-4.

Ungwitayatorn et al., Synthesis and HIV-1 Reverse Transcriptase Inhibitory Activity of Non-Nucleoside Phthalimide Derivatives. Chinese Journal of Chemistry. Feb. 2008;26(2):379-87.

Van Der Horst et al., FOXO4 transcriptional activity is regulated by monoubiquitination and USP7/HAUSP. Nat Cell Biol. Oct. 2006;8(10):1064-73. Epub Sep. 10, 2006.

Vanelle et al., Preparation and in vitro antiprotozoan activity of new naphthoimidazolediones. European Journal of Med Chem. Jun. 1997;32(6):523-28.

Wang et al., [1,1'-Bis(diphenylphosphino)ferrocene]dichloropalladium/1,1'-bis(diphenylphosphino)ferrocene catalyzed synthesis of 2,3-diamino-1,4-naphthoquinones. Synthesis. 2007. 7:989-98.

Whisstock et al., Prediction of protein function from protein sequence and structure. Q Rev Biophys. Aug. 2003;36(3):307-40.

Wishart et al., A single mutation converts a novel phosphotyrosine binding domain into a dual-specificity phosphatase. J Biol Chem. Nov. 10, 1995;270(45):26782-5.

Wong et al., Structural alterations of the epidermal growth factor receptor gene in human gliomas. Proc Natl Acad Sci U S A. Apr. 1, 1992;89(7):2965-9.

Yang et al., Regulation of the Fanconi anemia pathway by a SUMO-like delivery network. Genes Dev. Sep. 1, 2011;25(17):1847-58.

Yang et al., Targeted disruption of the murine Fanconi anemia gene, Fancg/Xrcc9. Blood. Dec. 1, 2001;98(12):3435-40.

Yao et al., Proteasome recruitment and activation of the Uch37 deubiquitinating enzyme by Adrm1. Nat Cell Biol. Sep. 2006;8(9):994-1002. Epub Aug. 13, 2006.

Zhang et al., A Simple Statistical Parameter for Use in Evaluation and Validation of High Throughput Screening Assays. J Biomol Screen. 1999;4(2):67-73.

\* cited by examiner

SJB3-019A reduces the viability of Prostate Cancer Cells

SJB3-019A reduces the viability of prostate cancer cells.

SJB3-019A promotes the degradation of Oncoprotein, Androgen receptor (AR), in prostate cancer cells.

COMPOUNDS AND METHODS FOR TREATING CANCER

RELATED APPLICATIONS

This Application claims the benefit under 35 U.S.C §119 (e) of U.S. Provisional Application Ser. No. 61/944,301, filed Feb. 25, 2014, the content of which is incorporated by reference herein in its entirety.

BACKGROUND OF THE INVENTION

Advanced non-small cell lung cancer (NSCLC) is the most common cause of cancer death for both men and women in the United States. In 2005 it is estimated that there will be over 170,000 new cases of NSCLC. Most patients are diagnosed with advanced disease and the median survival for these patients ranges from 8 to 10 months. Combination chemotherapy is the standard of care for patients with advanced NSCLC, but little progress towards improving the efficacy of chemotherapy has been made in the last 20 years.

Inhibitors of the epidermal growth factor receptor (EGFR) have emerged as therapies for some patients with NSCLC. Ubiquitin Specific Protease 8 (USP8), also known as ubiquitin specific peptidase 8 and as ubiquitin carboxyl terminal hydrolase 8, is implicated in the regulation of EGFR (Berlin et al. *J Biol Chem.* 2010 Nov. 5; 285(45):34909-21). Byun et al. have shown that inhibition of USP8 activity or reduction in USP8 expression can selectively kill NSCLC cells (Clin Cancer Res. 2013 Jul. 15; 19(14):3894-904). Thus, there is a need for effective USP8 inhibitors for the treatment of non-small cell lung cancer.

Approximately 2.5 million men in the United States are living with prostate cancer. Although survival has increased significantly in the past decade, more than 28,000 men die of metastatic castration-resistant prostate cancer (mCRPC) each year. Androgen deprivation in the form of castration, either medical or surgical, remains the backbone of prostate cancer treatment. Nevertheless, most prostate cancers eventually become resistant to traditional medical or surgical castration and require additional therapeutic interventions. Thus, there is a need for effective therapies for the treatment of prostate cancer.

SUMMARY OF THE INVENTION

The present invention is based, at least in part on the discovery that the compounds of the invention can promote the degradation of oncoproteins EGFR, cyclin D1 and androgen receptor (AR). Thus, the invention provides compositions and methods related to the compounds useful for the treatment of cancers driven by EGFR, cyclin D1 and AR such as non-small cell lung cancer (NSCLC) and prostate cancer.

In one aspect, the invention provides a compound of Formula A:

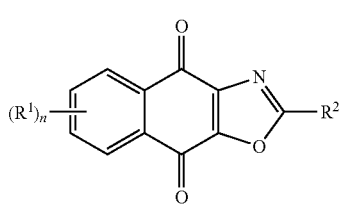

Formula A and pharmaceutically acceptable salts, solvates, hydrates, polymorphs, co-crystals, tautomers, stereoisomers, isotopically labeled derivatives, and prodrugs thereof, wherein $R^1$, $R^2$, and n are defined herein.

In another aspect, the invention provides a compound of Formula An-1:

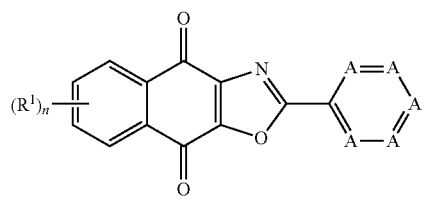

Formula An-1 and pharmaceutically acceptable salts, solvates, hydrates, polymorphs, co-crystals, tautomers, stereoisomers, isotopically labeled derivatives, and prodrugs thereof, wherein A, $R^1$, and n are defined herein.

In another aspect, the invention provides a compound of Formula Ac-1:

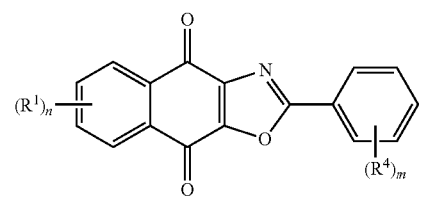

Formula Ac-1 and pharmaceutically acceptable salts, solvates, hydrates, polymorphs, co-crystals, tautomers, stereoisomers, isotopically labeled derivatives, and prodrugs thereof, wherein $R^1$, $R^4$, m, and n are defined herein.

In another aspect, the invention provides a compound from the group consisting of:

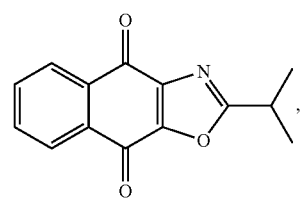

(1)

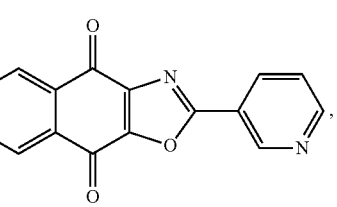

(2)

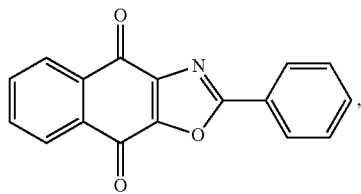

(3)

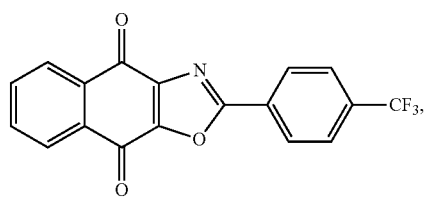

(4)

and

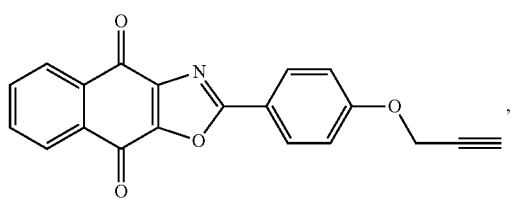

(5)

and pharmaceutically acceptable salts, solvates, hydrates, polymorphs, co-crystals, tautomers, stereoisomers, isotopically labeled derivatives, and prodrugs thereof.

Some aspects of the invention provide a method for treating epidermal growth factor receptor (EGFR)-mutant non-small cell lung cancer. The method comprises identifying a subject having an EGFR-mutant non-small cell lung cancer; and administering to the subject a compound according to Formula I:

Formula I

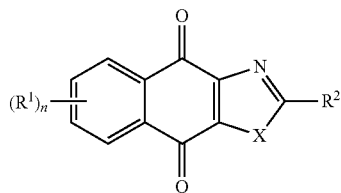

wherein

X is O, S, or $NR^3$;

n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^A$; $-C(=O)R^A$; $-C(=O)N(R^A)_2$; $-CO_2R^A$; $-CN$; $-SCN$; $-SR^A$; $-SOR^A$; $-SO_2R^A$; $-NO_2$; $-N_3$; $-N(R^A)_2$; $-NHC(=O)R^A$; $-NR^AC(=O)N(R^A)_2$; $-OC(=O)OR^A$; $-OC(=O)R^A$; $-OC(=O)N(R^A)_2$; $-NR^AC(=O)OR^A$; or $-C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^B$; $-C(=O)R^B$; $-C=(O)N(R^B)_2$; $-CO_2R^B$; $-CN$; $-SCN$; $-SR^B$; $-SOR^B$; $-SO_2R^B$; $-NO_2$; $-N_3$; $-N(R^B)_2$; $-NHC(=O)R^B$; $-NR^BC(=O)N(R^B)_2$; $-OC(=O)OR^B$; $-OC(=O)R^B$; $-OC(=O)N(R^B)_2$; $-NR^BC(=O)OR^B$; or $-C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the EGFR-mutant non-small cell lung cancer.

In some embodiments, the compound according to Formula I is compound of any one of Formula A, An-1, An-2, An-3, Ac-1, Ac-2, and Ac-3 described herein. In some embodiments, the compound according to Formula I is:

(527)

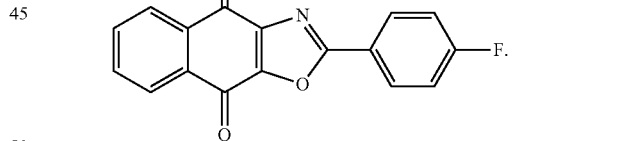

In some embodiments, the compound according to Formula I is:

(019A)

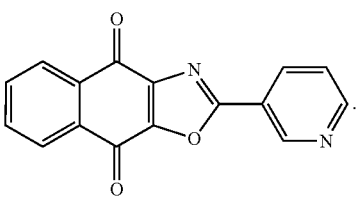

In some embodiments, the compound according to Formula I is:

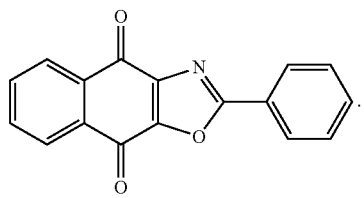

(043)

In some embodiments, the subject is identified as having the EGFR-mutant non-small cell lung cancer by performing an analysis of a sample obtained of the subject. In some embodiments, the sample is selected from the group consisting of blood, tumor tissue, sputum and urine. In some embodiments, the analysis of the sample comprises PCR-based assays, direct sequencing, primer extension reactions, electrophoresis, oligonucleotide ligation assays, hybridization assays, TaqMan assays, SNP genotyping assays, high resolution melting assays and/or microarray analysis. In some embodiments, the sample is analyzed using Cobas® EGFR Mutation Test. In some embodiments, the EGFR mutant non-small cell lung cancer has one or more EGFR activating mutations. In some embodiments, the activating mutation is selected from the group consisting of L858R, L861Q, G719S, del 19 and exon 20 insertions. In some embodiments, the EGFR mutant non-small cell lung cancer has one or more EGFR resistance mutations. In some embodiments, the resistance mutation is T790M.

Some aspects of the invention provide a method for treating non-small cell lung cancer resistant to at least one of gefitinib, erlotinib and lapatinib. The method comprises administering to a subject in need thereof a compound according to Formula I:

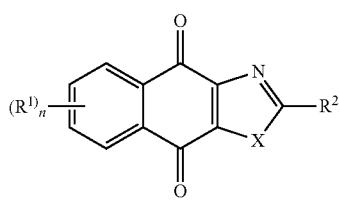

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R^A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy;
aryloxy; alkylthio; arylthio; amino, alkylamino, dialkylamino, heteroaryloxy; or a heteroarylthio moiety;
or a pharmaceutically acceptable salt thereof,
in an amount effective to treat the non-small cell lung cancer resistant to at least one of gefitinib, erlotinib and lapatinib.

In some embodiments, the compound according to Formula I is the compound of any one of Formula A, An-1, An-2, An-3, Ac-1, Ac-2, and Ac-3 described herein. In some embodiments, the compound according to Formula I is:

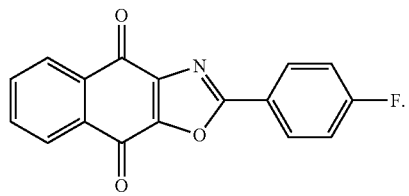

(527)

In some embodiments, the compound according to Formula I is:

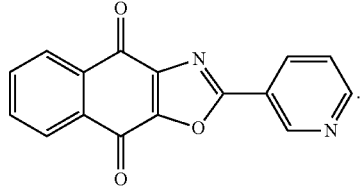

(019A)

In some embodiments, the compound according to Formula I is:

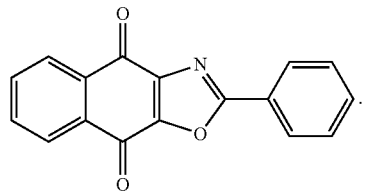

(043)

In some embodiments, the non-small cell lung cancer has T790M EGFR mutation. In some embodiments, the presence of the T790M EGFR mutation in the cancer is determined by performing an analysis of a sample obtained of the subject. In some embodiments, the sample is selected from the group consisting of blood, tumor tissue and urine. In some embodiments, the analysis of the sample comprises PCR-based assays, direct sequencing, primer extension reactions, electrophoresis, oligonucleotide ligation assays, hybridization assays, TaqMan assays, SNP genotyping assays, high resolution melting assays and/or microarray analysis. In some embodiments, the sample is analyzed using Cobas® EGFR Mutation.

Some aspects of the invention provide a method for treating epidermal growth factor receptor (EGFR)-mutant non-small cell lung cancer. The method comprises administering to a subject in need thereof a compound according to Formula I:

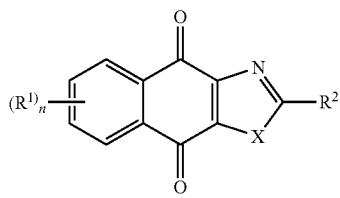

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^A$; $-C(=O)R^A$; $-C(=O)N(R^A)_2$; $-CO_2R^A$; $-CN$; $-SCN$; $-SR^A$; $-SOR^A$; $-SO_2R^A$; $-NO_2$; $-N_3$; $-N(R^A)_2$; $-NHC(=O)R^A$; $-NR^AC(=O)N(R_A)_2$; $-OC(=O)OR^A$; $-OC(=O)R^A$; $-OC(=O)N(R^A)_2$; $-NR^AC(=O)OR^A$; or $-C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^B$; $-C(=O)R^B$; $-C=(O)N(R^B)_2$; $-CO_2R^B$; $-CN$; $-SCN$; $-SR^B$; $-SOR^B$; $-SO_2R^B$; $-NO_2$; $-N_3$; $-N(R^B)_2$; $-NHC(=O)R^B$; $-NR^BC(=O)N(R^B)_2$; $-OC(=O)OR^B$; $-OC(=O)R^B$; $-OC(=O)N(R^B)_2$; $-NR^BC(=O)OR^B$; or $-C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the EGFR-mutant non-small cell lung cancer.

In some embodiments, the compound according to Formula I is the compound of any one of Formula A, An-1, An-2, An-3, Ac-1, Ac-2, and Ac-3 described herein. In some embodiments, the compound according to Formula I is:

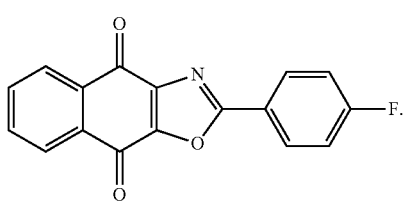

(527)

In some embodiments, the compound according to Formula I is:

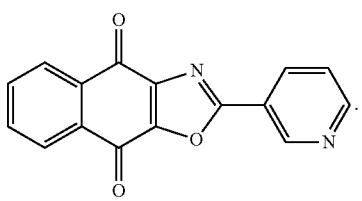

(019A)

In some embodiments, the compound according to Formula I is:

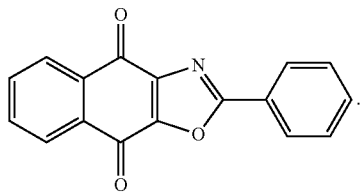

(043)

In some embodiments, the EGFR mutant non-small cell lung cancer has one or more EGFR activating mutations. In some embodiments, the activating mutation is selected from the group consisting of L858R, L861Q, G719S, del 19 and exon 20 insertions. In some embodiments, the EGFR mutant non-small cell lung cancer has one or more EGFR resistance mutations. In some embodiments, the resistance mutation is T790M.

Some aspects of the invention provide a pharmaceutical composition comprising the compound of any one of Formula A, An-1, An-2, An-3, Ac-1, Ac-2, and Ac-3 described herein and a pharmaceutically acceptable carrier.

Some aspects of the invention provide a method for treating cyclin D1- and/or USP2a-dependent prostate cancer. The method comprises administering to a subject in need thereof a compound according to Formula I:

Formula I

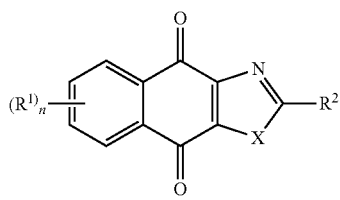

wherein
X is O, S, or NR³;
n is 0, 1, 2, 3, or 4;
each occurrence of R¹ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$_A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R² is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R³ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof,
in an amount effective to treat the cyclin D1- and/or USP2a-dependent prostate cancer.

In some embodiments, the compound according to Formula I is the compound of any one of Formula A, An-1, An-2, An-3, Ac-1, Ac-2, and Ac-3 described herein. In some embodiments, the compound according to Formula I is:

(527)

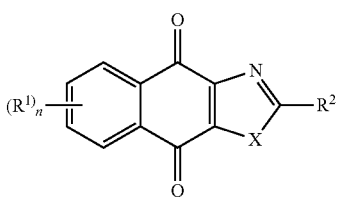

In some embodiments, the compound according to Formula I is:

(019A)

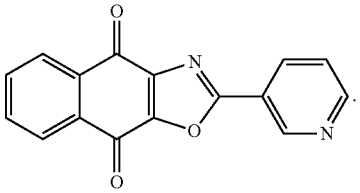

In some embodiments, the compound according to Formula I is:

(043)

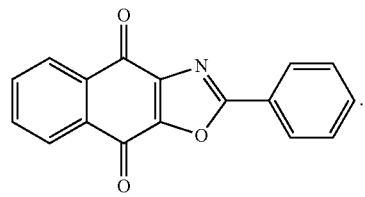

Some aspects of the invention provide a method for treating cyclin D1- and/or USP2a-dependent prostate cancer. The method comprises: identifying a subject having a cyclin D1- and/or USP2a-dependent prostate cancer; and administering to the subject a compound according to Formula I:

Formula I (R¹)$_n$ structure with R² wherein
X is O, S, or NR³;
n is 0, 1, 2, 3, or 4;
each occurrence of R¹ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$_A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R² is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the cyclin D1- and/or USP2a-dependent prostate cancer.

In some embodiments, the compound according to Formula I is the compound of any one of Formula A, An-1, An-2, An-3, Ac-1, Ac-2, and Ac-3 described herein. In some embodiments, the compound according to Formula I is:

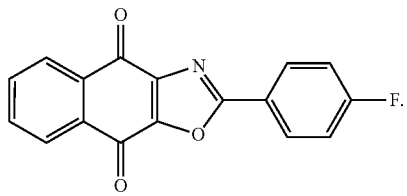

(527)

In some embodiments, the compound according to Formula I is:

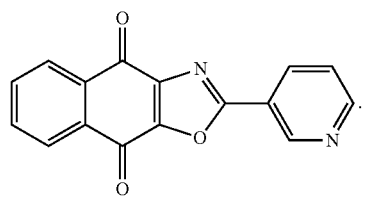

(019A)

In some embodiments, the compound according to Formula I is:

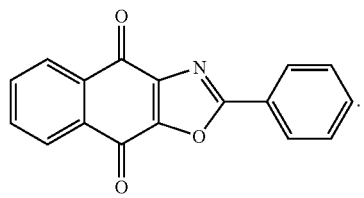

(043)

In some embodiments, the subject is identified as having the cyclin D1- and/or USP2a-dependent prostate cancer by performing an analysis of a sample obtained of the subject. In some embodiments, the sample is selected from the group consisting of blood, urine, ejaculate, and tumor tissue. In some embodiments, the analysis of the sample comprises determining the expression of USP2 and/or cyclin D1. In some embodiments, the expression of USP2 and/or cyclin D1 is determined by immunohistochemistry. In some embodiments, the expression of USP2 and/or cyclin D1 is determined by microarray analysis.

Some aspects of the invention provide a method for treating androgen receptor (AR)- and/or USP12-dependent prostate cancer. The method comprises administering to a subject in need thereof a compound according to Formula I:

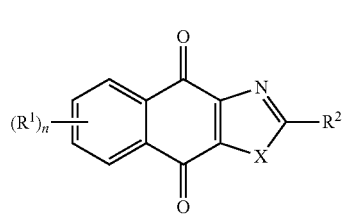

Formula I wherein
X is O, S, or NR$^3$;
n is 0, 1, 2, 3, or 4;
each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$_A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the androgen receptor (AR)- and/or USP12-dependent prostate cancer.

In some embodiments, the compound according to Formula I is the compound of any one of Formula A, An-1, An-2, An-3, Ac-1, Ac-2, and Ac-3 described herein. In some embodiments, the compound according to Formula I is:

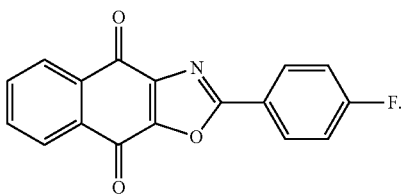
(527)

In some embodiments, the compound according to Formula I is:

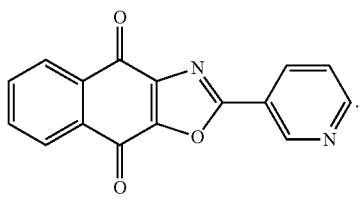
(019A)

In some embodiments, the compound according to Formula I is:

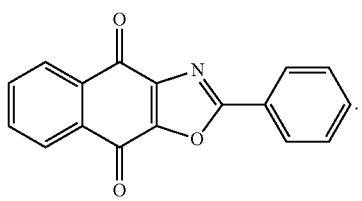
(043)

Some aspects of the invention provide a method for treating androgen receptor (AR)- and/or USP12-dependent prostate cancer. The method comprises: identifying a subject having a androgen receptor (AR)- and/or USP12-dependent prostate cancer; and administering to the subject a compound according to Formula I:

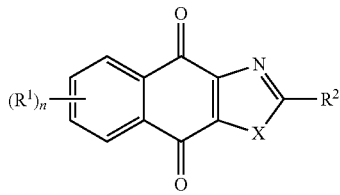
Formula I wherein
  X is O, S, or NR$^3$;
  n is 0, 1, 2, 3, or 4;
  each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$_A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof,
in an amount effective to treat the androgen receptor (AR)- and/or USP12-dependent prostate cancer.

In some embodiments, the compound according to Formula I is the compound of any one of Formula A, An-1, An-2, An-3, Ac-1, Ac-2, and Ac-3 described herein. In some embodiments, the compound according to Formula I is:

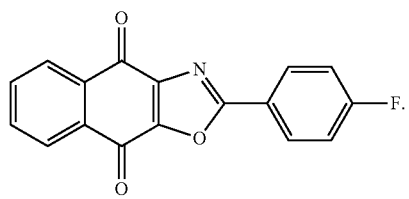
(527)

In some embodiments, the compound according to Formula I is:

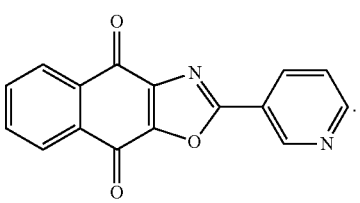
(019A)

In some embodiments, the compound according to Formula I is:

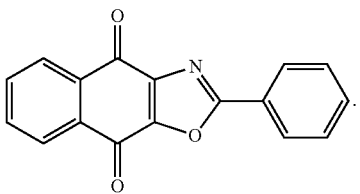
(043)

In some embodiments, the subject is identified as having the androgen receptor (AR)- and/or USP12-dependent prostate cancer by performing an analysis of a sample obtained of the subject. In some embodiments, the sample is selected from the group consisting of blood, urine, ejaculate, and tumor tissue. In some embodiments, the analysis of the sample comprises determining the expression of AR and/or USP12. In some embodiments, the expression of AR and/or USP12 is determined by immunohistochemistry. In some embodiments, the expression of AR and/or USP12 is determined by microarray analysis.

Some aspects of the invention provide a method for treating prostate cancer resistant to androgen receptor (AR) inhibitor therapy. The method comprises administering to a subject in need thereof a compound according to Formula I:

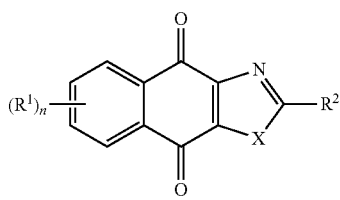
Formula I wherein
X is O, S, or NR$^3$;
n is 0, 1, 2, 3, or 4;
each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$^A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof,
in an amount effective to treat the prostate cancer resistant to androgen receptor (AR) inhibitor therapy.

In some embodiments, the compound according to Formula I is the compound of any one of Formula A, An-1, An-2, An-3, Ac-1, Ac-2, and Ac-3 described herein. In some embodiments, the compound according to Formula I is:

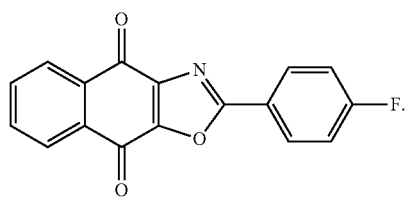
(527)

In some embodiments, the compound according to Formula I is:

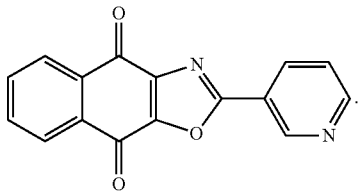
(019A)

In some embodiments, the compound according to Formula I is:

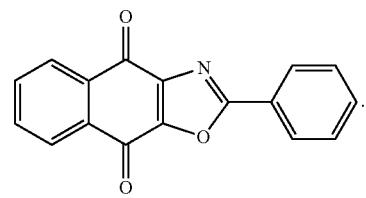
(043)

DEFINITIONS

Chemical Definitions

Figure 1:
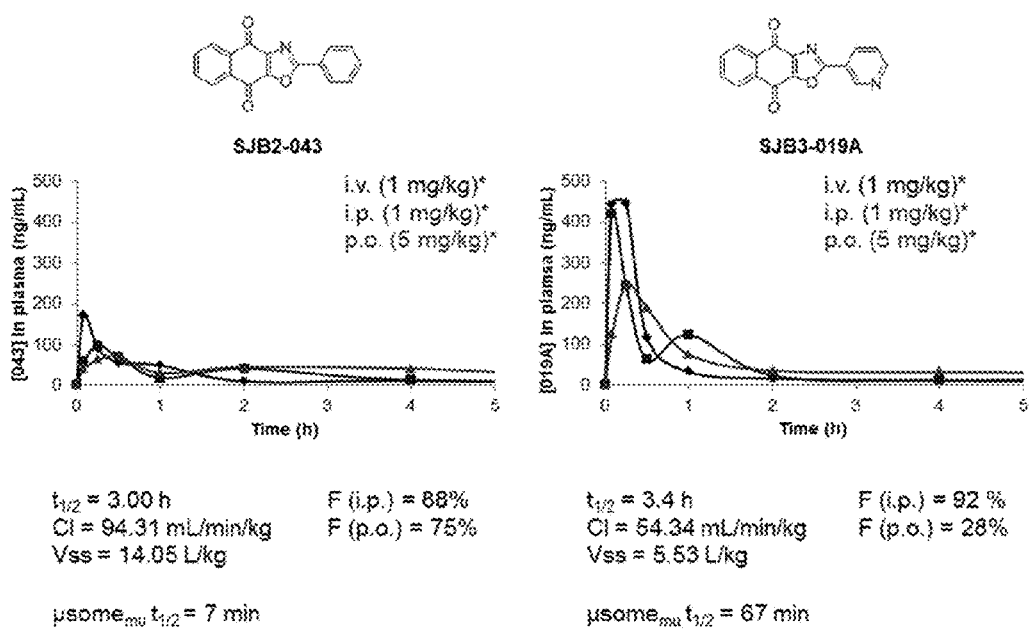
FIG. 1 shows pharmacokinetic data which demonstrates that inhibitory serum concentrations of 019A can be achieved in mice by IV, IP, or oral (PO) administration of drugs.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$— cyclopropyl, vinyl, allyl, n-butyl, sec-butyl, isobutyl, tert-butyl, cyclobutyl, —$CH_2$— cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —OC(=O) R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N (R$^{bb}$)$_2$, —C(=NR$^{bb}$)R$^{aa}$, —C(=NR$^{bb}$)OR$^{aa}$, —OC (=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC (=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP (=O)(R$^{aa}$)$_2$, —OP(=O)(OR$^{cc}$)$_2$, —P(=O)$_2$N(R$^{bb}$)$_2$, —OP (=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=)R$^{aa}$, =NNR$^{bb}$C (=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —C(=S)SR$^{ee}$, —SC(=S)SR$^{ee}$, S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S) SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl), —N(C$_{1-6}$ alkyl)$_3$$^+$X$^-$, —NH(C$_{1-6}$ alkyl)$_2$$^+$X$^-$, —NH$_2$(C$_{1-6}$ alkyl) $^+$X$^-$, —NH$_3$ $^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C (=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methan-sulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1- sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolylN-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(O)$R^{aa}$, —$SO_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The invention is not intended to be limited in any manner by the above exemplary listing of substituents.

OTHER DEFINITIONS

Ubiquitin is a 76 amino acid protein that can be covalently attached to other proteins, targeting them for degradation or regulating their function. Ubiquitin is covalently attached to other proteins by a ubiquitin transferase enzyme, and it is released from a ubiquitinated protein by a deubiquitinating enzyme.

Ubiquitination and deubiquitination regulate a number of essential biological processes such as gene transcription, DNA replication, and DNA repair (Pickart et al. (2004) Biochim Biophys Acta 1695:55-72.) There are at least 95 putative deubiquitinating enzymes in humans (Nijman et al. (2005) Cell 123:773-86). This family of deubiquitinating enzymes is divided into five subfamilies, including the ubiquitin specific protease (USP) subfamily (58 members), the otubain protease (OTU) subfamily and the JAB1/MPN/Mov34 metalloprotease (JAMM) subfamily (14 members each), the Josephine domain protease (MJD) subfamily (5 members), and the ubiquitin C-terminal hydrolase (UCH) subfamily (4 members). The exact biological function for many of these enzymes is currently unknown. However, for those enzymes whose function has been uncovered, it has become apparent that regulation of their activities is essential for integrity of the pathways they regulate.

As used herein, the USP8 gene is disclosed as Entrez Gene ID No. 9101 and the USP8 protein is disclosed as UniProtKB ID No. P40818. USP8 is implicated in ubiquitin remodeling, down regulation of epidermal growth factor receptor (EGFR), clathrin-mediated internalization, endosomal sorting, the control of receptor tyrosine kinases, and it may be involved in the patho-physiology of breast cancer (Mizuno, E., T. Lura et al. 'Regulation of epidermal growth factor receptor down-regulation by UBPY-mediated deubiquitination at endosomes' Molecular Biology of the Cell vol. 16, no. 11, 2005, pages 5163-5174; Avvakumov, Walker et al. 'Amino-terminal dimerization, NRDP1-rhodanese interaction, and inhibited catalytic domain conformation of the ubiquitin-specific protease 8 Journal of Biological Chemistry vol. 281, no. 49, 2006, pages 38061-38070; Niendorf, Oksche et al. 'Essential role of ubiquitin-specific protease 8 for receptor tyrosine kinase stability and endocytic trafficking in vivo' Molecular and Cellular Biology, no. 13, 2007, pages 5029-5039).

Ubiquitin-specific Protease 2a (USP2a) is a member of the USP family that was originally identified as an inducible USP enzyme in rat testis. As used herein, the USP2 gene is disclosed as Entrez Gene ID No. 9099 and the USP2 protein is disclosed as UniProtKB ID No. 075604. Recent data indicate that aberrant USP2a activity is associated with the formation and progression of human tumors and that USP2a is overexpressed in >40% of prostate tumors (Priolo C., Tang D., Brahamandan M., Benassi B., Sicinska E., Ogino S., Farsetti A., Porrello A., Finn S., Zimmermann J., Febbo P., Loda M. (2006) Cancer Res. 66, 8625-8632). In addition, USP2a is a bona fide oncogene as demonstrated by its ability to transform NIH-3T3 cells (Priolo C., Tang D., Brahamandan M., Benassi B., Sicinska E., Ogino S., Farsetti A., Porrello A., Finn S., Zimmermann J., Febbo P., Loda M. (2006) Cancer Res. 66, 8625-8632).

As used herein, the Ubiquitin-specific Protease (USP12) gene is disclosed as Entrez Gene ID No. 219333 and the USP12 protein is disclosed as UniProtKB ID No. 075317. Recently, USP12 was identified as a novel positive regulator of androgen receptor (AR) (Burska et al. J Biol Chem. 2013 Nov. 8; 288(45):32641-50). Usp12, in complex with Uaf-1 and WDR20, deubiquitinates the AR to enhance receptor stability and transcriptional activity. Thus, Usp12 acts in a pro-proliferative manner by stabilizing AR and enhancing its cellular function (Burska et al. J Biol Chem. 2013 Nov. 8; 288(45):32641-50).

As used herein, an "inhibitor of USP8", "inhibitor of USP2a" or an "inhibitor of USP12" refers to an agent that decreases deubiquitinase activity of USP8, USP2a or USP12 respectively. As used herein, the terms "deubiquitinase activity of USP8", "deubiquitinase activity of USP2a", or "deubiquitinase activity of USP12" and, equivalently, "USP8 activity", "USP2a activity" or "USP12 activity", refers to the action of USP8, USP2a or USP12 to remove ubiquitin from a ubiquitinated substrate. Deubiquitinase activity can be measured in vitro or in vivo, and it can be measured directly or indirectly. Deubiquitinase activity can be measured by a number of assays known in the art (see, for example, EP 2580344, U.S. Pat. No. 8,518,660). A USP8, USP2a, or USP12 polypeptide is deemed to have deubiquitinase activity where the level of deubiquitinated substrate in the presence of USP8, USP2a or USp12 is at least 10% greater than the level of deubiquitinated substrate from a control sample (e.g., sample from the same tissue, or a separate aliquot of a cellular sample) in the absence of USP8, USP2a or USP12 respectively. Alternatively a USP8, USP2a or USp12 polypeptide is deemed to have deubiquitinase activity where the level of ubiquitinated substrate is decreased by at least 10% in the presence of USP8, USP2a or USp12 relative to a control sample in the absence of USP8, USP2a or USp12 respectively. In one embodiment a decrease in USP8, USP2a or USp12 deubiquitinase activity in response to an agent as used herein refers to any detectable decrease in the production of a deubiquitinated substrate in the presence of the agent relative to in the absence of the agent, such as a 0.5% decrease, a 1% decrease, 2%, 3-5%, 5-10%, 10-20%, 20-40%, 40-80%, 90%, or 100% decrease in the production of a deubiquitinated substrate.

As used herein, a "small molecule" refers to an organic molecule of molecular weight of less than 1500 Daltons.

As used herein, a "pharmaceutically acceptable carrier" refers to one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficacy.

As used herein, a "pharmaceutically acceptable salt" refers to an acid or base form of a compound, usually in combination with a counter ion, that is suitable for use in pharmacy. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Pharmaceutically acceptable salts are well known in the art and are the subject of numerous reviews and monographs such as P. H. Stahl and C. G. Wermuth, editors, *Handbook of Pharmaceutical Salts: Properties, Selection and Use*, Weinheim/Zürich:Wiley-VCHNHCA, 2002.

DETAILED DESCRIPTION OF THE INVENTION

The present invention is based, at least in part, on the discovery that the compounds of the invention degrade activated EGF-Receptor (EGFR), Cyclin D1, and Androgen Receptor (AR). In some embodiments, the compounds of the invention also strongly inhibit USP8 and USP2a and USP12. Thus, the invention provides certain small molecule inhibitors of deubiquitinating enzyme activity as well as compositions comprising these inhibitors.

USP8 is recognized in the art as a therapeutic target for gefitinib-resistant and -sensitive non-small cell lung cancer (NSCLC) (Byun et al. Clin Cancer Res. 2013 Jul. 15; 19(14):3894-904). The inventors of this application have discovered that the compounds described herein not only inhibit USP8, but can also degrade EGFR and reduce the viability of EGFR mutant NSCLC cell lines. Thus, some aspects of the invention provide methods for treating non-small cell lung cancer (NSCLC) having EGFR mutations based on the ability to inhibit USP8 activity.

The isopeptidase USP2a protects human prostate cancer from apoptosis (Priolo et al. Cancer Res. 2006 Sep. 1; 66(17):8625-32) and therapeutic targeting of this isopeptidase and its substrates (which includes Cyclin D1) represents an important therapeutic strategy to treat prostate cancer. The inventors of this application have discovered that the compounds described herein inhibit USP2a function by degrading cyclin D1 and reduce the viability of prostate cancer cells. Thus, some aspects of the invention provide methods for treating cyclin D1- and USP2a-dependent prostate cancer.

USP12 was recently identified as a novel positive regulator of androgen receptor (AR) (Burska et al. J Biol Chem. 2013 Nov. 8; 288(45):32641-50). Usp12, in complex with Uaf-1 and WDR20, deubiquitinates the AR to enhance receptor stability and transcriptional activity. Thus, Usp12 acts in a pro-proliferative manner by stabilizing AR and enhancing its cellular function (Burska et al. J Biol Chem. 2013 Nov. 8; 288(45):32641-50). Some aspects of the invention provide methods for treating AR- and USP12-dependent prostate cancer.

Compounds

In certain embodiments, the compound of the invention or for use in the invention is of Formula A:

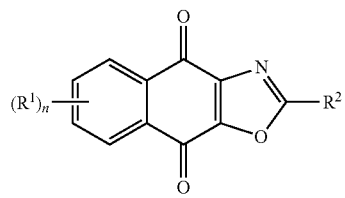

Formula A or pharmaceutically acceptable salts, solvates, hydrates, polymorphs, co-crystals, tautomers, stereoisomers, isotopically labeled derivatives, and prodrugs thereof, wherein n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{A1}$; —$C(=O)R^{A1}$; —$C(=O)N(R^{A1})_2$; —$CO_2R^{A1}$; —CN; —SCN; —$SR^{A1}$; —$SOR^{A1}$; —$SO_2R^{A1}$; —$NO_2$; —$N_3$; —$N(R^{A1})_2$; —$NHC(=O)R^{A1}$; —$NR^{A1}C(=O)N(R^{A1})_2$; —$OC(=O)OR^{A1}$; —$OC(=O)R^{A1}$; —$OC(=O)N(R^{A1})_2$; —$NR^{A1}C(=O)OR^{A1}$; or —$C(R^{A1})_3$;

each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2}$, —$N(R^{A2})_2$, —$SR^{A2}$, —CN, —SCN, —$C(=NR^{A2})R^{A2}$, —$C(=NR^{A2})OR^{A2}$, —$C(=NR^{A2})N(R^{A2})_2$, —$C(=O)R^{A2}$, —$C(=O)OR^{A2}$, —$C(=O)N(R^{A2})_2$, —$NO_2$, —$NR^{A2}C(=O)R^{A2}$, —$NR^{A2}C(=O)OR^{A2}$, —$NR^{A2}C(=O)N(R^{A2})_2$, —$OC(=O)R^{A2}$, —$OC(=O)OR^{A2}$, or —$OC(=O)N(R^{A2})_2$;

each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring $R^2$ is cyclic or acyclic, branched or unbranched aliphatic; cyclic or acyclic, branched or unbranched heteroaliphatic; aryl; or heteroaryl; optionally substituted with m instances of $R^4$;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —$C(=NR^B)R^B$, —$C(=NR^B)OR^B$, —$C(=NR^B)N(R^B)_2$, —$C(=O)R^B$, —$C(=O)OR^B$, —$C(=O)N(R^B)_2$, —$NO_2$, —$NR^BC(=O)R^B$, —$NR^BC(=O)OR^B$, —$NR^BC(=O)N(R^B)_2$, —$OC(=O)R^B$, —$OC(=O)OR^B$, or —$OC(=O)N(R^B)_2$;

each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring; and m is 0, 1, 2, 3, 4, or 5.

In certain embodiments, the compound of the invention or for use in the invention is of Formula An-1:

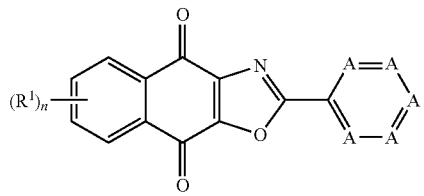

Formula An-1 or pharmaceutically acceptable salts, solvates, hydrates, polymorphs, co-crystals, tautomers, stereoisomers, isotopically labeled derivatives, and prodrugs thereof, wherein A is N or C—$R^4$, wherein no more than two A groups can be N;

n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{A1}$; —$C(=O)R^{A1}$; —$C(=O)N(R^{A1})_2$; —$CO_2R^{A1}$; —CN; —SCN; —$SR^{A1}$; —$SOR^{A1}$; —$SO_2R^{A1}$; —$NO_2$; —$N_3$; —$N(R^{A1})_2$; —$NHC(=O)R^{A1}$; —$NR^{A1}C(=O)N(R^{A1})_2$; —$OC(=O)OR^{A1}$; —$OC(=O)R^{A1}$; —$OC(=O)N(R^{A1})_2$; —$NR^{A1}C(=O)OR^{A1}$; or —$C(R^{A1})_3$;

each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2}$, —$N(R^{A2})_2$, —$SR^{A2}$, —CN, —SCN, —$C(=NR^{A2})R^{A2}$, —$C(=NR^{A2})OR^{A2}$, —$C(=NR^{A2})N(R^{A2})_2$, —$C(=O)R^{A2}$, —$C(=O)OR^{A2}$, —$C(=O)N(R^{A2})_2$, —$NO_2$, —$NR^{A2}C(=O)R^{A2}$, —$NR^{A2}C(=O)OR^{A2}$, —$NR^{A2}C(=O)N(R^{A2})_2$, —$OC(=O)R^{A2}$, —$OC(=O)OR^{A2}$, or —$OC(=O)N(R^{A2})_2$;

each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —$C(=NR^B)R^B$, —$C(=NR^B)OR^B$, —$C(=NR^B)N(R^B)_2$, —$C(=O)R^B$, —$C(=O)OR^B$, —$C(=O)N(R^B)_2$, —$NO_2$, —$NR^BC(=O)R^B$, —$NR^BC(=O)OR^B$, —$NR^BC(=O)N(R^B)_2$, —$OC(=O)R^B$, —$OC(=O)OR^B$, or —$OC(=O)N(R^B)_2$; and each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring.

In certain embodiments, the compound of the invention or for use in the invention is of Formula An-2:

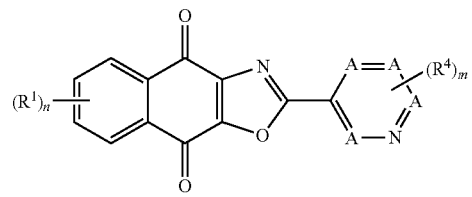

Formula An-2 or pharmaceutically acceptable salts, solvates, hydrates, polymorphs, co-crystals, tautomers, stereoisomers, isotopically labeled derivatives, and prodrugs thereof, wherein A, $R^1$, $R^4$, n, and m are defined herein.

In certain embodiments, the compound of the invention or for use in the invention is of Formula An-3:

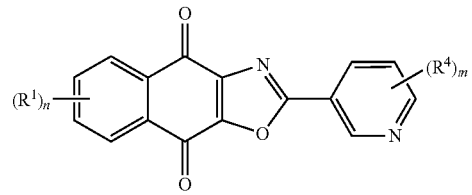

Formula An-3 or pharmaceutically acceptable salts, solvates, hydrates, polymorphs, co-crystals, tautomers, stereoisomers, isotopically labeled derivatives, and prodrugs thereof, wherein $R^1$, $R^4$, n, and m are defined herein.

In certain embodiments, the compound of the invention or for use in the invention is of Formula Ac-1:

Formula Ac-1

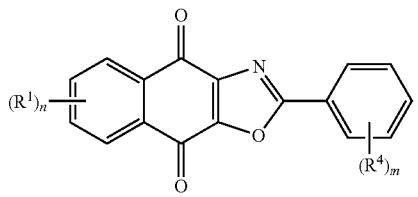

or pharmaceutically acceptable salts, solvates, hydrates, polymorphs, co-crystals, tautomers, stereoisomers, isotopically labeled derivatives, and prodrugs thereof, wherein n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{A1}$; —$C(=O)R^{A1}$; —$C(=O)N(R^{A1})_2$; —$CO_2R^{A1}$; —CN; —SCN; —$SR^{A1}$; —$SOR^{A1}$; —$SO_2R^{A1}$; —$NO_2$; —$N_3$; —$N(R^{A1})_2$; —$NHC(=O)R^{A1}$; —$NR(R^{A1})_2$; —$OC(=O)OR^{A1}$; —$OC(=O)R^{A1}$; —$OC(=O)N(R^{A1})_2$; —$NR^{A1}C(=O)OR^{A1}$; or —$C(R^{A1})_3$;

each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2}$, —$N(R^{A2})_2$, —$SR^{A2}$, —CN, —SCN, —$C(=NR^{A2})R^{A2}$, —$C(=NR^{A2})OR^{A2}$, —$C(=NR^{A2})N(R^{A2})_2$, —$C(=O)R^{A2}$, —$C(=O)OR^{A2}$, —$C(=O)N(R^{A2})_2$, —$NO_2$, —$NR^{A2}C(=O)R^{A2}$, —$NR^{A2}C(=O)OR^{A2}$, —$NR^{A2}C(=O)N(R^{A2})_2$, —$OC(=O)R^{A2}$, —$OC(=O)OR^{A2}$, or —$OC(=O)N(R^{A2})_2$;

each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —$C(=NR^B)R^B$, —$C(=NR^B)OR^B$, —$C(=NR^B)N(R^B)_2$, —$C(=O)R^B$, —$C(=O)OR^B$, —$C(=O)N(R^B)_2$, —$NO_2$, —$NR^BC(=O)R^B$, —$NR^BC(=O)OR^B$, —$NR^BC(=O)N(R^B)_2$, —$OC(=O)R^B$, —$OC(=O)OR^B$, or —$OC(=O)N(R^B)_2$;

each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring; and m is 0, 1, 2, 3, 4, or 5.

In certain embodiments, the compound of the invention or for use in the invention is of Formula Ac-2:

Formula Ac-2

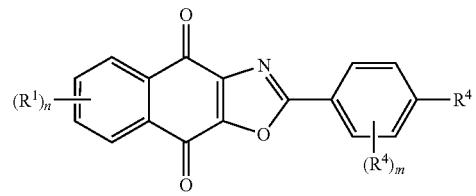

or pharmaceutically acceptable salts, solvates, hydrates, polymorphs, co-crystals, tautomers, stereoisomers, isotopically labeled derivatives, and prodrugs thereof, wherein $R^1$, $R^4$, n, and m are defined herein.

In certain embodiments, the compound of the invention or for use in the invention is of Formula Ac-3:

Formula Ac-3

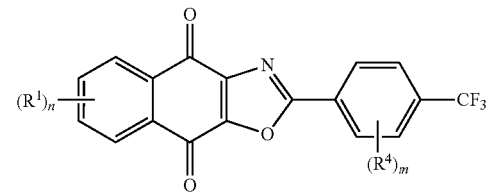

or pharmaceutically acceptable salts, solvates, hydrates, polymorphs, co-crystals, tautomers, stereoisomers, isotopically labeled derivatives, and prodrugs thereof, wherein $R^1$, $R^4$, n, and m are defined herein.

In certain embodiments, a compound of Formula A is of the formula:

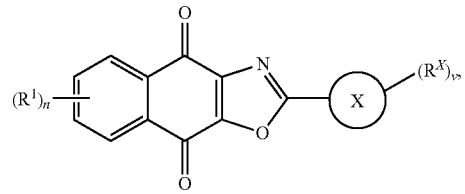

or a pharmaceutically acceptable salt thereof, wherein:

Ring X is a substituted or unsubstituted pyridyl ring;

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —OC (=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and v is 0, 1, 2, 3, or 4.

In certain embodiments, a compound of Formula A is of one of the following formulae:

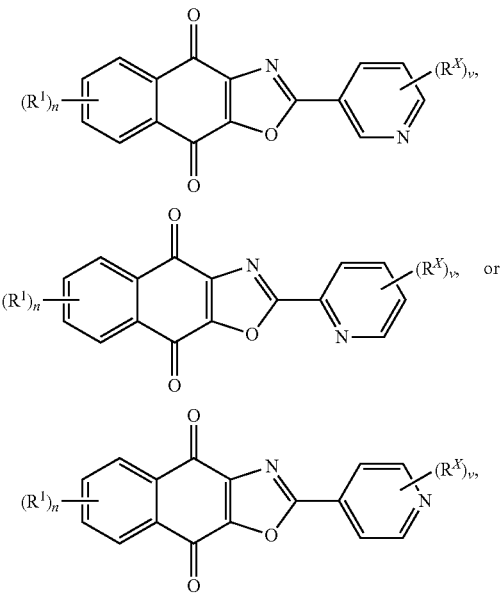

or a pharmaceutically acceptable salt thereof.

In certain embodiments, the compound of the invention or for use in the invention is selected from the group consisting of:

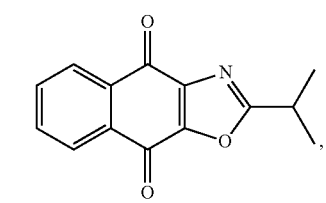
(1)

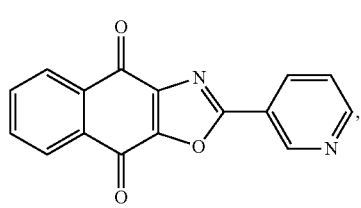
(2)

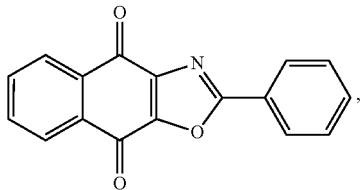
(3)

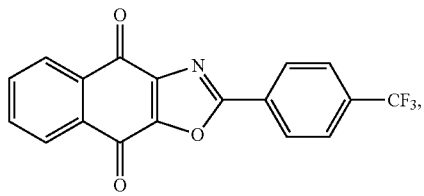
(4)

and

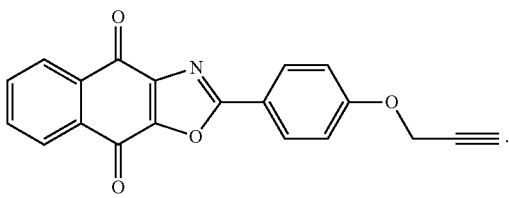
(5)

or pharmaceutically acceptable salts, solvates, hydrates, polymorphs, co-crystals, tautomers, stereoisomers, isotopically labeled derivatives, and prodrugs thereof.

R$^1$, R$^{41}$, R$^{42}$, and n

As is generally defined herein, each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^{41}$; —C(=O)R$^{41}$; —C(=O)N(R$^{41}$)$_2$; —CO$_2$R$^{41}$; —CN; —SCN; —SR$^{41}$; —SOR$^{41}$; —SO$_2$R$^{41}$; —NO$_2$; —N$_3$; —N(R$^{41}$)$_2$; —NHC(=O)R$^{41}$; —NR$^{41}$C(=O)N(R$^{41}$)$_2$; —OC(=O)OR$^{41}$; —OC(=O)R$^{41}$; —OC(=O)N(R$^{41}$)$_2$; —NR$^{41}$C(=O)OR$^{41}$; or —C(R$^{41}$)$_3$. As is generally defined herein, each occurrence of R$^{41}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{42}$, —N(R$^{42}$)$_2$, —SR$^{42}$, —CN, —SCN, —C(=NR$^{42}$)R$^{42}$, —C(=NR$^{42}$)OR$^{42}$, —C(=NR$^{42}$)N(R$^{42}$)$_2$, —C(=O)R$^{42}$, —C(=O)OR$^{42}$, —C(=O)N(R$^{42}$)$_2$, —NO$_2$, —NR$^{42}$C(=O)R$^{42}$, —NR$^{42}$C(=O)OR$^{42}$, —NR$^{42}$C(=O)N(R$^{42}$)$_2$, —OC(=O)R$^{42}$, —OC(=O)OR$^{42}$, or —OC(=O)N(R$^{42}$)$_2$. As is generally defined herein, each instance of R$^{42}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring. As is generally defined herein, n is 0, 1, 2, 3, Or 4.

In certain embodiments, at least one $R^1$ group is halogen. In certain embodiments, at least one $R^1$ group is fluorine. In certain embodiments, at least one $R^1$ group is chlorine. In certain embodiments, at least two $R^1$ groups are halogen. In certain embodiments, at least two $R^1$ groups are fluorine. In certain embodiments, at least two $R^1$ groups are chlorine. In certain embodiments, one $R^1$ group is fluorine; and one $R^1$ group is chlorine.

In certain embodiments, $R^1$ is substituted or unsubstituted cycloalkyl. In certain embodiments, $R^1$ is substituted or unsubstituted 3-6 membered cycloalkyl, e.g., cyclopropyl, cyclobutyl, cyclopentyl, or cyclohexyl. In certain embodiments, $R^1$ is 3-6 membered cycloalkyl substituted with 1, 2, 3, 4, or 5 instances of $R^{A1}$, wherein each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A2}$, $-N(R^{A2})_2$, $-SR^{A2}$, $-CN$, $-SCN$, $-C(=NR^{A2})R^{A2}$, $-C(=NR^{A2})OR^{A2}$, $-C(=NR^{A2})N(R^{A2})_2$, $-C(=O)R^{A2}$, $-C(=O)OR^{A2}$, $-C(=O)N(R^{A2})_2$, $-NO_2$, $-NR^{A2}C(=O)R^{A2}$, $-NR^{A2}C(=O)OR^{A2}$, $-NR^{A2}C(=O)N(R^{A2})_2$, $-OC(=O)R^{A2}$, $-OC(=O)OR^{A2}$, or $-OC(=O)N(R^{A2})_2$ and each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring.

In certain embodiments, at least one $R^1$ is substituted or unsubstituted cycloalkyl. In certain embodiments, at least one $R^1$ is substituted or unsubstituted 3-6 membered cycloalkyl. In certain embodiments, at least one $R^1$ is substituted 3-6 membered cycloalkyl. In certain embodiments, at least one $R^1$ is unsubstituted 3-6 membered cycloalkyl. In certain embodiments, at least one $R^1$ is substituted cyclopropyl. In certain embodiments, at least one $R^1$ is substituted cyclobutyl. In certain embodiments, at least one $R^1$ is substituted cyclopentyl. In certain embodiments, at least one $R^1$ is substituted cyclohexyl. In certain embodiments, at least one $R^1$ is unsubstituted cyclopropyl. In certain embodiments, at least one $R^1$ is unsubstituted cyclobutyl. In certain embodiments, at least one $R^1$ is unsubstituted cyclopentyl. In certain embodiments, at least one $R^1$ is unsubstituted cyclohexyl.

In certain embodiments, at least one $R^1$ is substituted or unsubstituted, branched or unbranched aliphatic. In certain embodiments, at least one $R^1$ is substituted or unsubstituted, branched or unbranched $C_{1-6}$ aliphatic. In certain embodiments, at least one $R^1$ is substituted or unsubstituted, branched or unbranched $C_{1-3}$ aliphatic. In certain embodiments, at least one $R^1$ is unsubstituted, branched or unbranched $C_{1-6}$ aliphatic. In certain embodiments, at least one $R^1$ is unsubstituted, branched or unbranched $C_{1-3}$ aliphatic. In certain embodiments, at least one $R^1$ is substituted methyl. In certain embodiments, at least one $R^1$ is substituted ethyl. In certain embodiments, at least one $R^1$ is unsubstituted methyl. In certain embodiments, at least one $R^1$ is unsubstituted ethyl.

In certain embodiments, $R^1$ is substituted or unsubstituted alkenyl, e.g., vinyl, allyl, propenyl, or butenyl. In certain embodiments, $R^1$ is substituted or unsubstituted alkynyl, e.g., propargyl, propynyl, or butynyl.

In certain embodiments, at least one $R^1$ is $C_{1-6}$ haloalkyl. In certain embodiments, at least one $R^1$ is $-CF_3$. In certain embodiments, at least one $R^1$ is $-CF_2H$. In certain embodiments, at least one $R^1$ is $-CH_2CF_3$. In certain embodiments, at least one $R^1$ is $-CHF_2$. In certain embodiments, at least one $R^1$ is $-CH_2F$. In certain embodiments, at least one $R^1$ is $-CF_2CH_3$. In certain embodiments, at least one $R^1$ is $-CF_2CF_3$.

In certain embodiments, $R^1$ is substituted or unsubstituted heterocyclyl. In certain embodiments, $R^1$ is substituted or unsubstituted 3-6 membered heterocyclyl, e.g., oxetanyl, tetrahydrofuranyl, pyranyl, azetidinyl, pyrrolidinyl, or piperidinyl. In certain embodiments, $R^1$ is 3-6 membered heterocyclyl substituted with 1, 2, 3, 4, or 5 instances of $R^{A1}$, wherein each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A2}$, $-N(R^{A2})_2$, $-SR^{A2}$, $-CN$, $-SCN$, $-C(=NR^{A2})R^{A2}$, $-C(=NR^{A2})OR^{A2}$, $-C(=NR^{A2})N(R^{A2})_2$, $-C(=O)R^{A2}$, $-C(=O)OR^{A2}$, $-C(=O)N(R^{A2})_2$, $-NO_2$, $-NR^{A2}C(=O)R^{A2}$, $-NR^{A2}C(=O)OR^{A2}$, $-NR^{A2}C(=O)N(R^{A2})_2$, $-OC(=O)R^{A2}$, $-OC(=O)OR^{A2}$, or $-OC(=O)N(R^{A2})_2$ and each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring.

In certain embodiments, at least one $R^1$ is substituted or unsubstituted heterocyclyl. In certain embodiments, at least one $R^1$ is substituted or unsubstituted 3-6 membered heterocyclyl. In certain embodiments, at least one $R^1$ is substituted 3-6 membered heterocyclyl. In certain embodiments, at least one $R^1$ is unsubstituted 3-6 membered heterocyclyl. In certain embodiments, at least one $R^1$ is substituted or unsubstituted azetidine. In certain embodiments, at least one $R^1$ is substituted or unsubstituted oxetane. In certain embodiments, at least one $R^1$ is substituted or unsubstituted pyrrolidine. In certain embodiments, at least one $R^1$ is substituted or unsubstituted tetrahydrofuran. In certain embodiments, at least one $R^1$ is substituted or unsubstituted piperidine. In certain embodiments, at least one $R^1$ is substituted or unsubstituted piperazine. In certain embodiments, at least one $R^1$ is substituted or unsubstituted morpholine. In certain embodiments, at least one $R^1$ is substituted or unsubstituted pyran. In certain embodiments, at least one $R^1$ is substituted or unsubstituted dioxane.

In certain embodiments, $R^1$ is substituted or unsubstituted aryl. In certain embodiments, $R^1$ is substituted or unsubstituted phenyl. In certain embodiments, $R^1$ is phenyl substituted with 1, 2, 3, 4, or 5 instances of $R^{A1}$, wherein each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A2}$, $-N(R^{A2})_2$, $-SR^{A2}$, $-CN$, $-SCN$, $-C(=NR^{A2})R^{A2}$, $-C(=NR^{A2})OR^{A2}$, $-C(=NR^{A2})N(R^{A2})_2$, $-C(=O)R^{A2}$, $-C(=O)OR^{A2}$, $-C(=O)N(R^{A2})_2$, $-NO_2$, $-NR^{A2}C(=O)R^{A2}$, $-NR^{A2}C(=O)OR^{A2}$, $-NR^{A2}C(=O)N(R^{A2})_2$, $-OC(=O)R^{A2}$, $-OC(=O)OR^{A2}$, or $-OC(=O)N(R^{A2})_2$ and each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring.

In certain embodiments, $R^1$ is substituted or unsubstituted heteroaryl. In certain embodiments, $R^1$ is substituted or unsubstituted 5-6 membered heteroaryl, e.g., pyrazolyl, imidazolyl, thiazolyl, oxazolyl, isothiazolyl, isoxazolyl, triazolyl, pyridinyl, pyrazinyl, pyrimidinyl, or pyridizinyl. In certain embodiments, $R^1$ is 5-6 membered heteroaryl substituted with 1, 2, 3, 4, or 5 instances of $R^{A1}$, wherein each instance of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A2}$, $-N(R^{A2})_2$, $-SR^{A2}$, $-CN$, $-SCN$, $-C(=NR^{A2})R^{A2}$, $-C(=NR^{A2})OR^{A2}$, $-C(=NR^{A2})N(R^{A2})_2$, $-C(=O)R^{A2}$, $-C(=O)OR^{A2}$, $-C(=O)N(R^{A2})_2$, $-NO_2$, $-NR^{A2}C(=O)R^{A2}$, $-NR^{A2}C(=O)OR^{A2}$, $-NR^{A2}C(=O)N(R^{A2})_2$, $-OC(=O)R^{A2}$, $-OC(=O)OR^{A2}$, or $-OC(=O)N(R^{A2})_2$ and each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring.

In certain embodiments, n is 0. In certain embodiments, n is 1. In certain embodiments, n is 2. In certain embodiments, n is 3. In certain embodiments, n is 4. In certain embodiments, n is not 0. In certain embodiments, n is not 1. In certain embodiments, n is not 2. In certain embodiments, n is not 3. In certain embodiments, n is not 4.

In certain embodiments, n is 1 and a compound of Formula A is

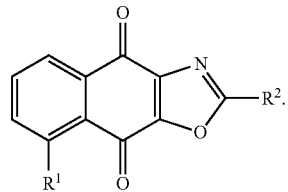

In certain embodiments, n is 1 and a compound of Formula A is

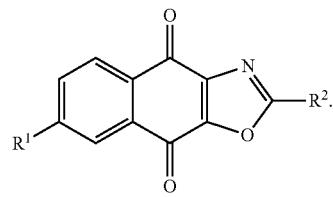

In certain embodiments, n is 1 and a compound of Formula A is

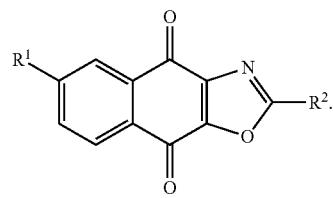

In certain embodiments, n is 1 and a compound of Formula A is

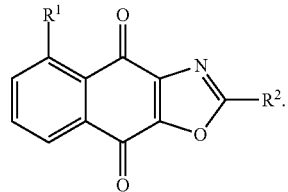

In certain embodiments, n is 2 and a compound of Formula A is

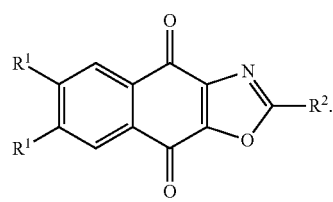

In certain embodiments, n is 2 and a compound of Formula A is

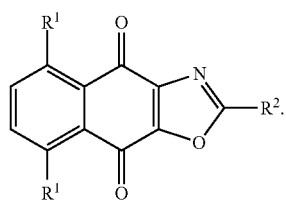

In certain embodiments, n is 2 and a compound of Formula A is

In certain embodiments, n is 2 and a compound of Formula A is

In certain embodiments, n is 3 and a compound of Formula A is

In certain embodiments, n is 3 and a compound of Formula A is

In certain embodiments, n is 3 and a compound of Formula A is

In certain embodiments, n is 3 and a compound of Formula A is

In certain embodiments, n is 4 and a compound of Formula A is $R^2$, $R^4$, $R^B$ and m As is generally defined herein, $R^2$ is cyclic or acyclic, branched or unbranched aliphatic; cyclic or acyclic, branched or unbranched heteroaliphatic; aryl; or heteroaryl; optionally substituted with m instances of $R^4$. As is generally defined herein, each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —C(=$NR^B$)$R^B$, —C(=$NR^B$)$OR^B$, —C(=$NR^B$)N($R^B$)$_2$, —C(=O)$R^B$, —C(=O)$OR^B$, —C(=O)N($R^B$)$_2$, —$NO_2$, —$NR^B$C(=O)$R^B$, —$NR^B$C(=O)$OR^B$, —$NR^B$C(=O)N($R^B$)$_2$, —OC(=O)$R^B$, —OC(=O)$OR^B$, or —OC(=O)N($R^B$)$_2$. As generally defined herein, each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring. As is generally defined herein, m is 0, 1, 2, 3, 4, or 5.

In certain embodiments, $R^2$ is substituted or unsubstituted cycloalkyl. In certain embodiments, $R^2$ is substituted or unsubstituted 3-6 membered cycloalkyl, e.g., cyclopropyl, cyclobutyl, cyclopentyl, or cyclohexyl. In certain embodiments, $R^2$ is 3-6 membered cycloalkyl substituted with 1, 2, 3, 4, or 5 instances of $R^4$, wherein each instance of $R^4$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$.

In certain embodiments, $R^2$ is substituted or unsubstituted cycloalkyl. In certain embodiments, $R^2$ is substituted or unsubstituted 3-6 membered cycloalkyl. In certain embodiments, $R^2$ is substituted 3-6 membered cycloalkyl. In certain embodiments, $R^2$ is unsubstituted 3-6 membered cycloalkyl. In certain embodiments, $R^2$ is substituted cyclopropyl. In certain embodiments, $R^2$ is substituted cyclobutyl. In certain embodiments, $R^2$ is substituted cyclopentyl. In certain embodiments, $R^2$ is substituted cyclohexyl. In certain embodiments, $R^2$ is unsubstituted cyclopropyl. In certain embodiments, $R^2$ is unsubstituted cyclobutyl. In certain embodiments, $R^2$ is unsubstituted cyclopentyl. In certain embodiments, $R^2$ is unsubstituted cyclohexyl.

In certain embodiments, $R^2$ is substituted or unsubstituted, branched or unbranched aliphatic. In certain embodiments, $R^2$ is substituted or unsubstituted, branched or unbranched $C_{1-6}$ aliphatic. In certain embodiments, $R^2$ is substituted or unsubstituted, branched or unbranched $C_{1-3}$ aliphatic. In certain embodiments, $R^2$ is unsubstituted, branched or unbranched $C_{1-6}$ aliphatic. In certain embodiments, $R^2$ is unsubstituted, branched or unbranched $C_{1-3}$ aliphatic. In certain embodiments, $R^2$ is substituted methyl. In certain embodiments, $R^2$ is substituted ethyl. In certain embodiments, $R^2$ is substituted isopropyl. In certain embodiments, $R^2$ is unsubstituted methyl. In certain embodiments, $R^2$ is unsubstituted ethyl. In certain embodiments, $R^2$ is unsubstituted isopropyl.

In certain embodiments, $R^2$ is substituted or unsubstituted alkenyl, e.g., vinyl, allyl, propenyl, or butenyl. In certain embodiments, $R^2$ is substituted or unsubstituted alkynyl, e.g., propargyl, propynyl, or butynyl.

In certain embodiments, $R^2$ is $C_{1-6}$ haloalkyl. In certain embodiments, $R^2$ is —$CF_3$. In certain embodiments, $R^2$ is —$CF_2H$. In certain embodiments, $R^2$ is —$CH_2CF_3$. In certain embodiments, $R^2$ is —$CHF_2$. In certain embodiments, $R^2$ is —$CH_2F$. In certain embodiments, $R^2$ is —$CF_2CH_3$. In certain embodiments, $R^2$ is —$CF_2CF_3$.

In certain embodiments, $R^2$ is substituted or unsubstituted heterocyclyl. In certain embodiments, $R^2$ is substituted or unsubstituted 3-6 membered heterocyclyl, e.g., oxetanyl, tetrahydrofuranyl, pyranyl, azetidinyl, pyrrolidinyl, or piperidinyl. In certain embodiments, $R^2$ is 3-6 membered heterocyclyl substituted with 1, 2, 3, 4, or 5 instances of $R^4$, wherein each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —$C(=NR^B)R^B$, —$C(=NR^B)OR^B$, —$C(=NR^B)N(R^B)_2$, —$C(=O)R^B$, —$C(=O)OR^B$, —$C(=O)N(R^B)_2$, —$NO_2$, —$NR^BC(=O)R^B$, —$NR^BC(=O)OR^B$, —$NR^BC(=O)OR^B$, —$NR^BC(=O)N(R^B)_2$, —$OC(=O)R^B$, —$OC(=O)OR^B$, or —$OC(=O)N(R^B)_2$ and each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring.

In certain embodiments, at least one $R^2$ is substituted or unsubstituted heterocyclyl. In certain embodiments, at least one $R^2$ is substituted or unsubstituted 3-6 membered heterocyclyl. In certain embodiments, at least one $R^2$ is substituted 3-6 membered heterocyclyl. In certain embodiments, at least one $R^2$ is unsubstituted 3-6 membered heterocyclyl. In certain embodiments, at least one $R^2$ is substituted or unsubstituted azetidine. In certain embodiments, at least one $R^2$ is substituted or unsubstituted oxetane. In certain embodiments, at least one $R^2$ is substituted or unsubstituted pyrrolidine. In certain embodiments, at least one $R^2$ is substituted or unsubstituted tetrahydrofuran. In certain embodiments, at least one $R^2$ is substituted or unsubstituted piperidine. In certain embodiments, at least one $R^2$ is substituted or unsubstituted piperazine. In certain embodiments, at least one $R^2$ is substituted or unsubstituted morpholine. In certain embodiments, at least one $R^2$ is substituted or unsubstituted pyran. In certain embodiments, at least one $R^2$ is substituted or unsubstituted dioxane.

In certain embodiments, $R^2$ is substituted or unsubstituted aryl. In certain embodiments, $R^2$ is substituted or unsubstituted phenyl. In certain embodiments, $R^2$ is phenyl substituted with 1, 2, 3, 4, or 5 instances of $R^4$, wherein each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —$C(=NR^B)R^B$, —$C(=NR^B)OR^B$, —$C(=NR^B)N(R^B)_2$, —$C(=O)R^B$, —$C(=O)OR^B$, —$C(=O)N(R^B)_2$, —$NO_2$, —$NR^BC(=O)R^B$, —$NR^BC(=O)OR^B$, —$NR^BC(=O)N(R^B)_2$, —$OC(=O)R^B$, —$OC(=O)OR^B$, or —$OC(=O)N(R^B)_2$ and each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring.

In certain embodiments, $R^2$ is an aryl ring of the formula

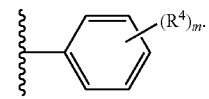

In certain embodiments, R² is an aryl ring of the formula

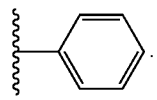

In certain embodiments, R² is an aryl ring of the formula

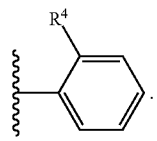

In certain embodiments, R² is an aryl ring of the formula

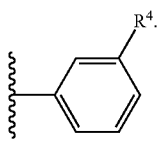

In certain embodiments, R² is an aryl ring of the formula

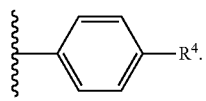

In certain embodiments, R² is an aryl ring of the formula

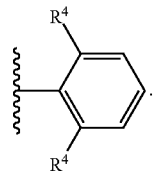

In certain embodiments, R² is an aryl ring of the formula

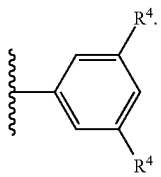

In certain embodiments, R² is an aryl ring of the formula

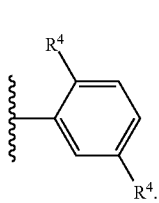

In certain embodiments, R² is an aryl ring of the formula

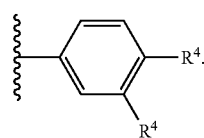

In certain embodiments, R² is an aryl ring of the formula

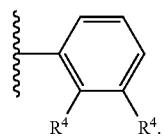

In certain embodiments, R² is an aryl ring of the formula

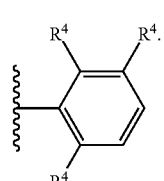

In certain embodiments, R² is an aryl ring of the formula

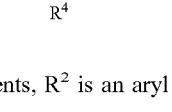

In certain embodiments, R² is an aryl ring of the formula

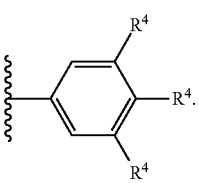

In certain embodiments, R² is an aryl ring of the formula

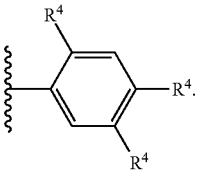

In certain embodiments, R² is an aryl ring of the formula

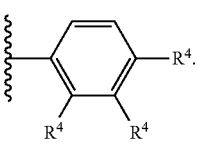

In certain embodiments, R² is an aryl ring of the formula

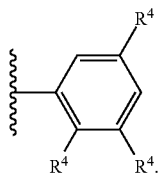

In certain embodiments, R² is an aryl ring of the formula

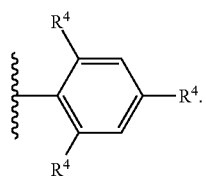

In certain embodiments, R² is an aryl ring of the formula

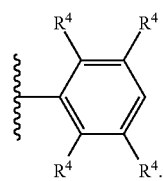

In certain embodiments, R² is an aryl ring of the formula

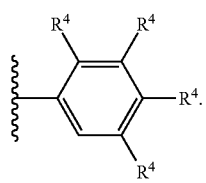

In certain embodiments, R² is an aryl ring of the formula

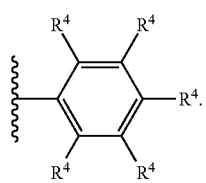

In certain embodiments, R² is not an aryl ring of the formula

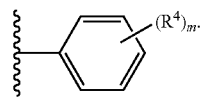

In certain embodiments, R² is not an aryl ring of the formula

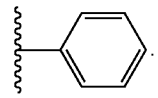 [SMILES: *c1ccccc1]

In certain embodiments, R² is not an aryl ring of the formula

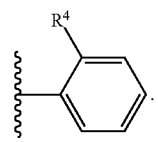

In certain embodiments, R² is not an aryl ring of the formula

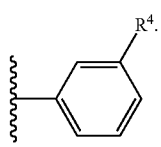

In certain embodiments, R² is not an aryl ring of the formula

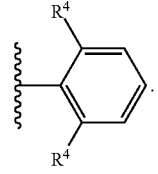

In certain embodiments, R² is not an aryl ring of the formula

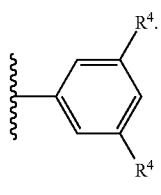

In certain embodiments, R² is not an aryl ring of the formula

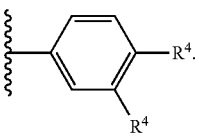

In certain embodiments, R² is not an aryl ring of the formula

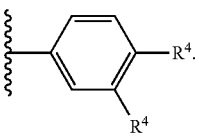

In certain embodiments, $R^2$ is not an aryl ring of the formula

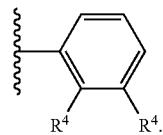

In certain embodiments, $R^2$ is not an aryl ring of the formula

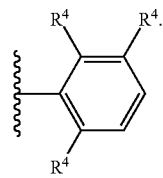

In certain embodiments, $R^2$ is not an aryl ring of the formula

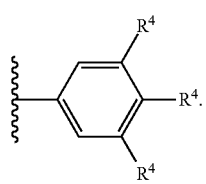

In certain embodiments, $R^2$ is not an aryl ring of the formula

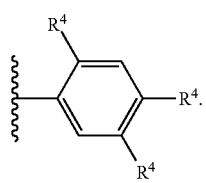

In certain embodiments, $R^2$ is not an aryl ring of the formula

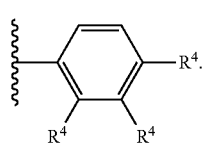

In certain embodiments, $R^2$ is not an aryl ring of the formula

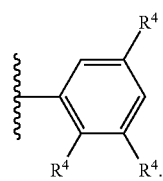

In certain embodiments, $R^2$ is not an aryl ring of the formula

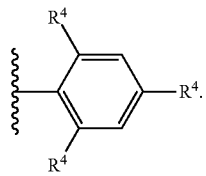

In certain embodiments, $R^2$ is not an aryl ring of the formula

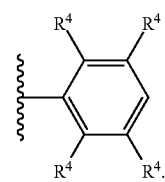

In certain embodiments, $R^2$ is not an aryl ring of the formula

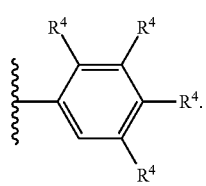

In certain embodiments, $R^2$ is not an aryl ring of the formula

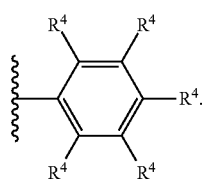

In certain embodiments, $R^2$ is an aryl ring of the formula

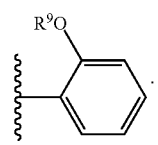

In certain embodiments, $R^2$ is an aryl ring of the formula

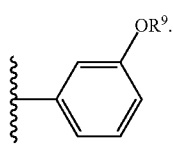

In certain embodiments, $R^2$ is an aryl ring of the formula

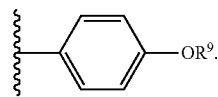

In certain embodiments, $R^2$ is an aryl ring of the formula

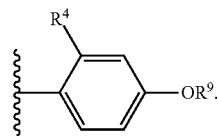

In certain embodiments, $R^2$ is an aryl ring of the formula

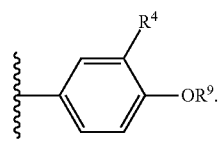

In certain embodiments, $R^2$ is an aryl ring of the formula

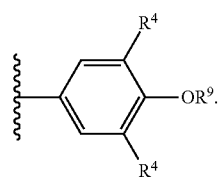

In certain embodiments, $R^2$ is an aryl ring of the formula

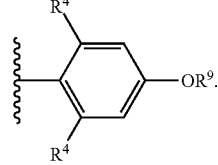

In certain embodiments, $R^2$ is an aryl ring of the formula

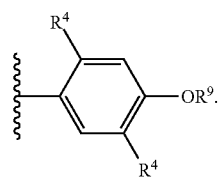

In certain embodiments, $R^2$ is an aryl ring of the formula

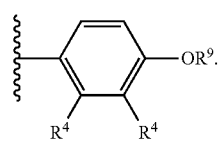

In certain embodiments, $R^2$ is an aryl ring of the formula

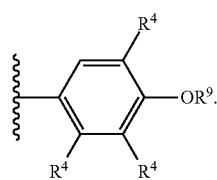

In certain embodiments, $R^2$ is an aryl ring of the formula

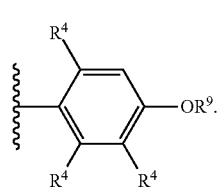

In certain embodiments, $R^2$ is an aryl ring of the formula

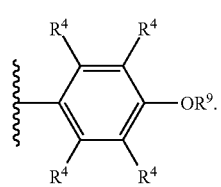

In certain embodiments, $R^2$ is an aryl ring of the formula.

In certain embodiments, $R^2$ is not an aryl ring of the formula

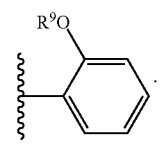

In certain embodiments, $R^2$ is not an aryl ring of the formula

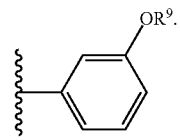

In certain embodiments, $R^2$ is not an aryl ring of the formula

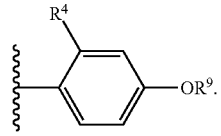

In certain embodiments, R² is not an aryl ring of the formula

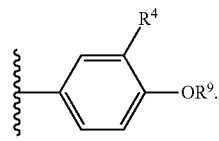

In certain embodiments, R² is not an aryl ring of the formula

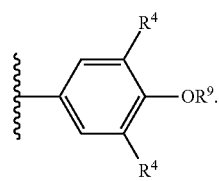

In certain embodiments, R² is not an aryl ring of the formula

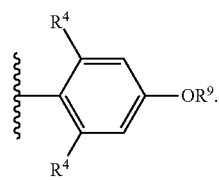

In certain embodiments, R² is not an aryl ring of the formula

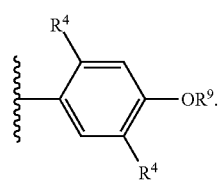

In certain embodiments, R² is not an aryl ring of the formula

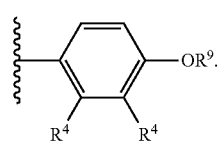

In certain embodiments, R² is not an aryl ring of the formula

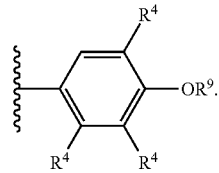

In certain embodiments, R² is not an aryl ring of the formula

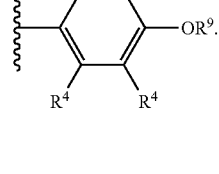

In certain embodiments, R² is not an aryl ring of the formula

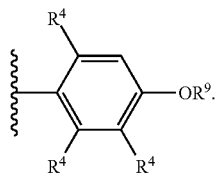

In certain embodiments, R² is not an aryl ring of the formula

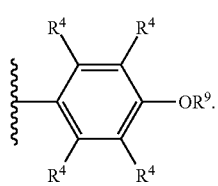

In certain embodiments, R² is an aryl ring of the formula

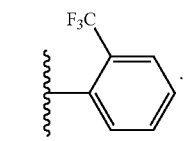 [SMILES: *c1ccccc1C(F)(F)F]

In certain embodiments, R² is an aryl ring of the formula

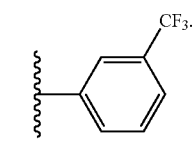 [SMILES: *c1cccc(C(F)(F)F)c1]

In certain embodiments, R² is an aryl ring of the formula

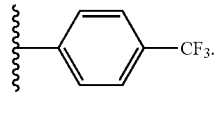

In certain embodiments, R² is an aryl ring of the formula

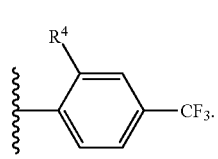

In certain embodiments, R² is an aryl ring of the formula

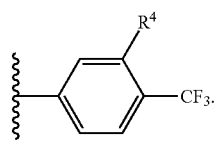

In certain embodiments, $R^2$ is an aryl ring of the formula

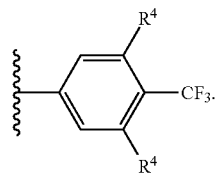

In certain embodiments, $R^2$ is an aryl ring of the formula

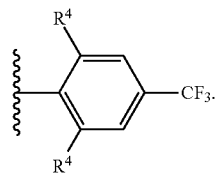

In certain embodiments, $R^2$ is an aryl ring of the formula

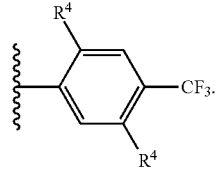

In certain embodiments, $R^2$ is an aryl ring of the formula

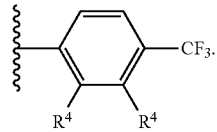

In certain embodiments, $R^2$ is an aryl ring of the formula

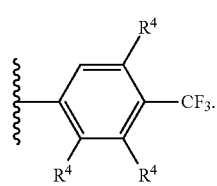

In certain embodiments, $R^2$ is an aryl ring of the formula

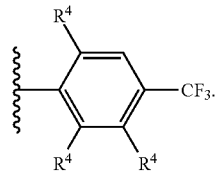

In certain embodiments, $R^2$ is an aryl ring of the formula

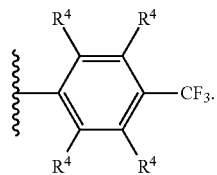

In certain embodiments, $R^2$ is not an aryl ring of the formula

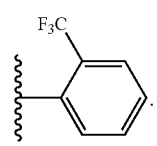

In certain embodiments, $R^2$ is not an aryl ring of the formula

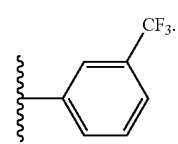

In certain embodiments, $R^2$ is not an aryl ring of the formula

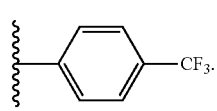

In certain embodiments, $R^2$ is not an aryl ring of the formula

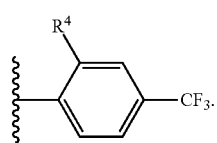

In certain embodiments, $R^2$ is not an aryl ring of the formula

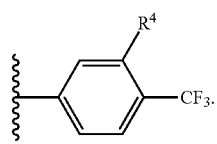

In certain embodiments, $R^2$ is not an aryl ring of the formula

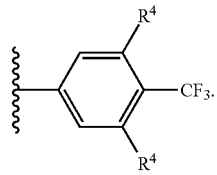

In certain embodiments, R² is not an aryl ring of the formula

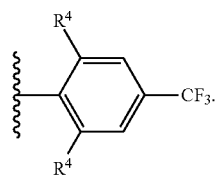

In certain embodiments, R² is not an aryl ring of the formula

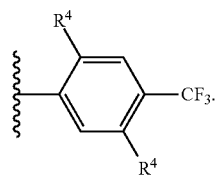

In certain embodiments, R² is not an aryl ring of the formula

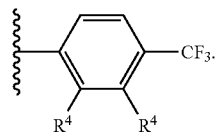

In certain embodiments, R² is not an aryl ring of the formula

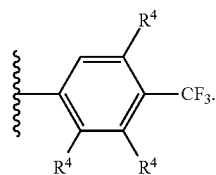

In certain embodiments, R² is not an aryl ring of the formula

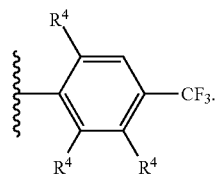

In certain embodiments, R² is not an aryl ring of the formula

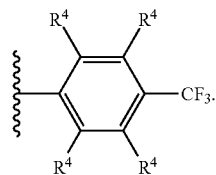

In certain embodiments, R² is substituted or unsubstituted heteroaryl. In certain embodiments, R² is substituted or unsubstituted 5-6 membered heteroaryl, e.g., pyrazolyl, imidazolyl, thiazolyl, oxazolyl, isothiazolyl, isoxazolyl, triazolyl, pyridinyl, pyrazinyl, pyrimidinyl, or pyridizinyl. In certain embodiments, R² is 5-6 membered heteroaryl substituted with 1, 2, 3, 4, or 5 instances of R⁴, wherein each instance of R⁴ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^B$, —N(R$^B$)₂, —SR$^B$, —CN, —SCN, —C(=NR$^B$)R$^B$, —C(=NR$^B$)OR$^B$, —C(=NR$^B$)N(R$^B$)₂, —C(=O)R$^B$, —C(=O)OR$^B$, —C(=O)N(R$^B$)₂, —NO₂, —NR$^B$C(=O)R$^B$, —NR$^B$C(=O)OR$^B$, —NR$^B$C(=O)N(R$^B$)₂, —OC(=O)R$^B$, —OC(=O)OR$^B$, or —OC(=O)N(R$^B$)₂ and each instance of R$^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^B$ groups are joined to form a substituted or unsubstituted heterocyclic or substituted or unsubstituted heteroaryl ring.

In certain embodiments, R² is a heteroaryl ring of the formula

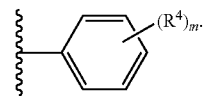

In certain embodiments, R² is a heteroaryl ring of the formula

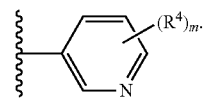

In certain embodiments, R² is a heteroaryl ring of the formula

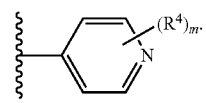

In certain embodiments, R² is a heteroaryl ring of the formula

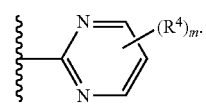

In certain embodiments, R² is a heteroaryl ring of the formula

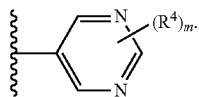

In certain embodiments, $R^2$ is a heteroaryl ring of the formula

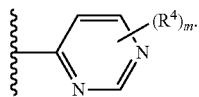

In certain embodiments, $R^2$ is a heteroaryl ring of the formula

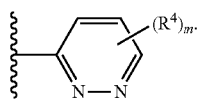

In certain embodiments, $R^2$ is a heteroaryl ring of the formula

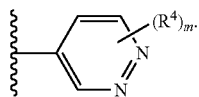

In certain embodiments, $R^2$ is a heteroaryl ring of the formula

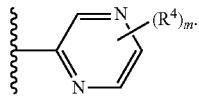

In certain embodiments, $R^2$ is a heteroaryl ring of the formula

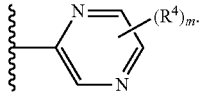

In certain embodiments, $R^2$ is a heteroaryl ring of the formula

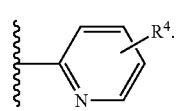

In certain embodiments, $R^2$ is a heteroaryl ring of the formula

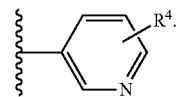

In certain embodiments, $R^2$ is a heteroaryl ring of the formula

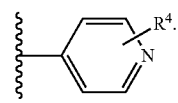

In certain embodiments, $R^2$ is a heteroaryl ring of the formula

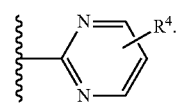

In certain embodiments, $R^2$ is a heteroaryl ring of the formula

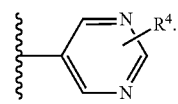

In certain embodiments, $R^2$ is a heteroaryl ring of the formula

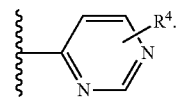

In certain embodiments, $R^2$ is a heteroaryl ring of the formula

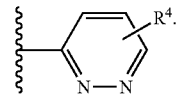

In certain embodiments, $R^2$ is a heteroaryl ring of the formula

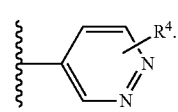

In certain embodiments, $R^2$ is a heteroaryl ring of the formula

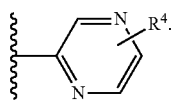

In certain embodiments, $R^2$ is a heteroaryl ring of the formula

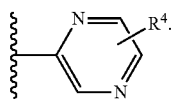

In certain embodiments, $R^2$ is a heteroaryl ring of the formula

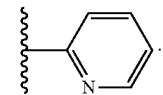

In certain embodiments, $R^2$ is a heteroaryl ring of the formula

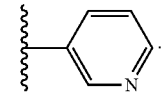

In certain embodiments, $R^2$ is a heteroaryl ring of the formula

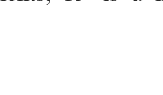

In certain embodiments, $R^2$ is a heteroaryl ring of the formula

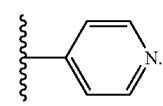

In certain embodiments, $R^2$ is a heteroaryl ring of the formula

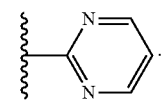

In certain embodiments, $R^2$ is a heteroaryl ring of the formula

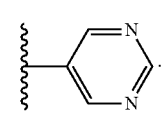

In certain embodiments, $R^2$ is a heteroaryl ring of the formula

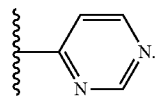

In certain embodiments, $R^2$ is a heteroaryl ring of the formula

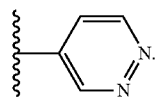

In certain embodiments, $R^2$ is a heteroaryl ring of the formula

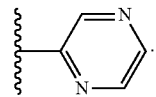

In certain embodiments, $R^2$ is a heteroaryl ring of the formula

In certain embodiments, $R^2$ is a phenyl ring; n is 1; and $R^4$ is $-OR^B$. In certain embodiments, $R^2$ is a phenyl ring; n is 1; $R^4$ is $-OR^B$; and $R^B$ is substituted or unsubstituted alkyl. In certain embodiments, $R^2$ is a phenyl ring; n is 1; $R^4$ is $-OR^B$; and $R^B$ is substituted or unsubstituted $C_{1-6}$ alkyl. In certain embodiments, $R^2$ is a phenyl ring; n is 1; $R^4$ is $-OR^B$; and $R^B$ is methyl. In certain embodiments, $R^2$ is a phenyl ring; n is 1; $R^4$ is $-OR^B$; and $R^B$ is ethyl. In certain embodiments, $R^2$ is a phenyl ring; n is 1; $R^4$ is $-OR^B$; and $R^B$ is propyl. In certain embodiments, $R^2$ is a phenyl ring; n is 1; $R^4$ is $-OR^B$; and $R^B$ is isopropyl. In certain embodiments, $R^2$ is a phenyl ring; n is 1; $R^4$ is $-OR^B$; and $R^B$ is butyl. In certain embodiments, $R^2$ is a phenyl ring; n is 1; $R^4$ is $-OR^B$; and $R^B$ is tert-butyl. In certain embodiments, $R^2$ is a phenyl ring; n is 1; $R^4$ is $-OR^B$; and $R^B$ is substituted or unsubstituted $C_{1-6}$ haloalkyl. In certain embodiments, $R^2$ is a phenyl ring; n is 1; $R^4$ is $-OR^B$; and $R^B$ is substituted or unsubstituted alkenyl. In certain embodiments, $R^2$ is a phenyl ring; n is 1; $R^4$ is $-OR^B$; and $R^B$ is allyl. In certain embodiments, $R^2$ is a phenyl ring; n is 1; $R^4$ is $-OR^B$; and $R^B$ is substituted or unsubstituted alkynyl. In certain embodiments, $R^2$ is a phenyl ring; n is 1; $R^4$ is $-OR^B$; and $R^B$ is propargyl.

In certain embodiments, at least one $R^4$ is $C_{1-6}$ haloalkyl. In certain embodiments, at least one $R^4$ is $-CF_3$. In certain embodiments, at least one $R^4$ is —$CF_2H$. In certain embodiments, at least one $R^4$ is —$CH_2CF_3$. In certain embodiments, at least one $R^4$ is —$CHF_2$. In certain embodiments, at least one $R^4$ is —$CH_2F$. In certain embodiments, at least one $R^4$ is —$CF_2CH_3$. In certain embodiments, at least one $R^4$ is —$CF_2CF_3$.

In certain embodiments, n is 0. In certain embodiments, n is 1. In certain embodiments, n is 2. In certain embodiments, n is 3. In certain embodiments, n is 4. In certain embodiments, n is not 0. In certain embodiments, n is not 1. In certain embodiments, n is not 2. In certain embodiments, n is not 3. In certain embodiments, n is not 4.

Methods of Treatment

Certain aspects of the invention relate to methods for treating cancers using the compounds described herein. In some embodiments, a method for treating epidermal growth factor receptor (EGFR)-mutant non-small cell lung cancer is provided. The method comprises identifying a subject having an EGFR-mutant non-small cell lung cancer; and administering to the subject a compound according to Formula I:

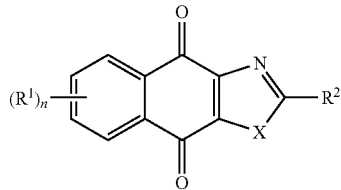

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^4$; —$C(=O)R^4$; —$C(=O)N(R^4)_2$; —$CO_2R^4$; —CN; —SCN; —$SR^4$; —$SOR^4$; —$SO_2R^4$; —$NO_2$; —$N_3$; —$N(R^4)_2$; —$NHC(=O)R^4$; —$NR^4C(=O)N(R_4)_2$; —$OC(=O)OR^4$; —$OC(=O)R^4$; —$OC(=O)N(R^4)_2$; —$NR^4C(=O)OR^4$; or —$C(R^4)_3$; wherein each occurrence of $R^4$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof in an amount effective to treat the EGFR-mutant non-small cell lung cancer.

In some embodiments, a method for treating non-small cell lung cancer resistant to at least one of gefitinib, erlotinib and lapatinib is provided. The method comprises administering to a subject in need thereof a compound according to Formula I:

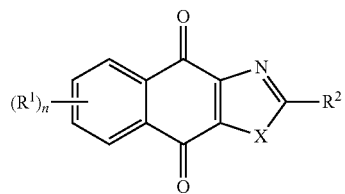

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^4$; —$C(=O)R^4$; —$C(=O)N(R^4)_2$; —$CO_2R^4$; —CN; —SCN; —$SR^4$; —$SOR^4$; —$SO_2R^4$; —$NO_2$; —$N_3$; —$N(R^4)_2$; —$NHC(=O)R^4$; —$NR^4C(=O)N(R_4)_2$; —$OC(=O)OR^4$; —$OC(=O)R^4$; —$OC(=O)N(R^4)_2$; —$NR^4C(=O)OR^4$; or —$C(R^4)_3$; wherein each occurrence of $R^4$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the non-small cell lung cancer resistant to at least one of gefitinib, erlotinib and lapatinib.

In some embodiments, a method for treating epidermal growth factor receptor (EGFR)-mutant non-small cell lung cancer is provided. The method comprises administering to a subject in need thereof a compound according to Formula I:

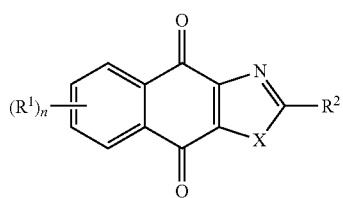

Formula I wherein

X is O, S, or $NR^3$;

n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R^A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the EGFR-mutant non-small cell lung cancer.

EGFR is a member of the ErbB family of closely related receptors including EGFR (ErbB-1), Her2/neu (ErbB-2), Her3 (ErbB-3) and Her4 (ErbB-4). As used herein, the EGFR protein is disclosed as GenBank accession no. NP_005219. Activation of EGFR leads to receptor tyrosine kinase activation and a series of downstream signaling events that mediate cellular proliferation, motility, adhesion, invasion, and resistance to chemotherapy as well as inhibition of apoptosis, processes that are crucial to the continual proliferation and survival of cancer cells. Several anti-EGFR agents, including small molecule EGFR tyrosine kinase inhibitors (TKIs) have entered the clinical setting. TKIs such as gefitinib (compound ZD 1839, Iressa) or erlotinib (compound OSI-774, Tarceva) compete with ATP for binding to the intracellular catalytic domain of the EGFR tyrosine kinase and, thus, prevent EGFR autophosphorylation and downstream signaling.

By "EGFR-mutant non-small cell lung cancer" is meant a non-small cell lung cancer that has a cancer cell having an aberrant (i.e., an increased) EGFR kinase activity as compared to normal (non-cancerous) cells. In some embodiments, the aberrant (i.e., an increased) EGFR kinase activity may be caused by a mutation in an EGFR gene. In some embodiments, the EGFR mutant or mutant includes one or more deletions, substitutions, additions in the amino acid or nucleotide sequences of EGFR protein, or EGFR coding sequence. In particular EGFR mutations, kinase activity can be increased (e.g., by at least 5%, 10%, 15%, 20%, 30%, 40%, 50%, 60%, 70%, 80%, 90%, or even 100%), as compared to wild type EGFR. In some embodiments, the aberrant (i.e., an increased) EGFR kinase activity may be caused by an increase in gene copy number and/or increased protein expression (see, for example, Hirsch et al. Journal of Clinical Oncology Jul. 10, 2008 vol. 26 no. 20 3351-335; Hirsch et al. Journal of Clinical Oncology, Vol 21, No 20 (Oct. 15), 2003: pp 3798-3807; incorporated by reference herein). In some embodiments, the expression of EGFR protein can be increased (e.g., by at least 5%, 10%, 15%, 20%, 30%, 40%, 50%, 60%, 70%, 80%, 90%, or even 100%), as compared to wild type EGFR.

Examples of EGFR mutations include but are not limited to, activating (sensitizing) mutations and resistance mutations. Activating (sensitizing) mutations, which typically take the form of small deletions or point mutations in the kinase domain and lead to increased kinase activity, have been cataloged and described at length in the scientific literature. See e.g., Sharma, Nat. Rev. Cancer 7:169 (2007) (exon 19 mutations characterized by in-frame deletions of amino-acids 747 account for 45% of mutations, exon 21 mutations resulting in L858R substitutions account for 40-45% of mutations, and the remaining 10% of mutations involve exon 18 and 20); Sordella et al., Science 305:1 163 (2004); and Mulloy et al., Cancer Res. 67:2325 (2007). Thus, examples of sentizing mutations include, but are not limited to: leucine (L) to an arginine (R) substitution at position 858 (L858R), leucine (L) to a glutamine (Q) substitution at position 861 (L861Q), glycine (G) to a serine (S) substitution at position 719 (G719S), exon 19 deletions (del 19) and exon 20 insertions.

The clinical efficacy of TKIs such as gefitinib and erlotinib is ultimately limited by the development of resistance. Resistance mutations known in the art include, but are not limited to a mutation in the EGFR kinase domain gatekeeper residue (threonine (T) to a methionine (M) substitution at position 790 (T790M)), which occurs in 50% of patients.

An EGFR-mutant non-small cell lung cancer can be identified using assays well known and documented in the art. For example, the EGFR-mutant non-small cell lung cancer can be detected by assaying for aberrant (i.e., an increased) EGFR kinase activity as compared to normal (non-cancerous) cells. EGFR kinase activity assays are well known in the art and include but are not limited to the ADP-Glo™ Kinase Assay (Promega) or the HTScan® EGF Receptor Kinase Assay Kit (Cell Signaling Technology). In some embodiments, the EGFR-mutant non-small cell lung cancer can be detected by assaying for increased gene copy number and/or increased protein expression. The increased gene copy number can be detected, for example, using Fluorescence in situ hybridization (FISH), while protein overexpression may be determined using Western Blotting or immunohistochemistry (see, for example, Hirsch et al. Journal of Clinical Oncology Jul. 10, 2008 vol. 26 no. 20 3351-335; Hirsch et al. Journal of Clinical Oncology, Vol 21, No 20 (October 15).

In some embodiments, the methods described herein, comprise identifying a subject having an EGFR-mutant non-small cell lung cancer. As used herein, "identifying a subject having an EGFR-mutant non-small cell lung cancer" means selecting a subject on the basis that the subject has an EGFR-mutant non-small cell lung cancer. It is understood that diagnosis and treatment of a complex disease such as cancer is not performed by a single individual, test, agent, or intervention. For example, a subject may meet with a primary care physician to express a concern and be referred to an oncologist who will request tests that are designed, carried out, and analyzed by any of a number of individuals, but not limited to, radiologists, radiology technicians, physicists, phlebotomists, pathologists, laboratory technicians, and radiation, clinical, and surgical oncologists. Selection, dosing, and administration of agents to a subject diagnosed with cancer will be performed by any of a number of individuals including, but not limited to, radiologists, radiology technicians, physicists, pathologists, infusion nurses, pharmacists, and radiation, clinical, and surgical oncologists. Therefore, it is understood that within the terms of the invention, identifying a subject having an EGFR-mutant non-small cell lung cancer can include any of a number of acts including, but not limited to, performing a test and observing a result that is indicative of a subject having a mutation in EGFR; reviewing a test result of a subject and identifying the subject as having a mutation in EGFR; reviewing documentation on a subject stating that the subject has a mutation in EGFR and identifying the subject as the one discussed in the documentation by confirming the identity of the subject, e.g., by an identification card, hospital bracelet, asking the subject for his/her name and/or other personal information to confirm the subject's identity.

In some embodiments, the subject is identified as having the EGFR-mutant non-small cell lung cancer by performing an analysis of a sample obtained of the subject. A number of assays are known in the art for determining whether a subject has an EGFR mutant NSCLC, including but not limited to direct sequencing, PCR-based assays, immunohistochemistry, and Fluorescence in situ hybridization (FISH). Thus, the sample can be analyzed for aberrant EGFR genotype/phenotype by PCR-based assays (e.g., polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays), direct sequencing, primer extension reactions, electrophoresis, oligonucleotide ligation assays, hybridization assays, TaqMan assays, SNP genotyping assays, high resolution melting assays and/or microarray analysis. In some embodiments, the sample is analyzed using Cobas® EGFR Mutation Test, which is a recent FDA-approved automated molecular assay designed to detect the presence of 41 mutations in Exons 18, 19, 20 and 21 of the EGFR gene (Roche Molecular Diagnostics; http://molecular.roche.com/assays/Pages/cobasEGFRMutationTest.aspx; incorporated by reference herein).

Alteration of wild-type EGFR gene can be detected by screening for alteration of EGFR mRNA and/or protein expression. For example EGFR mutations may be detected by amplifying and sequencing the mRNA or via molecular cloning of cDNA made from the mRNA. The sequence of the cloned cDNA can be determined using DNA sequencing techniques which are well known in the art. Monoclonal antibodies immunoreactive with EGFR can be also used to screen a sample. Antibodies specific for products of mutant alleles could also be used to detect mutant EGFR gene product. For example, EGFR mutations may be detected with mutation-specific antibodies (e.g., Simonetti et al. Journal of Translational Medicine 2010, 8:135 which is incorporated by reference herein). Such immunological assays can be done in any convenient format known in the art. These include Western blots, immunohistochemical assays and ELISA assays.

Mutant EGFR gene or gene products can be detected from tumor tissue or from other body samples such as blood, sputum and urine.

Some aspects of the invention involve methods for treating non-small cell lung cancer resistant to treatment by tyrosine kinase inhibitors. In some embodiments, aspects of the invention involve methods for treating non-small cell lung cancer resistant to at least one of gefitinib, erlotinib and lapatinib.

Gefitinib (compound ZD 1839 developed by AstraZeneca UK Ltd.; available under the tradename IRESSA), erlotinib (compound OSI-774 developed by Genentech, Inc. and OSI Pharmaceuticals, Inc.; available under the trade name TARCEVA) and lapatinib (developed by GlaxoSmithKline (GSK) under the propriety names Tykerb and Tyverb) induce clinical responses in cases of non-small cell lung cancers (NSCLCs) harboring activating mutations in the EGF receptor (EGFR). The effectiveness of these tyrosine kinase inhibitors may result both from alterations in the ATP cleft associated with these mutations, which lead to enhanced inhibition of the mutant kinase by these drugs, and from biological dependence of these cancer cells on the increased survival signals transduced by the mutant receptors, a phenomenon described as "oncogene addiction" (Nicholson R I, Gee J M W, Harper M E. EGFR and cancer prognosis. Eur J Cancer. 2001; 37:S9-15; Wong A J, Ruppert J M, Bigner S H, et al. Structural alterations of the epidermal growth factor receptor gene in human gliomas. Proc Natl Acad Sci. 1992; 89:2965-2969).

Cancers may initially be diagnosed as sensitive to gefitinib, erlotinib and/or lapatinib treatment or predicted to be sensitive to gefitinib, erlotinib and/or lapatinib treatment by means of the methods such as those described in Lynch et al. (*N Engl J Med.* 2004; 350:2129-2139; incorporated by reference herein). Sensitivity to Gefitinib, erlotinib and/or lapatinib treatment may be predicted by the presence in the tumor of EGFR mutations including, for example, deletion of residues 747 (lysine) to 749 (glutamic acid) combined with a mutation in 750 (alanine), deletion of residues 747 (lysine) to 750 (alanine), substitution of arginine for leucine at residue 858, of substitution of glutamine for leucine at residue 861.

Cancers may be diagnosed as resistant to gefitinib, erlotinib and/or lapatinib after treatment with these TKIs has commenced. Alternatively, cancers may be diagnosed as gefitinib, erlotinib and/or lapatinib resistant prior to initiation of treatment with such compounds. Gefitinib, erlotinib and/or lapatinib resistance in the tumor may occur after, e.g., 6 months or longer of gefitinib, erlotinib and/or lapatinib treatment. Alternatively, gefitinib, erlotinib and/or lapatinib resistance of the tumor may be diagnosed less than 6 months after gefitinib, erlotinib and/or lapatinib treatment has commenced. Diagnosis of gefitinib, erlotinib and/or lapatinib resistance may be accomplished by way of monitoring tumor progression during gefitinib, erlotinib and/or lapatinib treatment. Tumor progression may be determined by comparison of tumor status between time points after treatment has commenced or by comparison of tumor status between a time point after treatment has commenced to a time point prior to initiation of gefitinib, erlotinib and/or lapatinib treatment. Tumor progression may be monitored during gefitinib, erlotinib and/or lapatinib treatment visually, for example, by means of radiography, for example, X-ray, CT scan, or other monitoring methods known to the skilled artisan, including palpitation of the cancer or methods to monitor tumor biomarker levels. Progression of the cancer during treatment with gefitinib, erlotinib and/or lapatinib indicates gefitinib, erlotinib and/or lapatinib resistance. A rise in level of tumor biomarkers indicates tumor progression. Thus, a rise in tumor biomarker levels during treatment with gefitinib, erlotinib and/or lapatinib indicates gefitinib, erlotinib and/or lapatinib resistance. Detection of new tumors or detection of metastasis indicates tumor progression. Cessation of tumor shrinkage indicates tumor progression. Growth of the cancer is indicated by, for example, increase in tumor size, metastasis or detection of new cancer, and/or a rise in tumor biomarker levels.

The development of gefitinib, erlotinib and/or lapatinib resistance may be monitored by means of testing for presence of a gefitinib, erlotinib and/or lapatinib resistance associated mutation in tumor tissue or circulating tumor cells obtained from the circulation, or other bodily fluid (e.g., urine, sputum), of the subject. Presence of gefitinib, erlotinib and/or lapatinib resistance associated mutations in tumor cells from the subject is indicative of a gefitinib, erlotinib and/or lapatinib resistant tumor.

In one embodiment, the subject's tumor harbors mutations indicative of gefitinib, erlotinib and/or lapatinib sensitivity, yet it is resistant to gefitinib, erlotinib and/or lapatinib treatment. In one embodiment, the subject's tumor harbors mutations indicative gefitinib, erlotinib and/or lapatinib sensitivity and harbors mutations indicative of gefitinib, erlotinib and/or lapatinib resistance, e.g., the T790M mutation, that is, where a methione residue is substituted for the native threonine residue, in EGFR. In one embodiment, the subject's tumor does not harbor mutations indicative of gefitinib, erlotinib and/or lapatinib sensitivity and does harbor mutations indicative of gefitinib, erlotinib and/or lapatinib resistance, e.g., the T790M mutation in EGFR.

The compounds used to treat NSCLC as described herein include a compound according to Formula I:

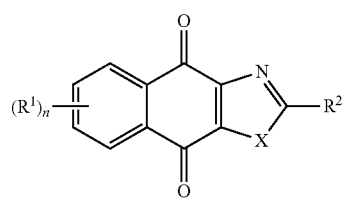

Formula I wherein
X is O, S, or NR$^3$;
n is 0, 1, 2, 3, or 4;

each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^A$; —C(=O)R$^A$; —C(=O)N(R$^A$)$_2$; —CO$_2$R$^A$; —CN; —SCN; —SR$^A$; —SOR$^A$; —SO$_2$R$^A$; —NO$_2$; —N$_3$; —N(R$^A$)$_2$; —NHC(=O)R$^A$; —NR$^A$C(=O)N(R$_A$)$_2$; —OC(=O)OR$^A$; —OC(=O)R$^A$; —OC(=O)N(R$^A$)$_2$; —NR$^A$C(=O)OR$^A$; or —C(R$^A$)$_3$; wherein each occurrence of R$^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^B$; —C(=O)R$^B$; —C(=O)N(R$^B$)$_2$; —CO$_2$R$^B$; —CN; —SCN; —SR$^B$; —SOR$^B$; —SO$_2$R$^B$; —NO$_2$; —N$_3$; —N(R$^B$)$_2$; —NHC(=O)R$^B$; —NR$^B$C(=O)N(R$^B$)$_2$; —OC(=O)OR$^B$; —OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof. These compounds have been described in WO 2011/137320 (incorporated by reference herein).

In some embodiments, the compounds used to treat NSCLC include compounds of Formula A, An-1, An-2, An-3, Ac-1, Ac-2, and Ac-3 described herein. In some embodiments, the compound is:

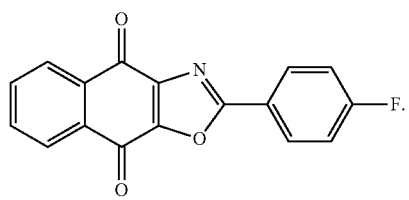

(527)

In some embodiments, the compound is:

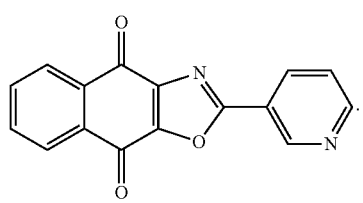

(019A)

In some embodiments, the compound is:

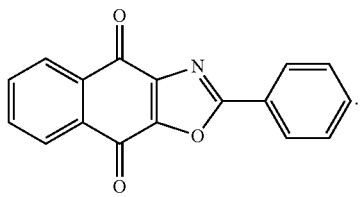

(043)

In some embodiments, the compounds used to treat NSCLC as described herein are USP8 inhibitors. In some embodiments, the compounds of the invention inhibit USP8 activity and promote degradation of EGFR.

The invention also provides a method for inhibiting USP8-mediated deubiqitination of a ubiquitinated substrate, whereby the ubiquitinated substrate is contacted with a small molecule inhibitor of USP8 selected from the group consisting of a compound of Formula A, An-1, An-2, An-3, Ac-1, Ac-2, and Ac-3 described herein, and any combination thereof, in an amount effective to inhibit USP8-mediated deubiqitination of the ubiquitinated substrate. In one embodiment the small molecule inhibitor of USP8 is the compound of Formula A. The method can be performed in vitro or in vivo. In one embodiment the ubiquitinated substrate is an isolated ubiquitinated substrate. A substrate or other compound is "isolated" when it is substantially separated from other cellular components with which it is found in nature. In one embodiment an isolated substrate is a substrate that has been purified from a natural source. In one embodiment the isolated substrate is expressed artificially by a host cell and then separated from the host cell.

In one embodiment the substrate is a natural substrate of USP8. For example, in one embodiment the substrate is the seven transmembrane protein Smoothened (Smo). (PLoS Biology, 2012, 10 (1), e1001238).

As used herein, a "subject having a EGFR-mutant non-small cell lung cancer" refers to a living mammal with a detectable EGFR-mutant non-small cell lung cancer. In one embodiment the subject is a human. Methods for identifying subjects having a EGFR-mutant non-small cell lung cancer are well known in the art and are described herein.

Some aspects of the invention provide a method for treating cyclin D1- and/or USP2a-dependent prostate cancer. The method comprises administering to a subject in need thereof a compound according to Formula I:

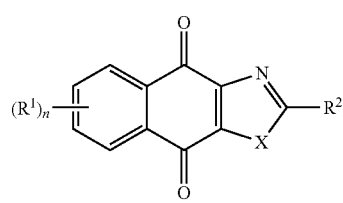

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^A$; $-C(=O)R^A$; $-C(=O)N(R^A)_2$; $-CO_2R^A$; $-CN$; $-SCN$; $-SR^A$; $-SOR^A$; $-SO_2R^A$; $-NO_2$; $-N_3$; $-N(R^A)_2$; $-NHC(=O)R^A$; $-NR^AC(=O)N(R_A)_2$; $-OC(=O)OR^A$; $-OC(=O)R^A$; $-OC(=O)N(R^A)_2$; $-NR^AC(=O)OR^A$; or $-C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^B$; $-C(=O)R^B$; $-C(=O)N(R^B)_2$; $-CO_2R^B$; $-CN$; $-SCN$; $-SR^B$; $-SOR^B$; $-SO_2R^B$; $-NO_2$; $-N_3$; $-N(R^B)_2$; $-NHC(=O)R^B$; $-NR^BC(=O)N(R^B)_2$; $-OC(=O)OR^B$; $-OC(=O)R^B$; $-OC(=O)N(R^B)_2$; $-NR^BC(=O)OR^B$; or $-C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof,
in an amount effective to treat the cyclin D1- and/or USP2a-dependent prostate cancer.

Some aspects of the invention provide a method for treating cyclin D1- and/or USP2a-dependent prostate cancer. The method comprises identifying a subject having a cyclin D1- and/or USP2a-dependent prostate cancer; and administering to the subject a compound according to Formula I:

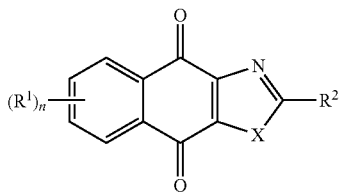

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^A$; $-C(=O)R^A$; $-C(=O)N(R^A)_2$; $-CO_2R^A$; $-CN$; $-SCN$; $-SR^A$; $-SOR^A$; $-SO_2R^A$; $-NO_2$; $-N_3$; $-N(R^A)_2$; $-NHC(=O)R^A$; $-NR^AC(=O)N(R_A)_2$; $-OC(=O)OR^A$; $-OC(=O)R^A$; $-OC(=O)N(R^A)_2$; $-NR^AC(=O)OR^A$; or $-C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —C(=O)$R^B$; —C(=O)N($R^B$)$_2$; —CO$_2R^B$; —CN; —SCN; —$SR^B$; —$SOR^B$; —$SO_2R^B$; —$NO_2$; —$N_3$; —N($R^B$)$_2$; —NHC(=O)$R^B$; —$NR^B$C(=O)N($R^B$)$_2$; —OC(=O)$OR^B$; —OC(=O)$R^B$; —OC(=O)N($R^B$)$_2$; —$NR^B$C(=O)$OR^B$; or —C($R^B$)$_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the cyclin D1- and/or USP2a-dependent prostate cancer.

Some aspects of the invention provide a method for treating androgen receptor (AR)- and/or USP12-dependent prostate cancer. The method comprises administering to a subject in need thereof a compound according to Formula I:

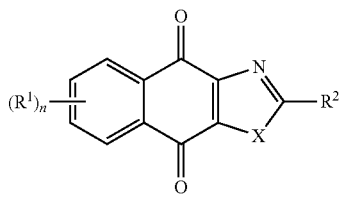

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —C(=O)$R^A$; —C(=O)N($R^A$)$_2$; —CO$_2R^A$; —CN; —SCN; —$SR^A$; —$SOR^A$; —$SO_2R^A$; —$NO_2$; —$N_3$; —N($R^A$)$_2$; —NHC(=O)$R^A$; —$NR^A$C(=O)N($R_A$)$_2$; —OC(=O)$OR^A$; —OC(=O)$R^A$; —OC(=O)N($R^A$)$_2$; —$NR^A$C(=O)$OR^A$; or —C($R^A$)$_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —C(=O)$R^B$; —C(=O)N($R^B$)$_2$; —CO$_2R^B$; —CN; —SCN; —$SR^B$; —$SOR^B$; —$SO_2R^B$; —$NO_2$; —$N_3$; —N($R^B$)$_2$; —NHC(=O)$R^B$; —$NR^B$C(=O)N($R^B$)$_2$; —OC(=O)$OR^B$; —OC(=O)$R^B$; —OC(=O)N($R^B$)$_2$; —$NR^B$C(=O)$OR^B$; or —C($R^B$)$_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the androgen receptor (AR)- and/or USP12-dependent prostate cancer.

Some aspects of the invention provide a method for treating androgen receptor (AR)- and/or USP12-dependent prostate cancer. The method comprises identifying a subject having a androgen receptor (AR)- and/or USP12-dependent prostate cancer; and administering to the subject a compound according to Formula I:

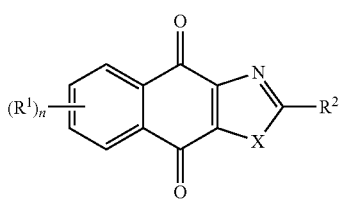

Formula I wherein
X is O, S, or $NR^3$;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —C(=O)$R^A$; —C(=O)N($R^A$)$_2$; —CO$_2R^A$; —CN; —SCN; —$SR^A$; —$SOR^A$; —$SO_2R^A$; —$NO_2$; —$N_3$; —N($R^A$)$_2$; —NHC(=O)$R^A$; —$NR^A$C(=O)N($R_A$)$_2$; —OC(=O)$OR^A$; —OC(=O)$R^A$; —OC(=O)N($R^A$)$_2$; —$NR^A$C(=O)$OR^A$; or —C($R^A$)$_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —C(=O)$R^B$; —C(=O)N($R^B$)$_2$; —CO$_2R^B$; —CN; —SCN; —$SR^B$; —$SOR^B$; —$SO_2R^B$; —$NO_2$; —$N_3$; —N($R^B$)$_2$; —NHC(=O)$R^B$; —$NR^B$C(=O)N($R^B$)$_2$; —OC(=O)$OR^B$;

—OC(=O)R$^B$; —OC(=O)N(R$^B$)$_2$; —NR$^B$C(=O)OR$^B$; or —C(R$^B$)$_3$; wherein each occurrence of R$^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof, in an amount effective to treat the androgen receptor (AR)- and/or USP12-dependent prostate cancer.

Cyclin D1 belongs to the highly conserved cyclin family which function as regulators of CDKs (Cyclin-dependent kinase). Cyclin D1 forms a complex with and functions as a regulatory subunit of CDK4 or CDK6, whose activity is required for cell cycle G1/S transition. Mutations, amplification and overexpression of this gene, which alters cell cycle progression, are observed frequently in a variety of tumors and may contribute to tumorigenesis. USP2 has been identified as a specific deubiquitinase for cyclin D1 (Shan et al. Mol Cell. 2009 Nov. 13; 36(3):469-76). USP2 directly interacts with cyclin D1 and promotes its stabilization by antagonizing ubiquitin-dependent degradation. Conversely, USP2 knockdown destabilizes cyclin D1 and induces growth arrest in the human cancer lines where cell growth is dependent on cyclin D1 expression (Shan et al. Mol Cell. 2009 Nov. 13; 36(3):469-76).

By "cyclin D1- and/or USP2a-dependent prostate cancer" is meant a prostate cancer that has a cancer cell having an aberrant (i.e., an increased) cyclin D1 expression and/or an aberrant (i.e., an increased) USP2a expression as compared to normal (non-cancerous) cells. In some embodiments, the cyclin D1 and/or USP2a expression in cancer cells is increased (e.g., by at least 5%, 10%, 15%, 20%, 30%, 40%, 50%, 60%, 70%, 80%, 90%, or even 100%), as compared to normal (non-cancerous cells).

A cyclin D1- and/or USP2a-dependent prostate cancer can be identified using assays well known and documented in the art. As used herein, "identifying a subject having cyclin D1- and/or USP2a-dependent prostate cancer" means selecting a subject on the basis that the subject has an aberrant (i.e., increased) expression of cyclin D1 and/or an aberrant (i.e., increased) expression of USp2a. For example, the prostate cancer can be detected by assaying for aberrant (i.e., an increased) cyclin D1 expression as compared to normal (non-cancerous) cells. In some embodiments, the prostate cancer can be detected by assaying for aberrant (i.e., an increased) USP2a expression as compared to normal (non-cancerous) cells. In some embodiments, the prostate cancer can be detected by assaying for aberrant (i.e., an increased) cyclin D1 and USP2a expression as compared to normal (non-cancerous) cells. The expression levels of cyclin D1- and/or USP2a may be determined by assaying for protein or mRNA levels using Western blotting, immunohistochemistry or microarray analysis.

In some embodiments, the subject is identified as having the cyclin D1- and/or USP2a-dependent prostate cancer by performing an analysis of a sample obtained of the subject. The sample is analyzed to determine the expression of USP2 and/or cyclin D1 using assays known in the art such as Western blotting, immunohistochemistry or microarray analysis. Examples of samples used include but are not limited to blood, urine, ejaculate, and tumor tissue.

Androden receptor, also known as NR3C4 (nuclear receptor subfamily 3, group C, member 4), is a type of nuclear receptor that is activated by binding of either of the androgenic hormones, testosterone or dihydrotestosterone, in the cytoplasm and then translocating into the nucleus. The main function of the androgen receptor is as a DNA-binding transcription factor that regulates gene expression; however, the androgen receptor has other functions as well. Androgen regulated genes are critical for the development and maintenance of the male sexual phenotype. Recently, USP12 was identified as a novel positive regulator of AR (Burska et al. J Biol Chem. 2013 Nov. 8; 288(45):32641-50). USP12 requires the interaction with two cofactors, UAF-1 and WDR20, for its enzymatic activity. USP12, in complex with UAF-1 and WDR20, deubiquitinates the AR to enhance receptor stability and transcriptional activity. Thus, USP12 acts in a pro-proliferative manner by stabilizing AR and enhancing its cellular function.

By "AR- and/or USP12-dependent prostate cancer" is meant a prostate cancer that has a cancer cell having an aberrant (i.e., an increased) AR expression and/or an aberrant (i.e., an increased) USP12 expression as compared to normal (non-cancerous) cells. In some embodiments, the AR and/or USP12 expression in cancer cells is increased (e.g., by at least 5%, 10%, 15%, 20%, 30%, 40%, 50%, 60%, 70%, 80%, 90%, or even 100%), as compared to normal (non-cancerous cells).

An AR- and/or USP12-dependent prostate cancer can be identified using assays well known and documented in the art. As used herein, "identifying a subject having AR- and/or USP12-dependent prostate cancer" means selecting a subject on the basis that the subject has an aberrant (i.e., increased) expression of AR and/or an aberrant (i.e., increased) expression of USP12. For example, the prostate cancer can be detected by assaying for aberrant (i.e., an increased) AR expression as compared to normal (non-cancerous) cells. In some embodiments, the prostate cancer can be detected by assaying for aberrant (i.e., an increased) USP12 expression as compared to normal (non-cancerous) cells. In some embodiments, the prostate cancer can be detected by assaying for aberrant (i.e., an increased) AR and USP12 expression as compared to normal (non-cancerous) cells. The expression levels of AR and/or USP12 may be determined by assaying for protein or mRNA levels using Western blotting, immunohistochemistry or microarray analysis.

In some embodiments, the subject is identified as having the AR- and/or USP12-dependent prostate cancer by performing an analysis of a sample obtained of the subject. The sample is analyzed to determine the expression of USP12 and/or AR using assays known in the art such as Western blotting, immunohistochemistry or microarray analysis. Examples of samples used include but are not limited to blood, urine, ejaculate, and tumor tissue.

Prostate cancer is a complex disease primarily characterized by dependence on androgen receptor (AR) signaling. Androgen receptor (AR) is the major therapeutic target in aggressive prostate cancer. However, targeting AR alone can result in drug resistance and disease recurrence. Aspects of the invention provide a method for treating prostate cancer resistant to androgen receptor (AR) inhibitor therapy. The method comprises: administering to a subject in need thereof a compound according to Formula I:

Formula I

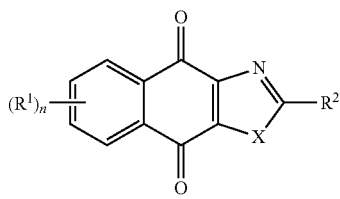

wherein
X is O, S, or NR³;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —$C(=O)R^B$; —$C(=O)N(R^B)_2$; —$CO_2R^B$; —CN; —SCN; —$SR^B$; —$SOR^B$; —$SO_2R^B$; —$NO_2$; —$N_3$; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; —$NR^BC(=O)OR^B$; or —$C(R^B)_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or a heteroarylthio moiety;

or a pharmaceutically acceptable salt thereof,
in an amount effective to treat the prostate cancer resistant to androgen receptor (AR) inhibitor therapy.

In certain embodiments, a compound of Formula I is of the formula:

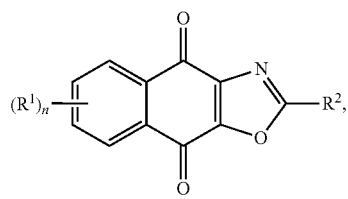

or a pharmaceutically acceptable salt thereof.

In certain embodiments, a compound of Formula I is of the formula:

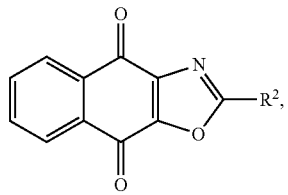

or a pharmaceutically acceptable salt thereof.

In certain embodiments, a compound of Formula I is of the formula:

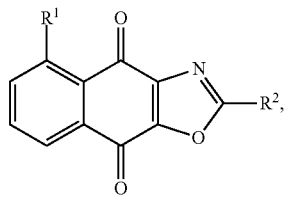

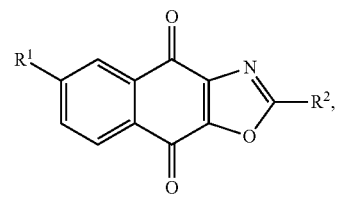

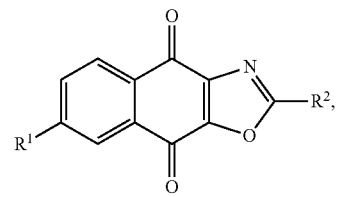

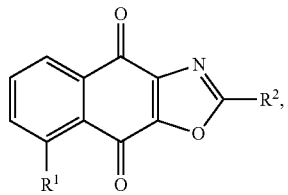

or a pharmaceutically acceptable salt thereof.

In certain embodiments, a compound of Formula I is of the formula:

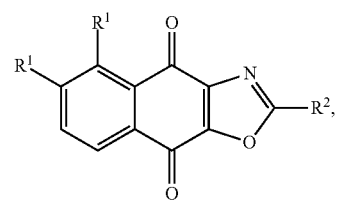

-continued

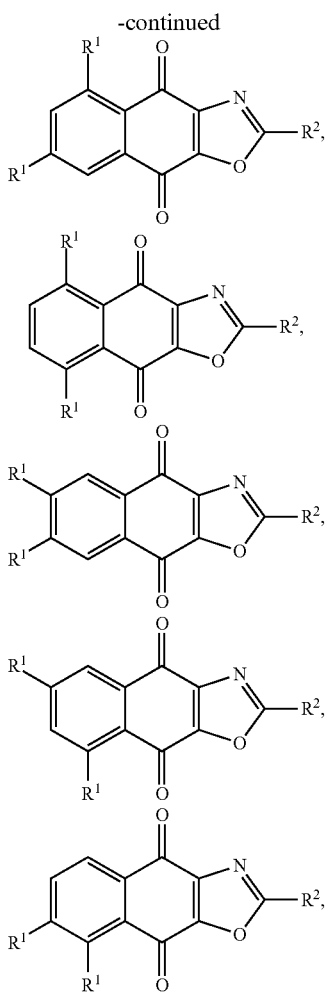

or a pharmaceutically acceptable salt thereof.

In certain embodiments, a compound of Formula I is of the formula:

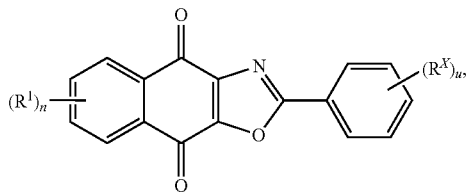

or a pharmaceutically acceptable salt thereof, wherein:

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and u is 0, 1, 2, 3, 4, or 5.

In certain embodiments, a compound of Formula I is of the formula:

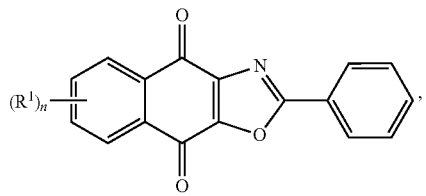

or a pharmaceutically acceptable salt thereof.

In certain embodiments, a compound of Formula I is of the formula:

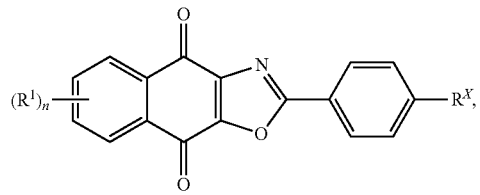

or a pharmaceutically acceptable salt thereof.

In certain embodiments, a compound of Formula I is of the formula:

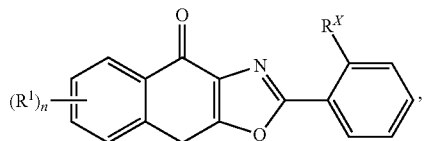

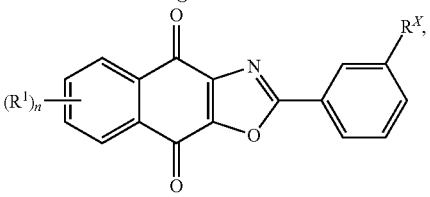

or a pharmaceutically acceptable salt thereof.

In certain embodiments, a compound of Formula I is of the formula:

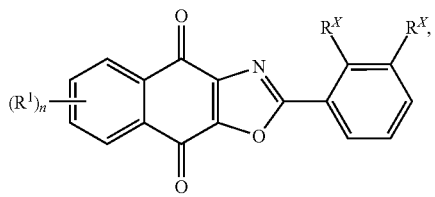

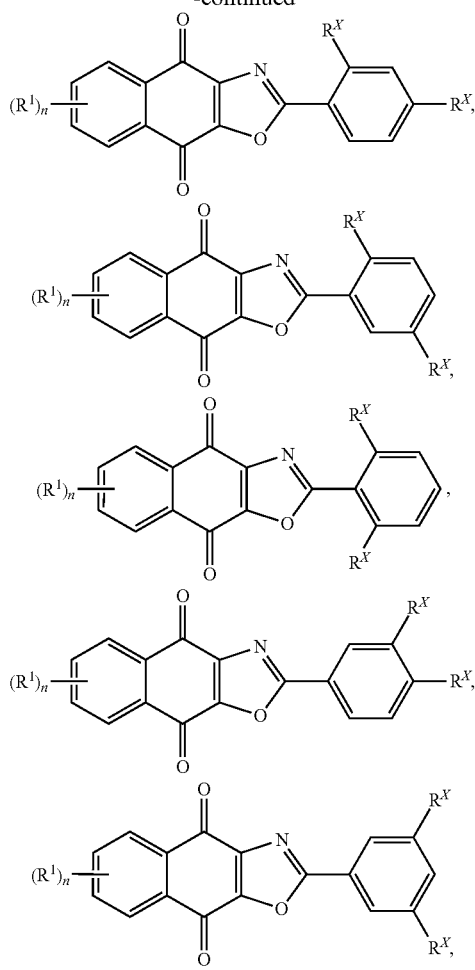

or a pharmaceutically acceptable salt thereof.

In certain embodiments, a compound of Formula I is of the formula:

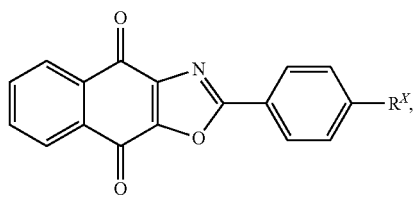

or a pharmaceutically acceptable salt thereof.

In certain embodiments, a compound of Formula I is of the formula:

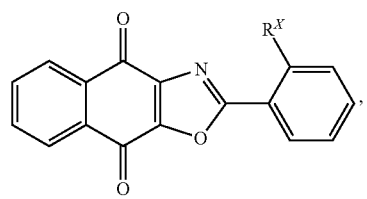

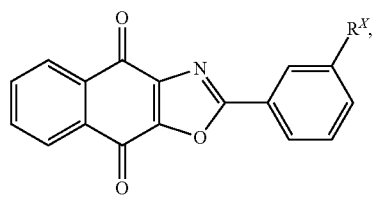

or a pharmaceutically acceptable salt thereof.

In certain embodiments, a compound of Formula I is of the formula:

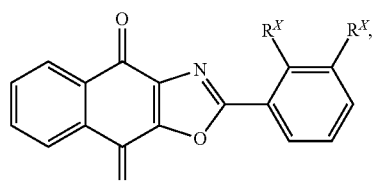

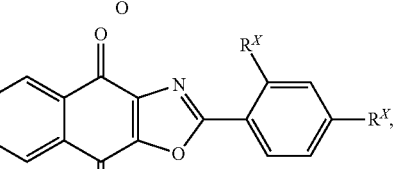

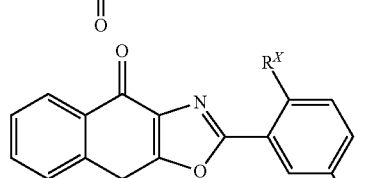

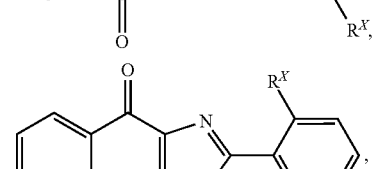

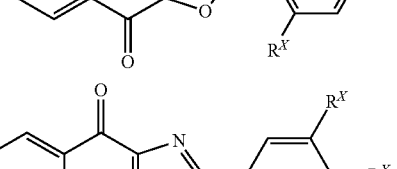

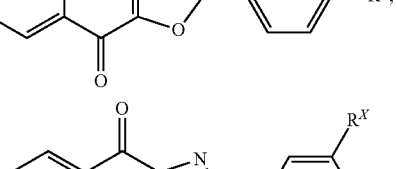

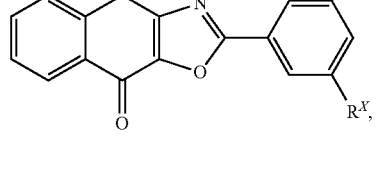

or a pharmaceutically acceptable salt thereof.

In certain embodiments, a compound of Formula I is of the formula:

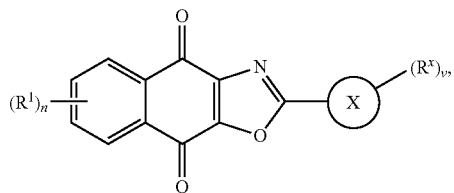

or a pharmaceutically acceptable salt thereof, wherein:

Ring X is a substituted or unsubstituted pyridyl ring;

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and v is 0, 1, 2, 3, or 4.

In certain embodiments, a compound of Formula I is of the formula:

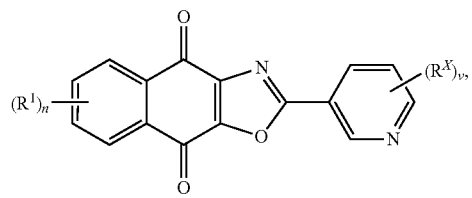

or a pharmaceutically acceptable salt thereof.

In certain embodiments, a compound of Formula I is of the formula:

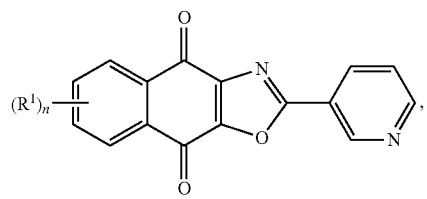

or a pharmaceutically acceptable salt thereof.

In certain embodiments, a compound of Formula I is of the formula:

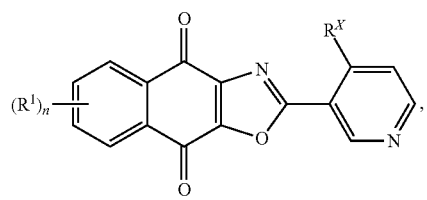

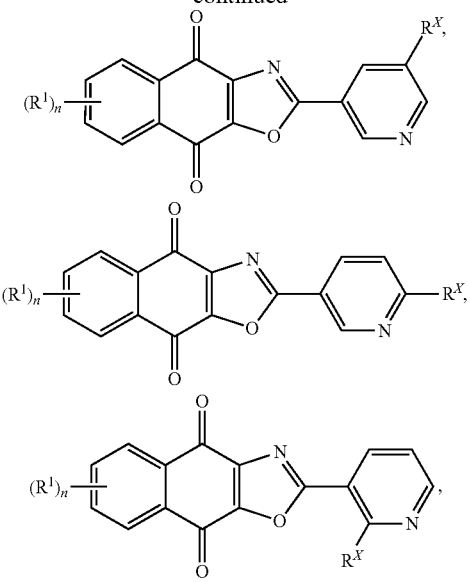

or a pharmaceutically acceptable salt thereof.

In certain embodiments, a compound of Formula I is of the formula:

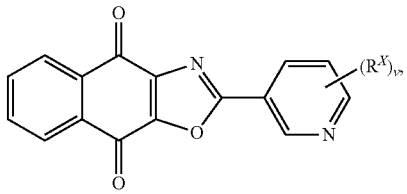

or a pharmaceutically acceptable salt thereof.

In certain embodiments, a compound of Formula I is of the formula:

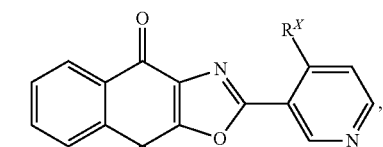

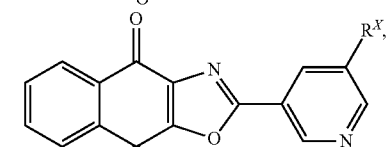

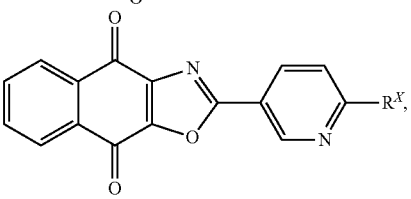

-continued

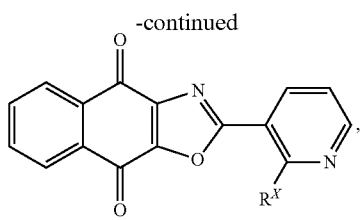

or a pharmaceutically acceptable salt thereof.

In certain embodiments, a compound of Formula I is of the formula:

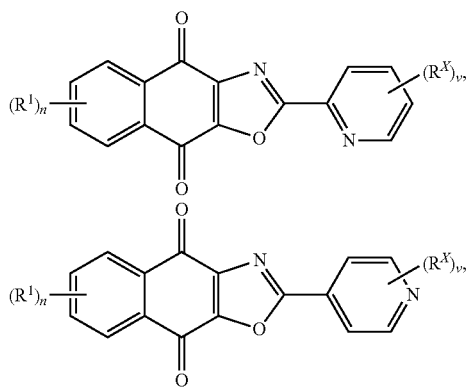

or a pharmaceutically acceptable salt thereof.

In certain embodiments, a compound of Formula I is of the formula:

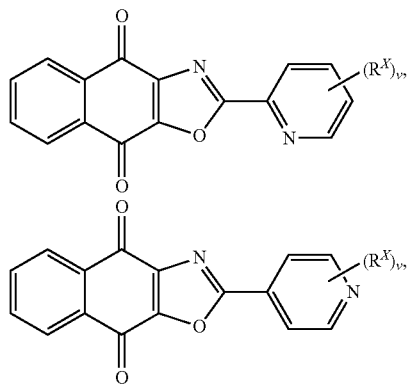

or a pharmaceutically acceptable salt thereof.

In certain embodiments, a compound of Formula I is of the formula:

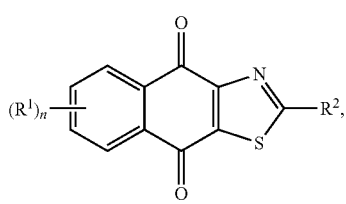

or a pharmaceutically acceptable salt thereof.

In certain embodiments, a compound of Formula I is of the formula:

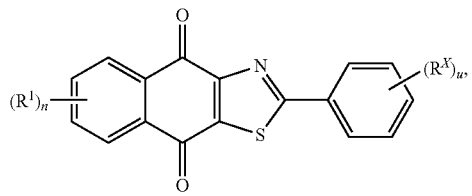

or a pharmaceutically acceptable salt thereof, wherein:

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and u is 0, 1, 2, 3, 4, or 5.

In certain embodiments, a compound of Formula I is of the formula:

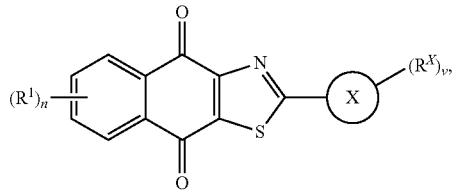

or a pharmaceutically acceptable salt thereof, wherein:

Ring X is a substituted or unsubstituted pyridyl ring;

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and v is 0, 1, 2, 3, or 4.

In certain embodiments, a compound of Formula I is of one of the following formulae:

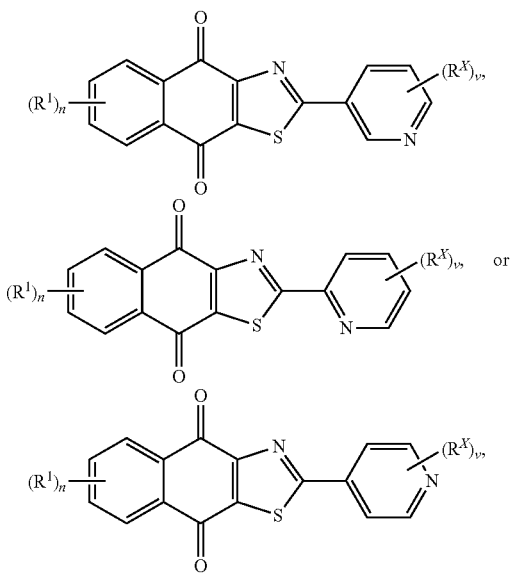

or a pharmaceutically acceptable salt thereof.

In certain embodiments, a compound of Formula I is of the formula:

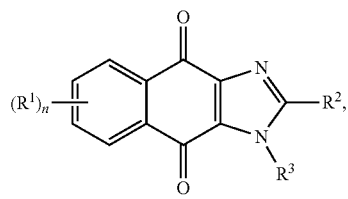

or a pharmaceutically acceptable salt thereof.

In certain embodiments, a compound of Formula I is of the formula:

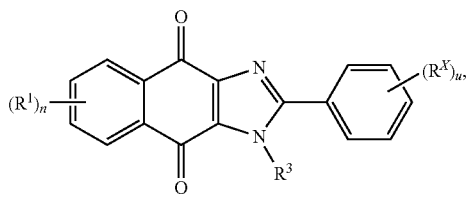

or a pharmaceutically acceptable salt thereof, wherein:

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and u is 0, 1, 2, 3, 4, or 5.

In certain embodiments, a compound of Formula I is of the formula:

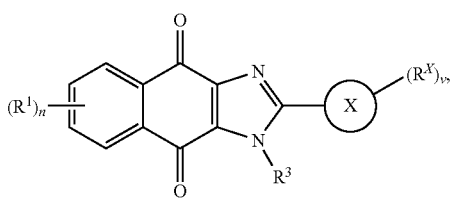

or a pharmaceutically acceptable salt thereof, wherein:

Ring X is a substituted or unsubstituted pyridyl ring;

each instance of $R^X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —$C(=O)R^A$; —$C(=O)N(R^A)_2$; —$CO_2R^A$; —CN; —SCN; —$SR^A$; —$SOR^A$; —$SO_2R^A$; —$NO_2$; —$N_3$; —$N(R^A)_2$; —$NHC(=O)R^A$; —$NR^AC(=O)N(R_A)_2$; —$OC(=O)OR^A$; —$OC(=O)R^A$; —$OC(=O)N(R^A)_2$; —$NR^AC(=O)OR^A$; or —$C(R^A)_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy, or heteroarylthio moiety; and v is 0, 1, 2, 3, or 4.

In certain embodiments, a compound of Formula I is of one of the following formulae:

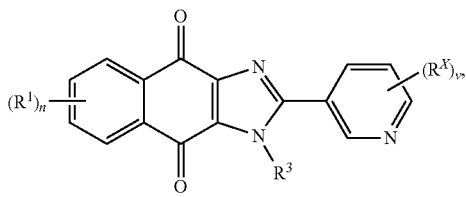

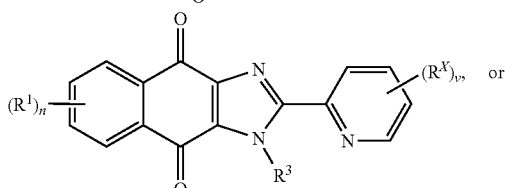

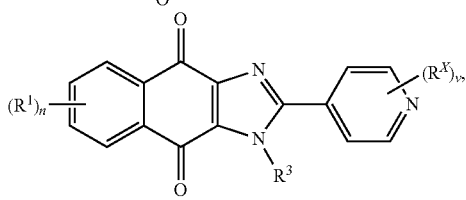

or a pharmaceutically acceptable salt thereof.

In certain embodiments, X is O. In certain embodiments, X is S or $NR^3$ (e.g., NH or NMe).

In certain embodiments, all instances of $R^1$ are the same. In certain embodiments, at least two instances of $R^1$ are different from each other. In certain embodiments, at least one instance of $R^1$ is halogen (e.g., F, Cl, Br, or I). In certain embodiments, at least one instance of $R^1$ is substituted or unsubstituted $C_{1-6}$ alkyl (e.g., Me). In certain embodiments, at least one instance of $R^1$ is —$OR^A$, optionally wherein $R^A$ is H or substituted or unsubstituted $C_{1-6}$ alkyl (e.g., Me).

In certain embodiments, n is 0. In certain embodiments, n is 1, 2, 3, or 4.

In certain embodiments, $R^2$ is substituted or unsubstituted aryl (e.g., substituted or unsubstituted, 6- to 14-membered aryl). In certain embodiments, $R^2$ is Ph. In certain embodiments, $R^2$ is substituted phenyl. In certain embodiments, $R^2$ is

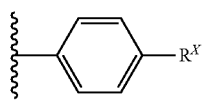

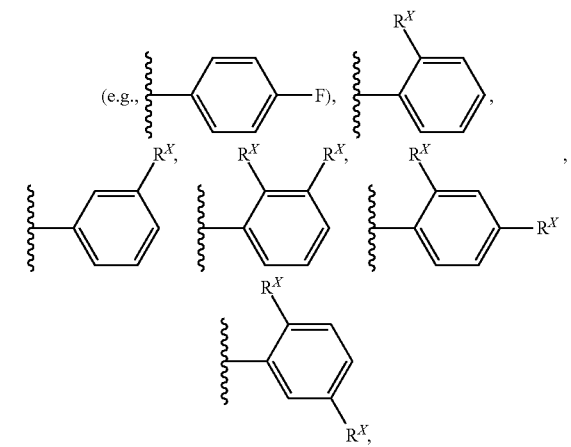

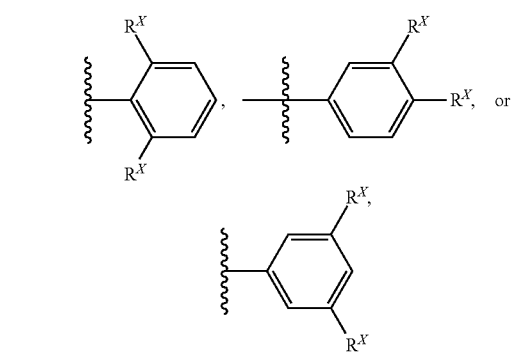

optionally wherein each instance of $R^X$ is independently halogen (e.g., F, Cl, Br, or I), substituted or unsubstituted $C_{1-6}$ alkyl (e.g., Me), or —$OR^A$, optionally wherein $R^A$ is H or substituted or unsubstituted $C_{1-6}$ alkyl (e.g., Me).

In certain embodiments, $R^2$ is substituted or unsubstituted heteroaryl (e.g., substituted or unsubstituted, 5- to 6-membered, monocyclic heteroaryl, wherein 1, 2, 3, or 4 atoms in the heteroaryl ring system are independently oxygen, nitrogen, or sulfur). In certain embodiments, $R^2$ is substituted or unsubstituted pyridyl. In certain embodiments, $R^2$ is substituted or unsubstituted 3-pyridyl (e.g.,

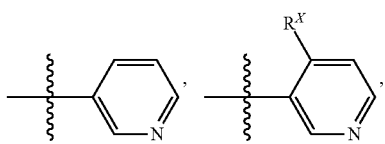

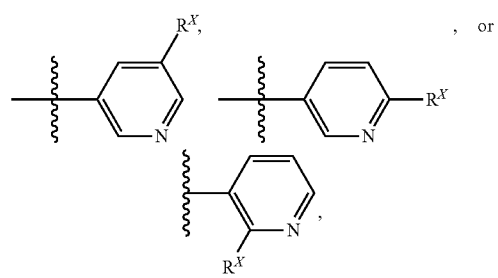

optionally wherein $R^X$ is halogen (e.g., F, Cl, Br, or I), substituted or unsubstituted $C_{1-6}$ alkyl (e.g., Me), or —$OR^A$, optionally wherein $R^A$ is H or substituted or unsubstituted $C_{1-6}$ alkyl (e.g., Me)). In certain embodiments, $R^2$ is substituted or unsubstituted 2-pyridyl (e.g.,

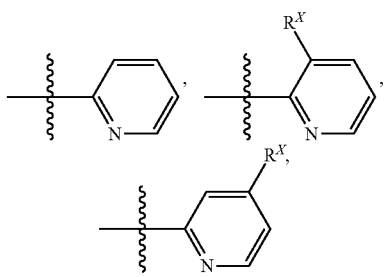

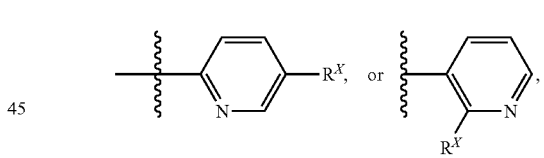

optionally wherein $R^X$ is halogen (e.g., F, Cl, Br, or I), substituted or unsubstituted $C_{1-6}$ alkyl (e.g., Me), or —$OR^A$, optionally wherein $R^A$ is H or substituted or unsubstituted $C_{1-6}$ alkyl (e.g., Me)) or 4-pyridyl (e.g.,

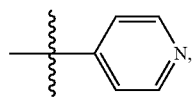

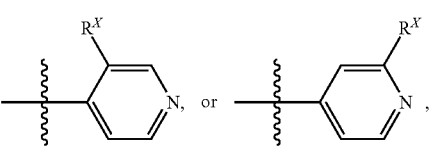

optionally wherein $R^X$ is halogen (e.g., F, Cl, Br, or I), substituted or unsubstituted $C_{1-6}$ alkyl (e.g., Me), or —$OR^A$, optionally wherein $R^A$ is H or substituted or unsubstituted $C_{1-6}$ alkyl (e.g., Me)). In certain embodiments, $R^2$ is substituted or unsubstituted pyrazinyl, substituted or unsubstituted pyrimidinyl, or substituted or unsubstituted pyridazinyl. In certain embodiments, $R^2$ is substituted or unsubstituted pyrrolyl, furanyl, thienyl, imidazolyl, oxazolyl, isoxazolyl, thiazolyl, isothiazolyl, triazolyl, oxadiazolyl, thiadiazolyl, or tetrazolyl.

In certain embodiments, all instances of $R^X$ are the same. In certain embodiments, at least two instances of $R^X$ are different from each other. In certain embodiments, at least one instance of $R^X$ is halogen. In certain embodiments, at least one instance of $R^X$ is F. In certain embodiments, at least one instance of $R^X$ is Cl, Br, or I. In certain embodiments, at least one instance of $R^X$ is substituted or unsubstituted $C_{1-6}$ alkyl (e.g., Me). In certain embodiments, at least one instance of $R^X$ is —$OR^A$, optionally wherein $R^A$ is H or substituted or unsubstituted $C_{1-6}$ alkyl (e.g., Me).

In certain embodiments, u is 0. In certain embodiments, u is 1. In certain embodiments, u is 2, 3, 4, or 5.

In certain embodiments, v is 0. In certain embodiments, v is 1, 2, 3, or 4.

In certain embodiments, $R^3$ is hydrogen, a protecting group, an aliphatic moiety, a heteroaliphatic moiety, an acyl moiety; an aryl moiety; a heteroaryl moiety; alkoxy; aryloxy; alkylthio; arylthio. In certain embodiments, $R^3$ is hydrogen. In certain embodiments, $R^3$ is a protecting group. In certain embodiments, $R^3$ is an aliphatic moiety. In certain embodiments, $R^3$ is a heteroaliphatic moiety. In certain embodiments, $R^3$ is an acyl moiety.

Exemplary compounds of Formula I include, but are not limited to, compounds 527, 019A, 043, and pharmaceutically acceptable salts thereof.

Examples of AR inhibitors include but are not limited to Casodex (bicalutamide), Xtandi (Enzalutamide), Flutamide, and Nilandron (Nilutamide). Cancers may be diagnosed as resistant to AR inhibitor therapy after treatment with these inhibitors has commenced. Alternatively, cancers may be diagnosed as AR inhibitor resistant prior to initiation of treatment with such compounds (for example, based on biomarker detection Kohli et al. Adv Urol. 2012; 2012:781459). Resistance in the tumor may occur after, e.g., 6 months or longer of AR inhibitor treatment. Alternatively, resistance of the tumor may be diagnosed less than 6 months after AR inhibitor treatment has commenced. Diagnosis of AR inhibitor resistance may be accomplished by way of monitoring tumor progression during AR inhibitor treatment. Tumor progression may be determined by comparison of tumor status between time points after treatment has commenced or by comparison of tumor status between a time point after treatment has commenced to a time point prior to initiation of AR inhibitor treatment. Tumor progression may be monitored during AR inhibitor treatment visually, for example, by means of radiography, for example, X-ray, CT scan, or other monitoring methods known to the skilled artisan, including palpitation of the cancer or methods to monitor tumor biomarker levels (such as levels of PSA, USP2, USP12, cyclin D1 and/or AR). Progression of the cancer during treatment with AR inhibitor indicates AR inhibitor resistance. A rise in level of tumor biomarkers indicates tumor progression. Thus, a rise in tumor biomarker levels during treatment with AR inhibitor indicates AR inhibitor resistance. Detection of new tumors or detection of metastasis indicates tumor progression. Cessation of tumor shrinkage indicates tumor progression. Growth of the cancer is indicated by, for example, increase in tumor size, metastasis or detection of new cancer, and/or a rise in tumor biomarker levels.

The compound can be administered to the subject using any suitable route of administration. Such routes of administration can include oral, intravenous, intramuscular, intraperitoneal, intravesical, intracisternal, other direct injection (e.g., into a tumor), topical, aerosol to lung, rectal, vaginal, and other mucosal.

An "effective amount" of compounds of Formula I, or a compound of Formula A, An-1, An-2, An-3, Ac-1, Ac-2, and Ac-3 refers to an amount sufficient to elicit the desired biological response, i.e., treating the NSCLC or treating the prostate cancer. As will be appreciated by those of ordinary skill in this art, the effective amount of compounds of Formula I, or a compound of Formula A, An-1, An-2, An-3, Ac-1, Ac-2, and Ac-3 may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more symptoms associated with a NSCLC or a prostate cancer. In the treatment of NSCLC or prostate cancer, such terms may refer to reduction in tumor mass or cell numbers.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg. As used herein, the term "treat" means to reduce or ameliorate a disease or condition by a detectable amount or degree. The term "treat" as used herein refers to both complete and partial treatment. In the context of cancer, the term "treat" as used herein thus can refer to complete or partial remission of a cancer. For example, treating a tumor may be manifest as a halted or slowed progression in the size or volume of a tumor, a decrease in the size or volume of a tumor, or complete resolution of a tumor.

Pharmaceutical Composition

Certain aspects of the invention provide pharmaceutical compositions comprising a compounds of Formula A, An-1, An-2, An-3, Ac-1, Ac-2, or Ac-3 described herein and a pharmaceutically acceptable carrier. In some embodiments, the compound is selected from the group consisting of

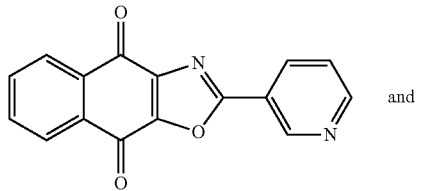

(019A)

and

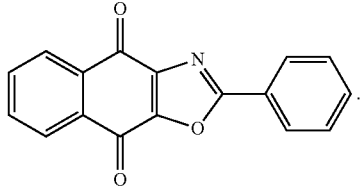

(043)

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the active agent can be administered to a subject by any mode that delivers the active agent to the desired surface. Administering the pharmaceutical composition of the present invention may be accomplished by any means known to the skilled artisan. Preferred routes of administration include but are not limited to oral, parenteral, intramuscular, intranasal, sublingual, intratracheal, and inhalation.

For oral administration, the compounds (e.g., compounds of Formula A, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the active agent (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the active agent (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the active agent or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the active agents (or derivatives thereof). The active agent (or derivative) is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of active agent (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified active agent may also be prepared in different formulations depending on the type of chemical modification or the type of device employed.

Formulations suitable for use with a nebulizer, either jet or ultrasonic, will typically comprise active agent (or derivative) dissolved in water at a concentration of about 0.1 to 25 mg of biologically active agent per mL of solution. The formulation may also include a buffer and a simple sugar (e.g., for active agent stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device will generally comprise a finely divided powder containing the active agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing active agent (or derivative) and may also include a bulking agent, such as lactose, sorbitol, sucrose, or mannitol in amounts which facilitate dispersal of the powder from the device, e.g., 50 to 90% by weight of the formulation. The active agent (or derivative) should most advantageously be prepared in particulate form with an average particle size of less than 10 micrometers (μm), most preferably 0.5 to 5 μm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The active agents and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The therapeutic agent(s), including specifically but not limited to the active agent, may be provided in particles. Particles as used herein means nano or microparticles (or in some instances larger) which can consist in whole or in part of the active agent or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the active agent in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The present invention is further illustrated by the following Examples, which in no way should be construed as further limiting. The entire contents of all of the references (including literature references, issued patents, published patent applications, and co-pending patent applications, if any) cited throughout this application are hereby expressly incorporated by reference.

EXAMPLES

Scheme 1. Preparation of compounds A-E.

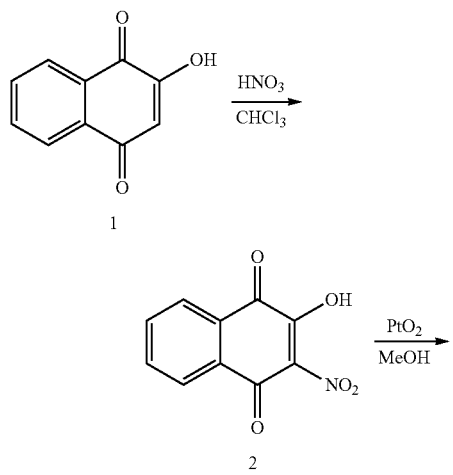

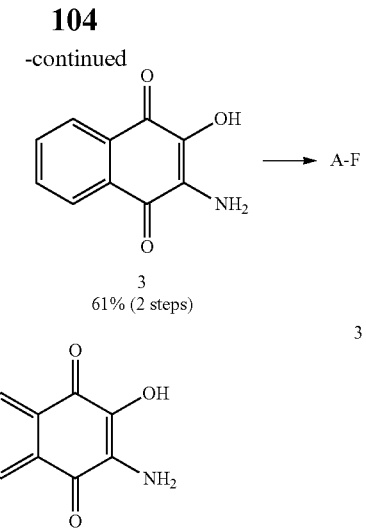

2-amino-3-hydroxynaphthalene-1,4-dione (3)

Fuming nitric acid (>90%) (5 mL) was added dropwise over 30 minutes using an additional funnel to a solution of quinone 1 (1.0 g) in 50 mL CHCl$_3$ and the reaction mixture stirred for 2 hours at which point LC-MS indicated complete consumption of starting material. The mixture was concentrated via rotary evaporation using minimal heat. The crude product was diluted with 5N HCl and the resulting yellow-orange ppt collected and utilized immediately in the following step. 2-hydroxy-3-nitronaphthalene-1,4-dione 2 (1.1 g) was diluted with methanol (50 mL) and nitrogen gas was bubbled through the solution for 20 minutes. PtO$_2$ (50 mg) was added and nitrogen bubbled through the solution for 15 minutes. Hydrogen gas was introduced via balloon and the reaction mixture stirred overnight at which point TLC analysis indicated complete consumption of starting material. Nitrogen was bubbled through the solution for 30 minutes then the reaction mixture was filtered through a pad of celite and washed repeatedly with methanol. The filtrate was concentrated to yield 707 mg of desired product as a purple solid in 61% yield. $^1$H NMR (400 MHz, d6-DMSO): δ 5.96 (2H, s), 7.64 (1H, apparent dt, J=1.6, 7.4), 7.70 (1H, apparent dt, J=1.2, 7.4), 7.82-7.86 (2H, m), 9.49 (1H, s). LRMS (M+H)$^+$: 190.22.

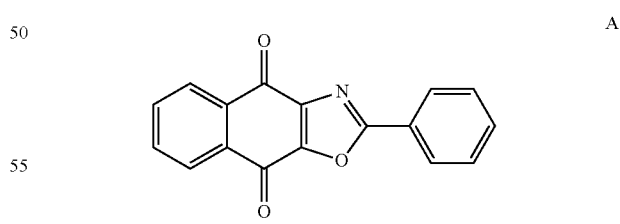

2-phenylnaphtho[2,3-d]oxazole-4,9-dione (A)

Intermediate 3 (500 mg, 1.0 eq), trimethylorthobenzoate (3.6 mL, 8.0 eq) and PPTS (66 mg, 0.1 eq) were combined and heated at 90° C. (oil bath) for 2 hours at which point LC-MS analysis indicated complete consumption of starting material. The reaction mixture was diluted with Et$_2$O and the resulting yellow ppt collected and washed with Et$_2$O and EtOAc and dried to yield desired product (472 mg, 65%) as a bright yellow fluffy solid. ¹H NMR (400 MHz, CDCl₃): δ 7.53-7.62 (3H, M), 7.81 (2H, dd, J=3.5, 5.9), 8.25 (1H, dd, J=3.3, 5.7), 8.29 (1H, dd, J=3.1, 5.9), 8.31-8.34 (2H, M). LRMS (M+H)⁺: 276.19.

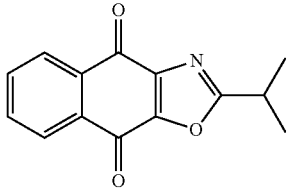

2-isopropylnaphtho[2,3-d]oxazole-4,9-dione (B)

Intermediate 3 (50 mg, 1.0 eq), 1,1,1-trimethoxy-2-methylpropane (620 µL, 15 eq) and PPTS (3 mg, 0.05 eq) were combined at heated at 90° C. for 90 min at which point LC-MS analysis indicated complete consumption of starting material. The reaction mixture was diluted with diethyl ether and water and the layers separated. The aqueous layer was extracted twice with diethyl ether and the combined organic extracts were washed 1× with brine, dried over anhydrous Na₂SO₄, filtered and concentrated. Purification of the crude mixture by silica gel chromatography (ISCO, EtOAc/Hex gradient) yielded 25 mg of desired product as a light orange solid. ¹H NMR (400 MHz, CDCl3): δ 1.49 (6H, d, J=7.0), 3.32 (1H, sep, J=7.0), 7.78 (1H, d, J=3.5), 7.79 (1H, d, J=3.5), 8.20-8.26 (2H, M). LRMS (M+H)⁺: 242.21.

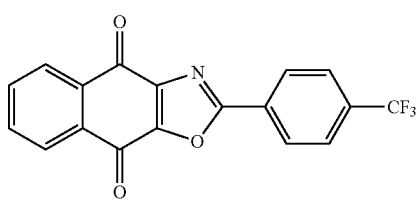

2-(4-(trifluoromethyl)phenyl)naphtho[2,3-d]oxazole-4,9-dione (C)

Amino alcohol 3 (277 mg, 1.0 eq), 4-fluorobenzoyl chloride (350 µL, 2.0 eq), In(OTf)₃ (41 mg, 0.05 eq) and dioxane (4.9 mL) were combined and heated at 150° C. for four hours in a microwave reactor (Biotage) at which point LC-MS showed generation of desired product. The reaction mixture was diluted with diethyl ether and water and the layers separated. The aqueous layer was extracted twice with diethyl ether and the combined organic extracts were washed 1× with brine, dried over anhydrous Na₂SO₄, filtered and concentrated. Purification of the crude mixture by silica gel chromatography (ISCO, EtOAc/Hex gradient) yielded 21 mg of desired product. LRMS (M+H)⁺: 344.14.

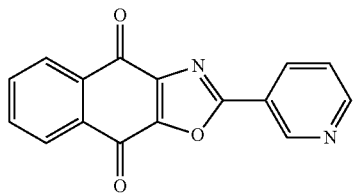

2-(pyridin-3-yl)naphtho[2,3-d]oxazole-4,9-dione (D)

Intermediate 3 (100 mg, 1.0 eq), nicotinic anhydride (210 mg, 2.0 eq), and In(OTf)₃ (61 mg, 0.2 eq) were combined and xylenes (2.7 mL) added. The reaction mixture was heated at 150° C. in a microwave reactor (Biotage) for 6 hours then diluted with H₂0 and CH₂Cl₂. The layers were separated and aqueous layer extracted 2× with CH₂Cl₂. The combined organic extracts were washed with brine, dried over Na₂SO₄, filtered and concentrated. The crude product was purified by silica gel chromatography twice to yield 28 mg (19% yield) of the desired product as a light brown powder. ¹H NMR (400 MHz, CDCl3): 7.52 (1H, dd, J=5.1, 8.2), 7.82 (2H, m), 8.29 (2H, M), 8.59 (1H, apparent dt, J=2.0, 8.2), 8.85 (1H, dd, J=1.6, 4.7), 9.55 (1H, d, J=2.4). LRMS (M+H)⁺: 277.16.

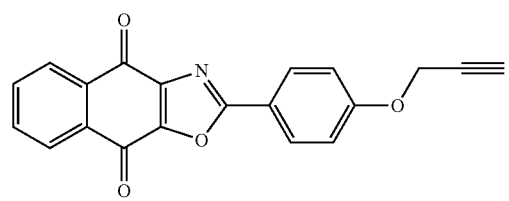

2-(4-(prop-2-yn-1-yloxy)phenyl)naphtho[2,3-d]oxazole-4,9-dione (E)

Intermediate 3 (200 mg, 1.0 eq), 4-(prop-2-yn-1-yloxy) benzoyl chloride (1.0 g, 5.0 eq), and H₂SO₄ (catalytic) in CH₂Cl₂ was refluxed for 16 hours to yield mono- and di-acylated intermediates. The crude intermediates were refluxed in acetic acid for 16 hours at which point LC-MS indicated approximately 20% conversion to desired product. The reaction mixture was concentrated and the crude product purified by preparative HPLC to give 7 mg of desired product. LRMS (M+H)⁺: 330.21.

FIG. 1 shows pharmacokinetic data which demonstrates that inhibitory serum concentrations of 019A can be achieved in mice by IV, IP, or oral (PO) administration of drugs.

Figure 2:
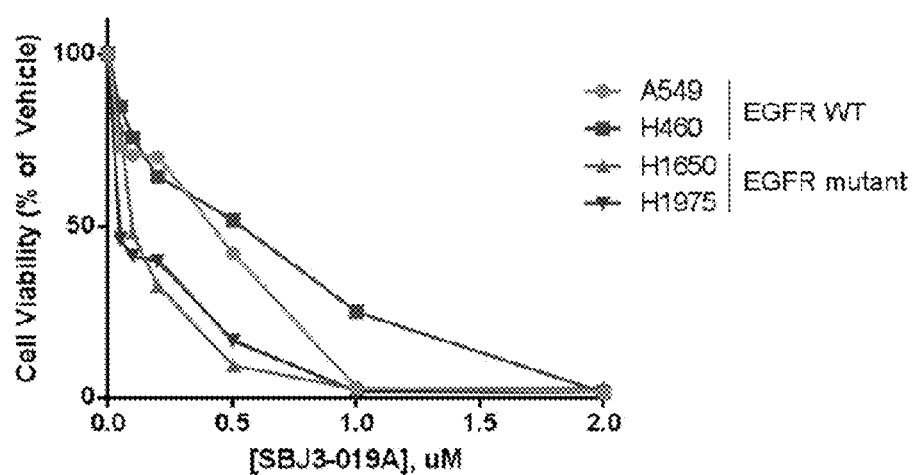
FIG. 2 shows that 019A has selective killing (cytotoxicity) for lung cancer cell lines which express activated EGF-receptor, for example, by promoting the degradation of the constitutively activated EGFR. The indicated human non-small cell lung cancer (NSCLC) lines were incubated with the indicated concentrations of the DUB inhibitor (019A) for twenty-four hours, and cell viability was measured.

FIG. 2 shows that 019A has selective killing (cytotoxicity) for lung cancer cell lines which express activated EGF-receptor, for example, by promoting the degradation of the constitutively activated EGFR. The indicated human non-small cell lung cancer (NSCLC) lines were incubated with the indicated concentrations of the DUB inhibitor (019A) for twenty-four hours, and cell viability was measured.

Figure 3:
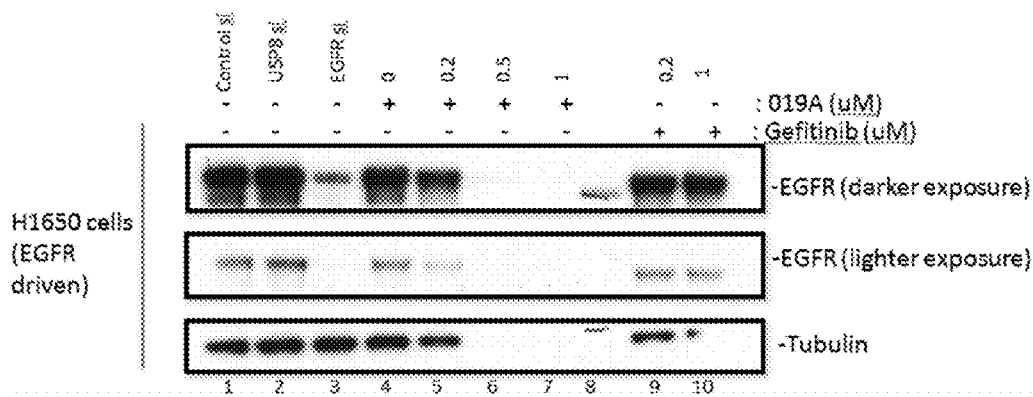
FIG. 3 shows that the 019A inhibitor promotes the degradation of activated EGFR. Hence, 019A is an effective anticancer drug for treating activated EGFR-driven lung cancers, even those cancers that become resistant to kinase-inhibitor therapy. Specifically, the NSCLC line H1650, which is driven by a constitutively-activated EGFR, was treated with the indicated concentrations of the PAN-DUB inhibitor SJB-019A and/or the kinase inhibitor Gefitinib. After 24 hours, cells were lysed and the total cellular proteins were electrophoresed by standard PAGE methods. Proteins were immunoblotted and probed with commercially available polyclonal antisera to EGFR or Tubulin.

FIG. 3 shows that the 019A inhibitor promotes the degradation of activated EGFR. Hence, 019A is an effective anticancer drug for treating activated EGFR-driven lung cancers, even those cancers that become resistant to kinase-inhibitor therapy. Specifically, the NSCLC line H1650, which is driven by a constitutively-activated EGFR, was treated with the indicated concentrations of the PAN-DUB inhibitor SJB-019A and/or the kinase inhibitor Gefitinib. After 24 hours, cells were lysed and the total cellular proteins were electrophoresed by standard PAGE methods. Proteins were immunoblotted and probed with commercially available polyclonal antisera to EGFR or Tubulin. Conclusion: the PAN-DUB inhibitor promotes the degradation of the EGFR, at least in part, by inhibition of USP8 which is expressed in these cells. The dose of the inhibitor that reduce the viability of the NSCLC (less than 0.5 μm, see FIG. 2) correlates with the amount of drug required to degrade EGFR (between 0.2-0.5 μm).

Figure 4:
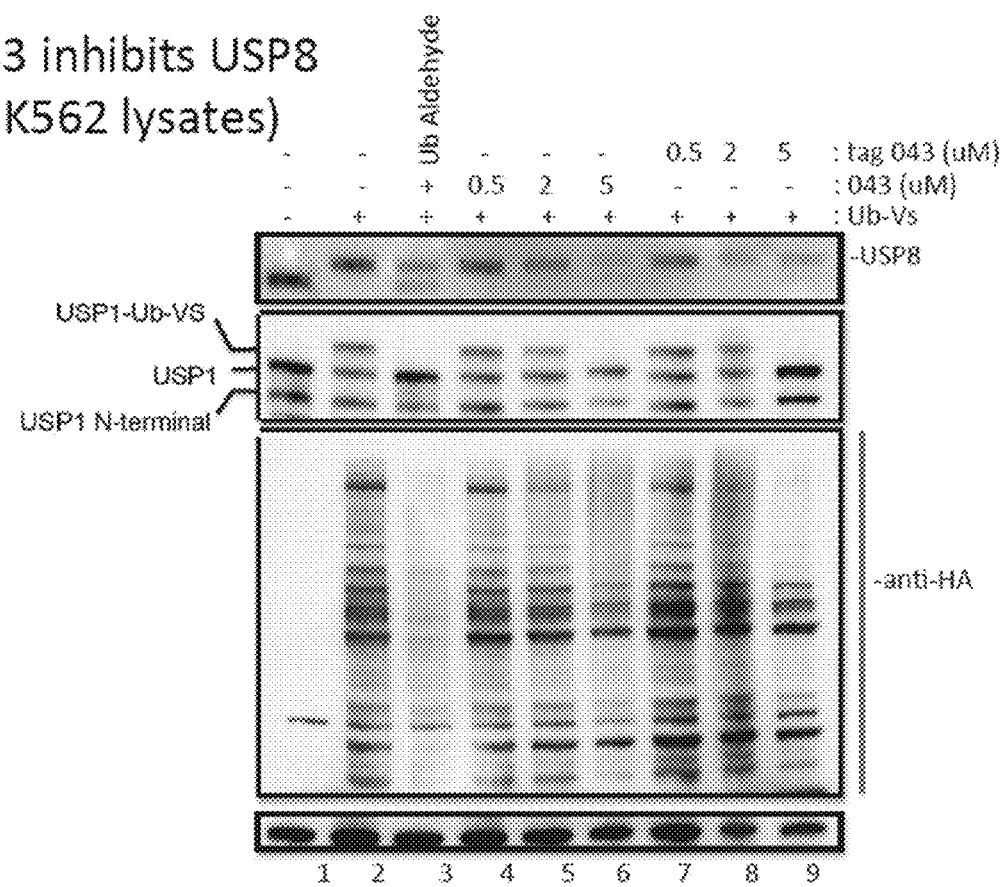
FIG. 4 shows that USP1 inhibitor, SJB043 inhibits the USP8 enzyme. Human leukemia cells (K652 cell line) express USP8, USP1, and other DUBs. In this experiment, K562 cells were lysed, and total cellular proteins were incubated with the affinity reagent, Ub-VS (vinyl sulfone) which covalently binds to active USPs. As indicated, the addition of Ub-VS causes an upward gel shift of active USP8 and active USP1 (lane 2). Pretreatment of the lysate with Ub-aldehyde, a known pan-DUB inhibitor, before treatment with Ub-VS (HA-tagged) blocks the upward shift (lane 3). Interestingly, in a dose dependent manner, the SJB043 drug (or a click-chemistry tagged version of SJB043) inhibits this binding of the Ub-VS reagent to the DUB. Taken together, these results indicate that SJB043 inhibits USP8, as well as USP1, and may account for the decrease in cyclin D1 expression in prostate cancer cells treated with the drug. A western blot is shown, immunoblotted with either anti-USP8, anti-USP1, or anti-HA.

FIG. 4 shows that USP1 inhibitor, SJB043 inhibits the USP8 enzyme. Human leukemia cells (K652 cell line) express USP8, USP1, and other DUBs. In this experiment, K562 cells were lysed, and total cellular proteins were incubated with the affinity reagent, Ub-VS (vinyl sulfone) which covalently binds to active USPs. As indicated, the addition of Ub-VS causes an upward gel shift of active USP8 and active USP1 (lane 2). Pretreatment of the lysate with Ub-aldehyde, a known pan-DUB inhibitor, before treatment with Ub-VS (HA-tagged) blocks the upward shift (lane 3). Interestingly, in a dose dependent manner, the SJB043 drug (or a click-chemistry tagged version of SJB043) inhibits this binding of the Ub-VS reagent to the DUB. Taken together, these results indicate that SJB043 inhibits USP8, as well as USP1, and may account for the decrease in EGFR expression in lung cancer cells treated with the drug. A western blot is shown, immunoblotted with either anti-USP8, anti-USP1, or anti-HA antibodies.

Figure 5:
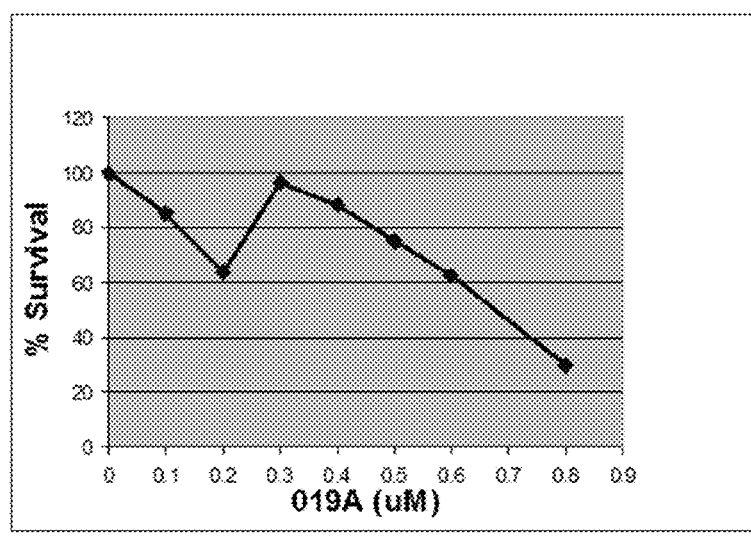
FIG. 5 shows that 019A promotes the killing of prostate cancer cells in the submicromolar range of drug concentration, for example by promoting the degradation of upregulated Cyclin D1. A human prostate cancer cell line was incubated with the indicated concentration of DUB inhibitor for 24 hours, and viability was then measured.
Figure 7:
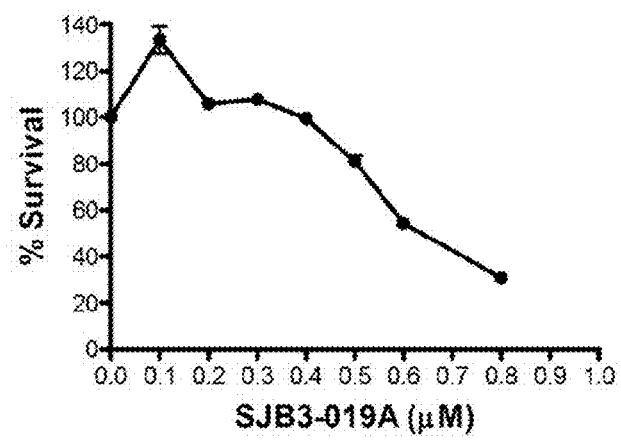
FIG. 7 shows that 019A promotes the killing of prostate cancer cells in the submicromolar range of drug concentration, for example by promoting the degradation of upregulated Cyclin D1. A human prostate cancer cell line was incubated with the indicated concentration of DUB inhibitor for 24 hours, and viability was then measured.

FIG. 5 and FIG. 7 show that 019A promotes the killing of prostate cancer cells in the submicromolar range of drug concentration, for example by promoting the degradation of upregulated Cyclin D1 or AR. A human prostate cancer cell line was incubated with the indicated concentration of DUB inhibitor for 24 hours, and viability was then measured.

Figure 6:
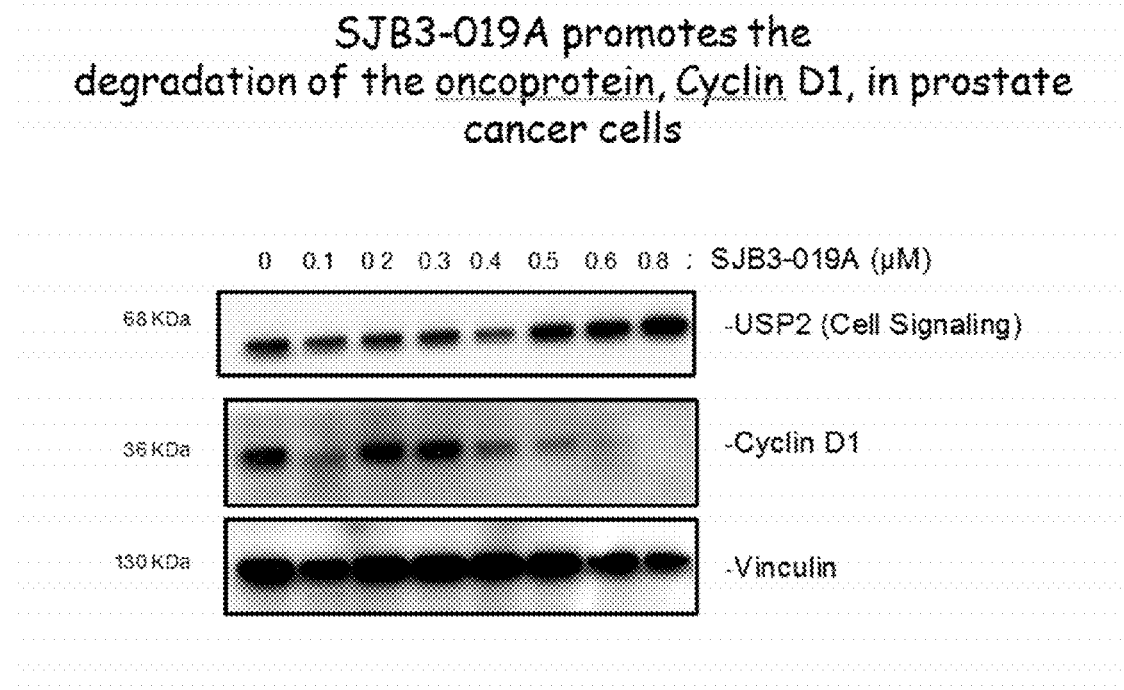
FIG. 6 shows that 019A (DUB inhibitor) promotes the degradation of the oncoprotein, Cyclin D1, in a prostate cancer cell line, in a drug dose-dependent manner. Specifically, a human prostate cancer cell line was exposed to the indicated concentrations of PAN-DUB inhibitor, 019A, for 24 hours. Thereafter, cells were lysed, and total cellular proteins were electrophoresed and immunoblotted. Proteins were probed with anti-USP2, anti-Cyclin D1, and anti-vinculin.
Figure 8:
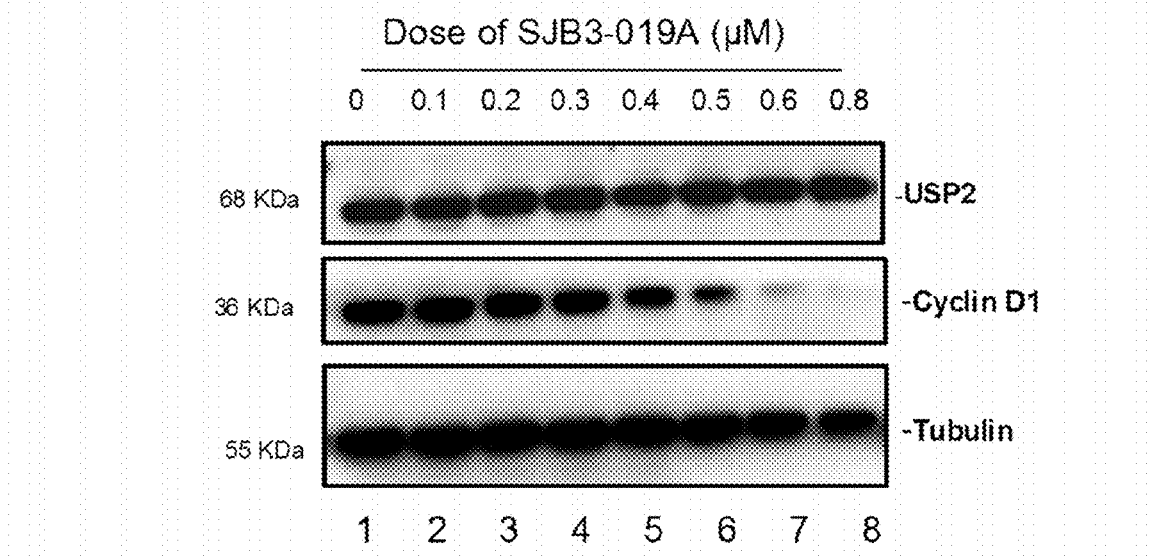
FIG. 8 shows that 019A (DUB inhibitor) promotes the degradation of the oncoprotein, Cyclin D1, in a prostate cancer cell line, in a drug dose-dependent manner. Specifically, a human prostate cancer cell line was exposed to the indicated concentrations of PAN-DUB inhibitor, 019A, for 24 hours. Thereafter, cells were lysed, and total cellular proteins were electrophoresed and immunoblotted. Proteins were probed with anti-USP2, anti-Cyclin D1, and anti-tubulin.

FIG. 6 and FIG. 8 show that 019A (DUB inhibitor) promotes the degradation of the oncoprotein, Cyclin D1, in a prostate cancer cell line, in a drug dose-dependent manner. Specifically, a human prostate cancer cell line was exposed to the indicated concentrations of PAN-DUB inhibitor, 019A, for 24 hours. Thereafter, cells were lysed, and total cellular proteins were electrophoresed and immunoblotted. Proteins were probed with anti-USP2, anti-Cyclin D1, and anti-Tubulin antibodies or anti-vinculin antibodies. Conclusion: the PAN-DUB inhibitor promotes the dose-dependent degradation of Cyclin D1, consistent with the dose-dependent killing of the cells by the drug. The dose of the inhibitor that reduce the viability of the prostate cancer cells (about 0.5 to 0.8 μm, see FIG. 5 and FIG. 7) correlates with the amount of drug required to degrade cyclin D1 (about 0.5 to 0.8 μm). The inhibitor does not affect USP2a expression, but inhibits USP2a function as demonstrated by the degradation of cyclin D1.

Figure 9:
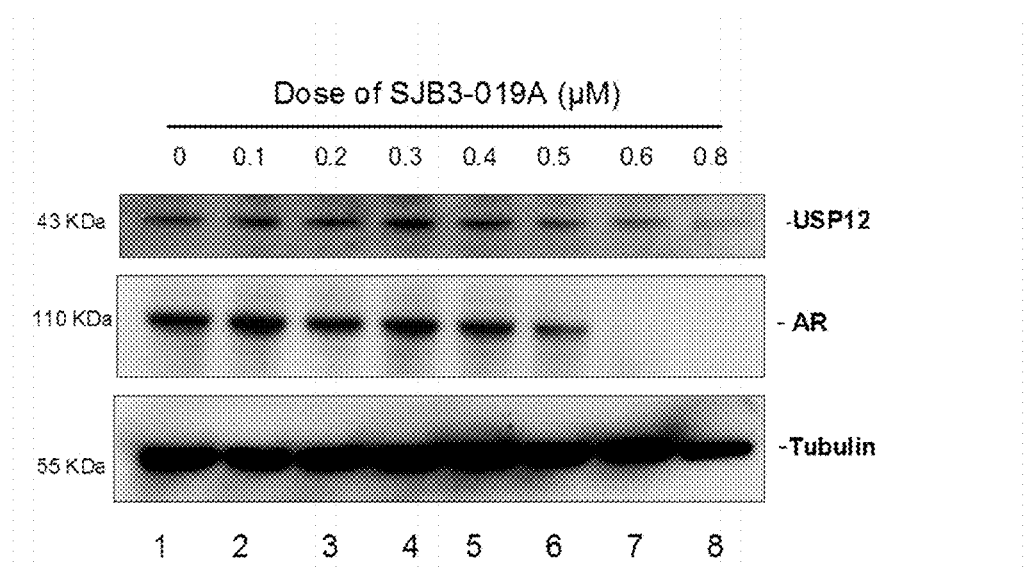
FIG. 9 shows that 019A (DUB inhibitor) promotes degradation of the oncoprotein, AR, in a prostate cancer cell line, in a drug dose-dependent manner. Specifically, a human prostate cancer cell line was exposed to the indicated concentrations of PAN-DUB inhibitor, 019A, for 24 hours. Thereafter, cells were lysed, and total cellular proteins were electrophoresed and immunoblotted. Proteins were probed with anti-USP12, anti-AR, and anti-Tubulin antibodies.

FIG. 9 shows that 019A (DUB inhibitor) promotes the degradation of the oncoprotein, AR, in a prostate cancer cell line, in a drug dose-dependent manner. Specifically, a human prostate cancer cell line was exposed to the indicated concentrations of PAN-DUB inhibitor, 019A, for 24 hours. Thereafter, cells were lysed, and total cellular proteins were electrophoresed and immunoblotted. Proteins were probed with anti-USP12, anti-AR, and anti-Tubulin antibodies. Conclusion: the PAN-DUB inhibitor promotes the dose-dependent degradation of AR, consistent with the dose-dependent killing of the cells by the drug. The dose of the inhibitor that reduce the viability of the prostate cancer cells (about 0.5 to 0.8 μm, see FIG. 5 and FIG. 7) correlates with the amount of drug required to degrade AR (about 0.6 to 0.8 μm). The inhibitor degrades USP12 protein and inhibits its function as demonstrated by the degradation of AR.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:
1. A method for treating non-small cell lung cancer, the method comprising:
 administering to a subject in need thereof a compound according to Formula A:

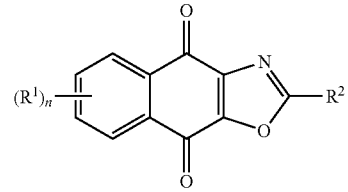

Formula A or pharmaceutically acceptable salt thereof,
wherein
 n is 0, 1, 2, 3, or 4;
 each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{41}$; —C(=O)$R^{41}$; —C(=O)N($R^{41}$)$_2$; —CO$_2R^{41}$; —CN; —SCN; —S$R^{41}$; —SO$R^{41}$; —SO$_2R^{41}$; —NO$_2$; —N$_3$; —N($R^{41}$)$_2$; —NHC(=O)$R^{41}$; —N$R^{41}$C(=O)N($R^{41}$)$_2$; —OC(=O)O$R^{41}$; —OC(=O)$R^{41}$; —OC(=O)N($R^{41}$)$_2$; —N$R^{41}$C(=O)O$R^{41}$; or —C($R^{41}$)$_3$;
 each occurrence of $R^{41}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{42}$, —N($R^{42}$)$_2$, —S$R^{42}$, —CN, —SCN, —C(=N$R^{42}$)$R^{42}$, —C(=N$R^{42}$)O$R^{42}$, —C(=N$R^{42}$)N($R^{42}$)$_2$, —C(=O)$R^{42}$, —C(=O)O$R^{42}$, —C(=O)N($R^{42}$)$_2$, —NO$_2$, —N$R^{42}$C(=O)$R^{42}$, —N$R^{42}$C(=O)O$R^{42}$, —N$R^{42}$C(=O)N($R^{42}$)$_2$, —OC(=O)$R^{42}$, —OC(=O)O$R^{42}$, or —OC(=O)N($R^{42}$)$_2$;
 each instance of $R^{42}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;

$R^2$ is cyclic or acyclic, branched or unbranched aliphatic; cyclic or acyclic, branched or unbranched heteroaliphatic; aryl; or heteroaryl; optionally substituted with m instances of $R^4$;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^B$, $-N(R^B)_2$, $-SR^B$, $-CN$, $-SCN$, $-C(=NR^B)R^B$, $-C(=NR^B)OR^B$, $-C(=NR^B)N(R^B)_2$, $-C(=O)R^B$, $-C(=O)OR^B$, $-C(=O)N(R^B)_2$, $-NO_2$, $-NR^BC(=O)R^B$, $-NR^BC(=O)OR^B$, $-NR^BC(=O)N(R^B)_2$, $-OC(=O)R^B$, $-OC(=O)OR^B$, or $-OC(=O)N(R^B)_2$;

each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring; and m is 0, 1, 2, 3, 4, or 5, in an amount effective to treat the non-small cell lung cancer.

2. A method for treating prostate cancer, the method comprising: administering to a subject in need thereof a compound according to Formula A:

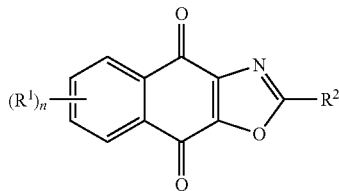

Formula A or pharmaceutically acceptable salt thereof,
wherein
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; $-OR^{A1}$; $-C(=O)R^{A1}$; $-C(=O)N(R^{A1})_2$; $-CO_2R^{A1}$; $-CN$; $-SCN$; $-SR^{A1}$; $-SOR^{A1}$; $-SO_2R^{A1}$; $-NO_2$; $-N_3$; $-N(R^{A1})_2$; $-NHC(=O)R^{A1}$; $-NR^{A1}C(=O)N(R^{A1})_2$; $-OC(=O)OR^{A1}$; $-OC(=O)R^{A1}$; $-OC(=O)N(R^{A1})_2$; $-NR^{A1}C(=O)OR^{A1}$; or $-C(R^{A1})_3$;

each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A2}$, $-N(R^{A2})_2$, $-SR^{A2}$, $-CN$, $-SCN$, $-C(=NR^{A2})R^{A2}$, $-C(=NR^{A2})OR^{A2}$, $-C(=NR^{A2})N(R^{A2})_2$, $-C(=O)R^{A2}$, $-C(=O)OR^{A2}$, $-C(=O)N(R^{A2})_2$, $-NO_2$, $-NR^{A2}C(=O)R^{A2}$, $-NR^{A2}C(=O)OR^{A2}$, $-NR^{A2}C(=O)N(R^{A2})_2$, $-OC(=O)R^{A2}$, $-OC(=O)OR^{A2}$, or $-OC(=O)N(R^{A2})_2$;

each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;

$R^2$ is cyclic or acyclic, branched or unbranched aliphatic; cyclic or acyclic, branched or unbranched heteroaliphatic; aryl; or heteroaryl; optionally substituted with m instances of $R^4$;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^B$, $-N(R^B)_2$, $-SR^B$, $-CN$, $-SCN$, $-C(=NR^B)R^B$, $-C(=NR^B)OR^B$, $-C(=NR^B)N(R^B)_2$, $-C(=O)R^B$, $-C(=O)OR^B$, $-C(=O)N(R^B)_2$, $-NO_2$, $-NR^BC(=O)R^B$, $-NR^BC(=O)OR^B$, $-NR^BC(=O)N(R^B)_2$, $-OC(=O)R^B$, $-OC(=O)OR^B$, or $-OC(=O)N(R^B)_2$;

each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring; and m is 0, 1, 2, 3, 4, or 5 in an amount effective to treat the prostate cancer.

3. The method of claim 1, wherein the compound according to Formula A is a compound having a formula of Formula An-1:

Formula An-1

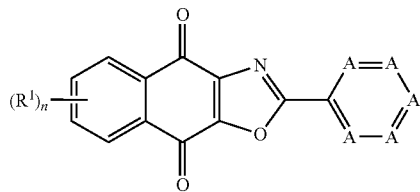

wherein
A is N or C—R⁴, wherein no more than two A groups can be N;
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{A1}$; —$C(=O)R^{A1}$; —$C(=O)N(R^{A1})_2$; —$CO_2R^{A1}$; —CN; —SCN; —$SR^{A1}$; —$SOR^{A1}$; —$SO_2R^{A1}$; —$NO_2$; —$N_3$; —$N(R^{A1})_2$; —$NHC(=O)R^{A1}$; —$NR^{A1}C(=O)N(R^{A1})_2$; —$OC(=O)OR^{A1}$; —$OC(=O)R^{A1}$; —$OC(=O)N(R^{A1})_2$; —$NR^{A1}C(=O)OR^{A1}$; or —$C(R^{A1})_3$;
each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2}$, —$N(R^{A2})_2$, —$SR^{A2}$, —CN, —SCN, —$C(=NR^{A2})R^{A2}$, —$C(=NR^{A2})OR^{A2}$, —$C(=NR^{A2})N(R^{A2})_2$, —$C(=O)R^{A2}$, —$C(=O)OR^{A2}$, —$C(=O)N(R^{A2})_2$, —$NO_2$, —$NR^{A2}C(=O)R^{A2}$, —$NR^{A2}C(=O)OR^{A2}$, —$NR^{A2}C(=O)N(R^{A2})_2$, —$OC(=O)R^{A2}$, —$OC(=O)OR^{A2}$, or —$OC(=O)N(R^{A2})_2$;
each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;
each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —$C(=NR^B)R^B$, —$C(=NR^B)OR^B$, —$C(=NR^B)N(R^B)_2$, —$C(=O)R^B$, —$C(=O)OR^B$, —$C(=O)N(R^B)_2$, —$NO_2$, —$NR^BC(=O)R^B$, —$NR^BC(=O)OR^B$, —$NR^BC(=O)N(R^B)_2$, —$OC(=O)R^B$, —$OC(=O)OR^B$, or —$OC(=O)N(R^B)_2$; and
each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring.

4. The method of claim 1, wherein the compound according to Formula A is a compound having a formula of Formula Ac-1:

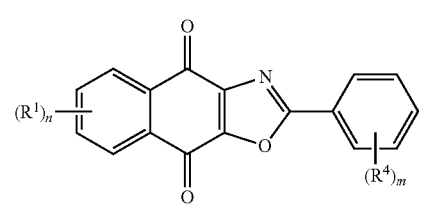

Formula Ac-1 wherein
n is 0, 1, 2, 3, or 4;
each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{A1}$; —$C(=O)R^{A1}$; —$C(=O)N(R^{A1})_2$; —$CO_2R^{A1}$; —CN; —SCN; —$SR^{A1}$; —$SOR^{A1}$; —$SO_2R^{A1}$; —$NO_2$; —$N_3$; —$N(R^{A1})_2$; —$NHC(=O)R^{A1}$; —$NR^{A1}C(=O)N(R^{A1})_2$; —$OC(=O)OR^{A1}$; —$OC(=O)R^{A1}$; —$OC(=O)N(R^{A1})_2$; —$NR^{A1}C(=O)OR^{A1}$; or —$C(R^{A1})_3$;
each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2}$, —$N(R^{A2})_2$, —$SR^{A2}$, —CN, —SCN, —$C(=NR^{A2})R^{A2}$, —$C(=NR^{A2})OR^{A2}$, —$C(=NR^{A2})N(R^{A2})_2$, —$C(=O)R^{A2}$, —$C(=O)OR^{A2}$, —$C(=O)N(R^{A2})_2$, —$NO_2$, —$NR^{A2}C(=O)R^{A2}$, —$NR^{A2}C(=O)OR^{A2}$, —$NR^{A2}C(=O)N(R^{A2})_2$, —$OC(=O)R^{A2}$, —$OC(=O)OR^{A2}$, or —$OC(=O)N(R^{A2})_2$;
each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;
each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^B$, —N(R$^B$)$_2$, —SR$^B$, —CN, —SCN, —C(=NR$^B$)R$^B$, —C(=NR$^B$)OR$^B$, —C(=NR$^B$)N(R$^B$)$_2$, —C(=O)R$^B$, —C(=O)OR$^B$, —C(=O)N(R$^B$)$_2$, —NO$_2$, —NR$^B$C(=O)R$^B$, —NR$^B$C(=O)OR$^B$, —NR$^B$C(=O)N(R$^B$)$_2$, —OC(=O)R$^B$, —OC(=O)OR$^B$, or —OC(=O)N(R$^B$)$_2$;

each instance of R$^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^B$ groups are joined to form a substituted or unsubstituted heterocyclic or substituted or unsubstituted heteroaryl ring; and m is 0, 1, 2, 3, 4, or 5.

5. The method of claim 1, wherein the compound according to Formula A is a compound selected from the group consisting of:

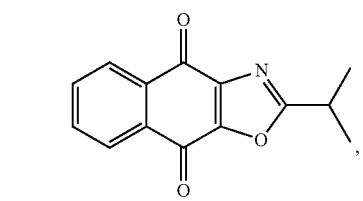
(1)

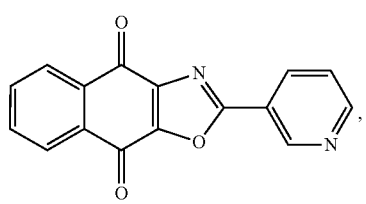
(2)

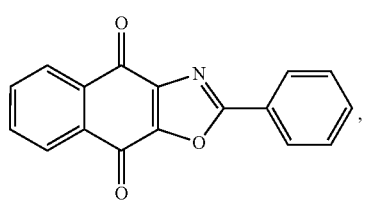
(3)

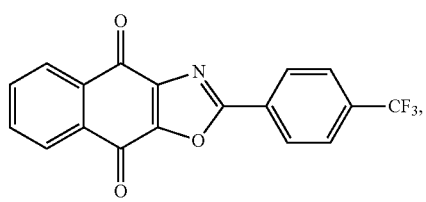
(4)

and

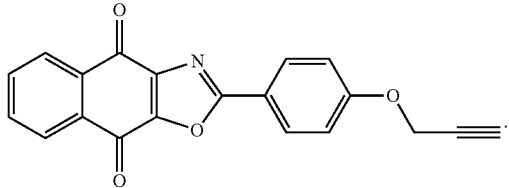
(5)

6. The method of claim 1, wherein the non-small cell lung cancer is resistant to at least one of gefitinib, erlotinib, and lapatinib.

7. The method of claim 1, wherein the non-small cell lung cancer is an epidermal growth factor receptor (EGFR)-mutant non-small cell lung cancer.

8. The method of claim 7, further comprising identifying the subject as having an EGFR-mutant non-small cell lung cancer.

9. The method of claim 2, wherein the compound according to Formula A is a compound having a formula of Formula An-1:

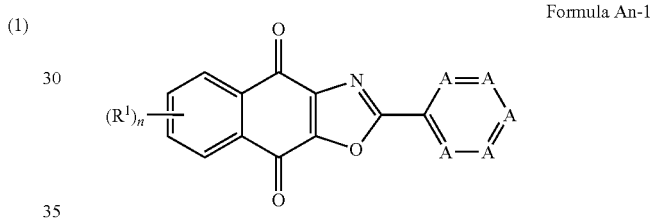
Formula An-1 wherein
A is N or C—R$^4$, wherein no more than two A groups can be N;
n is 0, 1, 2, 3, or 4;
each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^{41}$; —C(=O)R$^{41}$; —C(=O)N(R$^{41}$)$_2$; —CO$_2$R$^{41}$; —CN; —SCN; —SR$^{41}$; —SOR$^{41}$; —SO$_2$R$^{41}$; —NO$_2$; —N$_3$; —N(R$^{41}$)$_2$; —NHC(=O)R$^{41}$; —NR$^{41}$C(=O)N(R$^{41}$)$_2$; —OC(=O)OR$^{41}$; —OC(=O)R$^{41}$; —OC(=O)N(R$^{41}$)$_2$; —NR$^{41}$C(=O)OR$^{41}$; or —C(R$^{41}$)$_3$;
each occurrence of R$^{41}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{42}$, —N(R$^{42}$)$_2$, —SR$^{42}$, —CN, —SCN, —C(=NR$^{42}$)R$^{42}$, —C(=NR$^{42}$)OR$^{42}$, —C(=NR$^{42}$)N(R$^{42}$)$_2$, —C(=O)R$^{42}$, —C(=O)OR$^{42}$, —C(=O)N(R$^{42}$)$_2$, —NO$_2$, —NR$^{42}$C(=O)R$^{42}$, —NR$^{42}$C(=O)OR$^{42}$, —NR$^{42}$C(=O)N(R$^{42}$)$_2$, —OC(=O)R$^{42}$, —OC(=O)OR$^{42}$, or —OC(=O)N(R$^{42}$)$_2$;

each instance of R$^{42}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —C(=$NR^B$)$R^B$, —C(=$NR^B$)$OR^B$, —C(=$NR^B$)$N(R^B)_2$, —C(=O)$R^B$, —C(=O)$OR^B$, —C(=O)$N(R^B)_2$, —$NO_2$, —$NR^B$C(=O)$R^B$, —$NR^B$C(=O)$OR^B$, —$NR^B$C(=O)$N(R^B)_2$, —OC(=O)$R^B$, —OC(=O)$OR^B$, or —OC(=O)$N(R^B)_2$; and each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring.

10. The method of claim 2, wherein the compound according to Formula A is a compound having a formula of Formula Ac-1:

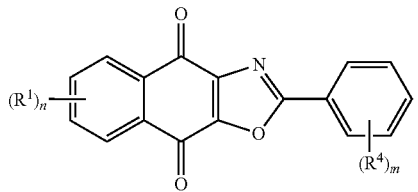

Formula Ac-1 wherein
n is 0, 1, 2, 3, or 4;

each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^{A1}$; —C(=O)$R^{A1}$; —C(=O)$N(R^{A1})_2$; —$CO_2R^{A1}$; —CN; —SCN; —$SR^{A1}$; —$SOR^{A1}$; —$SO_2R^{A1}$; —$NO_2$, —$N_3$; —$N(R^{A1})_2$; —NHC(=O)$R^{A1}$; —$NR^{A1}$C(=O)$N(R^{A1})_2$; —OC(=O)$R^{A1}$; —OC(=O)$R^{A1}$; —OC(=O)$N(R^{A1})_2$; —$NR^{A1}$C(=O)$OR^{A1}$; or —C($R^{A1}$)$_3$;

each occurrence of $R^{A1}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A2}$, —$N(R^{A2})_2$, —$SR^{A2}$, —CN, —SCN, —C(=$NR^{A2}$)$R^{A2}$, —C(=$NR^{A2}$)$OR^{A2}$, —C(=$NR^{A2}$)$N(R^{A2})_2$, —C(=O)$R^{A2}$, —C(=O)$OR^{A2}$, —C(=O)$N(R^{A2})_2$, —$NO_2$, —$NR^{A2}$C(=O)$R^{A2}$, —$NR^{A2}$C(=O)$OR^{A2}$, —$NR^{A2}$C(=O)$N(R^{A2})_2$, —OC(=O)$R^{A2}$, —OC(=O)$OR^{A2}$, or —OC(=O)$N(R^{A2})_2$;

each instance of $R^{A2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A2}$ groups are joined to form a substituted or unsubstituted heterocyclic or substituted or unsubstituted heteroaryl ring;

each instance of $R^4$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^B$, —$N(R^B)_2$, —$SR^B$, —CN, —SCN, —C(=$NR^B$)$R^B$, —C(=$NR^B$)$OR^B$, —C(=$NR^B$)$N(R^B)_2$, —C(=O)$R^B$, —C(=O)$OR^B$, —C(=O)$N(R^B)_2$, —$NO_2$, —$NR^B$C(=O)$R^B$, —$NR^B$C(=O)$OR^B$, —$NR^B$C(=O)$N(R^B)_2$, —OC(=O)$R^B$, —OC(=O)$OR^B$, or —OC(=O)$N(R^B)_2$;

each instance of $R^B$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^B$ groups are joined to form a substituted or unsubstituted heterocyclic or substituted or unsubstituted heteroaryl ring; and m is 0, 1, 2, 3, 4, or 5.

11. The method of claim 2, wherein the compound according to Formula A is a compound selected from the group consisting of:

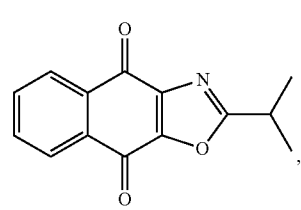

(1)

(2) 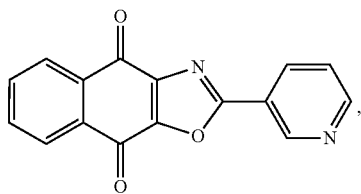

(3) 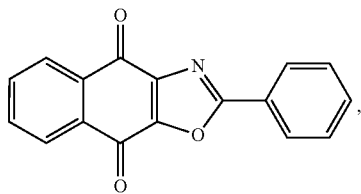

(4) 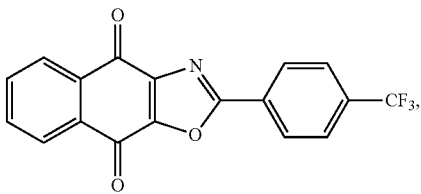

and (5) 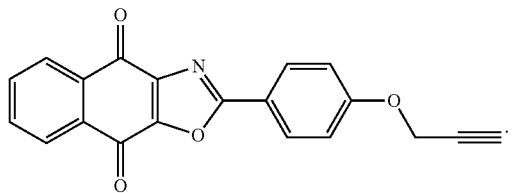

12. The method of claim 2, wherein the prostate cancer is a cyclin D1- and/or USP2a-dependent prostate cancer.

13. The method of claim 12, further comprising identifying the subject as having a cyclin D1- and/or USP2a-dependent prostate cancer.

14. The method of claim 2, wherein the prostate cancer is an androgen receptor (AR)- and/or USP12-dependent prostate cancer.

15. The method of claim 14, further comprising identifying the subject as having an androgen receptor (AR)- and/or USP12-dependent prostate cancer.

16. The method of claim 2, wherein the prostate cancer is resistant to androgen receptor (AR) inhibitor therapy.

* * * * *